(12) United States Patent
Witte et al.

(10) Patent No.: US 10,241,199 B2
(45) Date of Patent: Mar. 26, 2019

(54) ULTRASONIC/PHOTOACOUSTIC IMAGING DEVICES AND METHODS

(71) Applicant: The Arizona Board of Regents on Behalf of the University of Arizona, Tucson, AZ (US)

(72) Inventors: Russell S. Witte, Tucson, AZ (US); Leonardo Gabriel Montilla, Tucson, AZ (US); Ragnar Olafsson, Tucson, AZ (US); Charles M. Ingram, Tucson, AZ (US); Zhaohui Wang, Tucson, AZ (US); Robert A. Norwood, Tucson, AZ (US); Charles Greenlee, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 934 days.

(21) Appl. No.: 14/533,013

(22) Filed: Nov. 4, 2014

(65) Prior Publication Data

US 2015/0226845 A1    Aug. 13, 2015

Related U.S. Application Data

(62) Division of application No. 13/517,942, filed as application No. PCT/US2011/022420 on Jan. 25, 2011, now Pat. No. 8,879,352.

(Continued)

(51) Int. Cl.
*G01S 7/00* (2006.01)
*G01S 7/52* (2006.01)
*A61B 5/00* (2006.01)
*A61B 8/08* (2006.01)

(Continued)

(52) U.S. Cl.
CPC ........ *G01S 7/52017* (2013.01); *A61B 5/0093* (2013.01); *A61B 5/0095* (2013.01);
(Continued)

(58) Field of Classification Search
USPC .............................................. 367/7
See application file for complete search history.

(56) References Cited

U.S. PATENT DOCUMENTS 2,832,214 A * 4/1958 Trommler .............. G01H 9/002
367/7
6,115,624 A * 9/2000 Lewis .................... A61B 5/035
600/376

(Continued)

FOREIGN PATENT DOCUMENTS

WO  WO 2009/055705 A2   4/2009
WO  WO 2010/080991 A2   7/2010

OTHER PUBLICATIONS

International Search Report and Written Opinion of the International Searching Authority, dated Jul. 8, 2011, for corresponding International Application No. PCT/US2011/022420, 16 pages.

(Continued)

*Primary Examiner* — James R Hulka
(74) *Attorney, Agent, or Firm* — Klarquist Sparkman, LLP

(57) ABSTRACT

Devices are disclosed for obtaining data of a sample, particularly data capable of being processed to produce an image of a region of the sample. An exemplary device includes a light-beam source, an acoustic-wave source, an optical element, and an acoustic detector. The optical element is transmissive to a light beam produced by the light-beam source and reflective to acoustic waves produced by the acoustic-wave source. The optical element is situated to direct the transmitted light beam and reflected acoustic wave simultaneously along an optical axis to be incident at
(Continued)

a situs in or on a sample to cause the sample to produce acoustic echoes from the incident acoustic waves while also producing photoacoustic waves from the incident light beam photoacoustically interacting with the situs. The acoustic detector is placed to receive and detect the acoustic echoes and the photoacoustic waves from the situs. The acoustic detector can comprise one or more hydrophones exploiting the acousto-electric effect.

19 Claims, 51 Drawing Sheets

Related U.S. Application Data

(60) Provisional application No. 61/336,647, filed on Jan. 25, 2010, provisional application No. 61/337,607, filed on Feb. 10, 2010.

(51) Int. Cl.
  G01N 21/17  (2006.01)
  G01N 29/06  (2006.01)
  G01N 29/24  (2006.01)
  G01S 15/02  (2006.01)

(52) U.S. Cl.
  CPC ........... *A61B 8/08* (2013.01); *G01N 21/1702* (2013.01); *G01N 29/0672* (2013.01); *G01N 29/2418* (2013.01); *G01S 7/52* (2013.01); *G01S 15/02* (2013.01); *A61B 5/7257* (2013.01); *A61B 8/0825* (2013.01); *G01N 2291/02475* (2013.01)

(56) References Cited

U.S. PATENT DOCUMENTS

| | | | |
|---|---|---|---|
| 6,979,292 B2 | 12/2005 | Kanayama et al. | |
| 8,879,352 B2* | 11/2014 | Witte | A61B 5/0093 367/7 |
| 2002/0068869 A1* | 6/2002 | Brisken | A61N 7/00 600/439 |
| 2005/0004458 A1* | 1/2005 | Kanayama | A61B 5/0091 600/437 |
| 2007/0161902 A1* | 7/2007 | Dan | A61B 8/481 600/458 |
| 2008/0183076 A1* | 7/2008 | Witte | A61B 5/0093 600/438 |
| 2009/0005685 A1 | 1/2009 | Nagae et al. | |
| 2010/0091613 A1* | 4/2010 | Witte | G01H 11/06 367/149 |

OTHER PUBLICATIONS

Maslov et al., "Optical-resolution photoacoustic microscopy for in vivo imaging of single capillaries," *Optics Letters*, 33(9):929-931, May 1, 2008.

Montilla et al., "Real-Time Pulse Echo and Photoacoustic Imaging Using an Ultrasound Array and In-line Reflective Illumination," *Proceedings SPIE*, 7564:75643C-1-75643C-9, Jan. 24, 2010.

Ranasinghesagara et al., "Photoacoustic technique for assessing optical scattering properties of turbid media," *Journal of Biomedical Optics.*, 14(4):040504-1-040504-3, Jul./Aug. 2009.

Rao et al., "Hybrid-scanning optical-resolution photoacoustic microscopy for in vivo vasculature imaging," *Optics Letters*, 35(10):1521-1523, May 15, 2010.

Shi et al., "Optical resolution photoacoustic microscopy using novel high-repetition-rate passively Q-switched microchip and fiber lasers," *Journal of Biomedical Optics*, 15(5):056017-1-056017-7, Sep./Oct. 2010.

Witte et al., "Inexpensive acoustoelectric hydrophone for mapping high intensity ultrasonic fields,"*Journal of Applied Physics*, 104:54701-1-54701-3, Sep. 5, 2008.

Zemp et al., "A Photoacoustic Method for Optical Scattering Measurements in Turbid Media," *Proc. of SPIE*, 7177:71770Q-1-71770Q-9, Feb. 2009.

\* cited by examiner

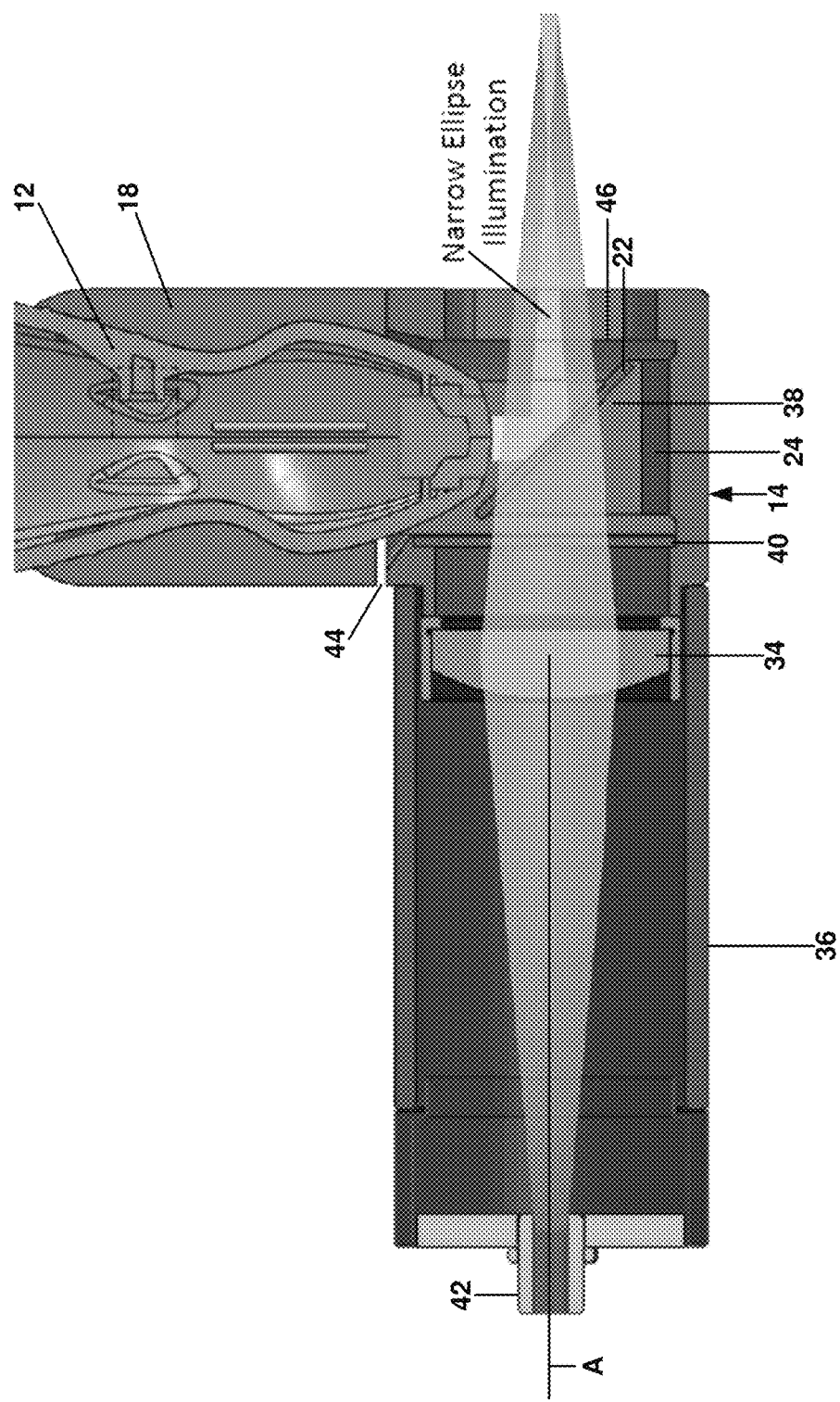

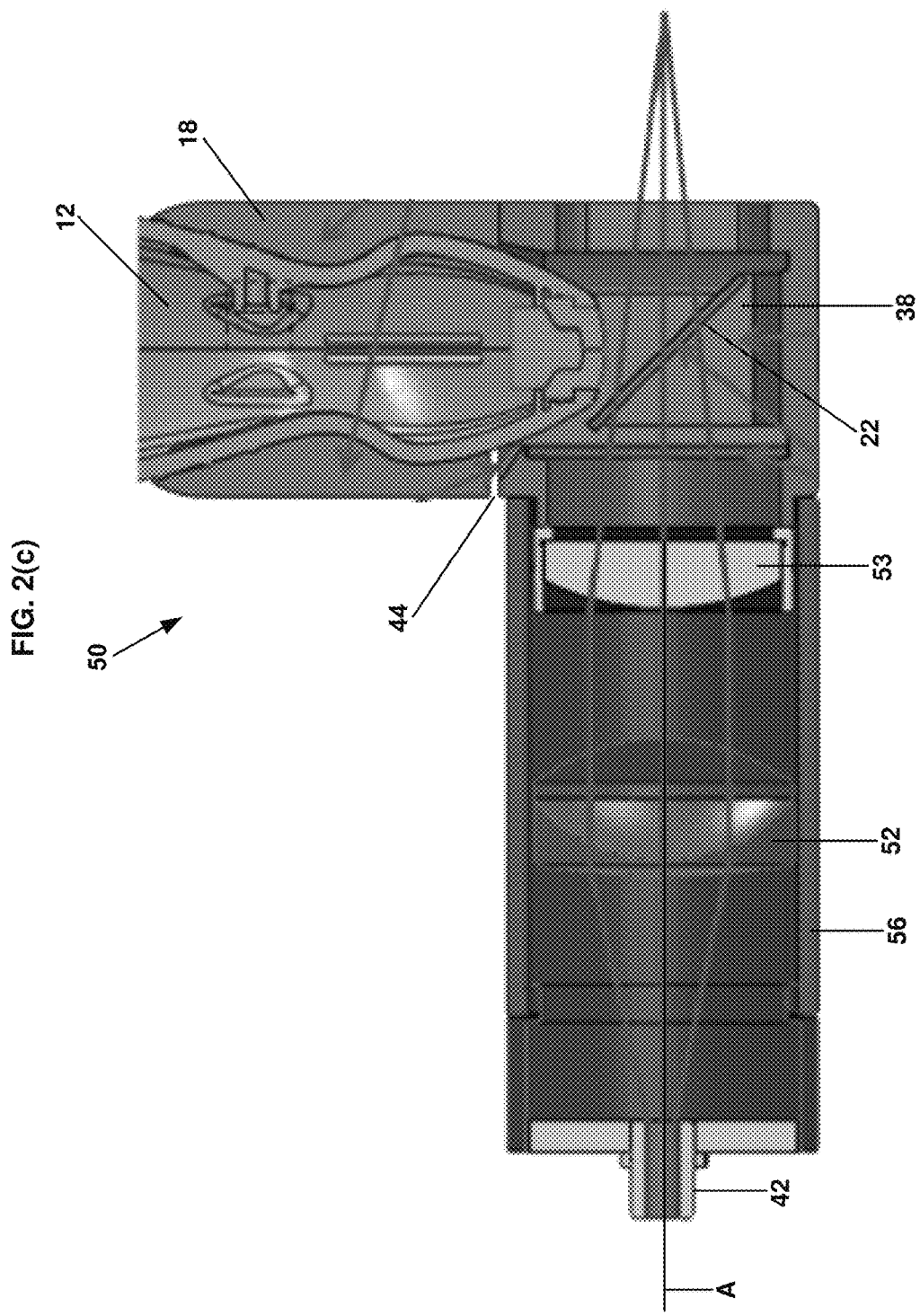

FIG. 9(a)
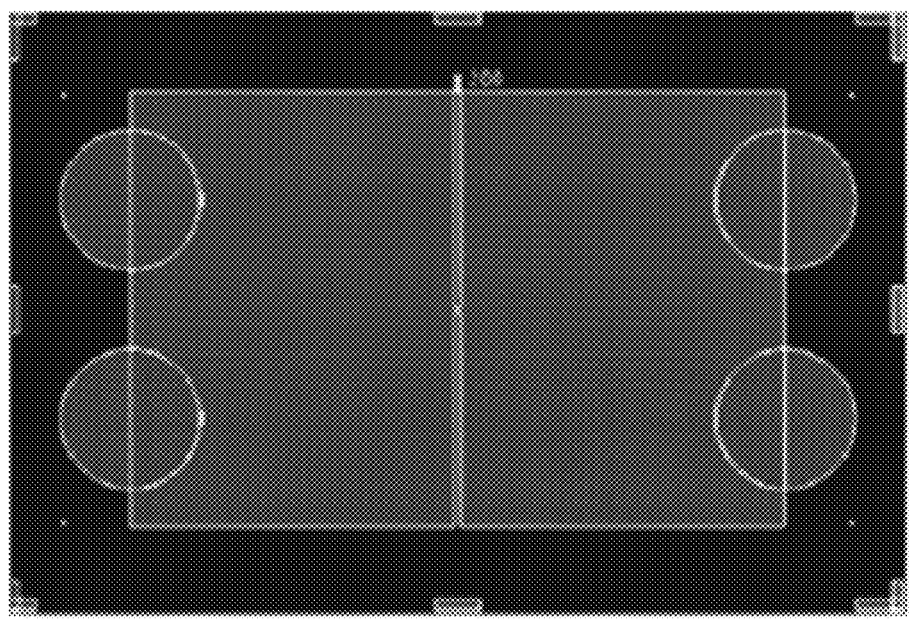
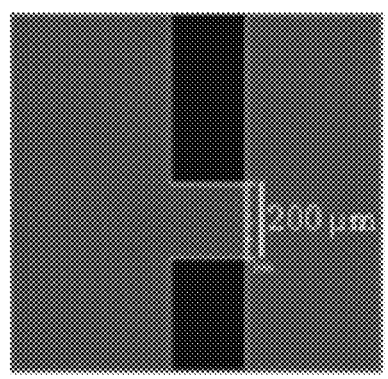

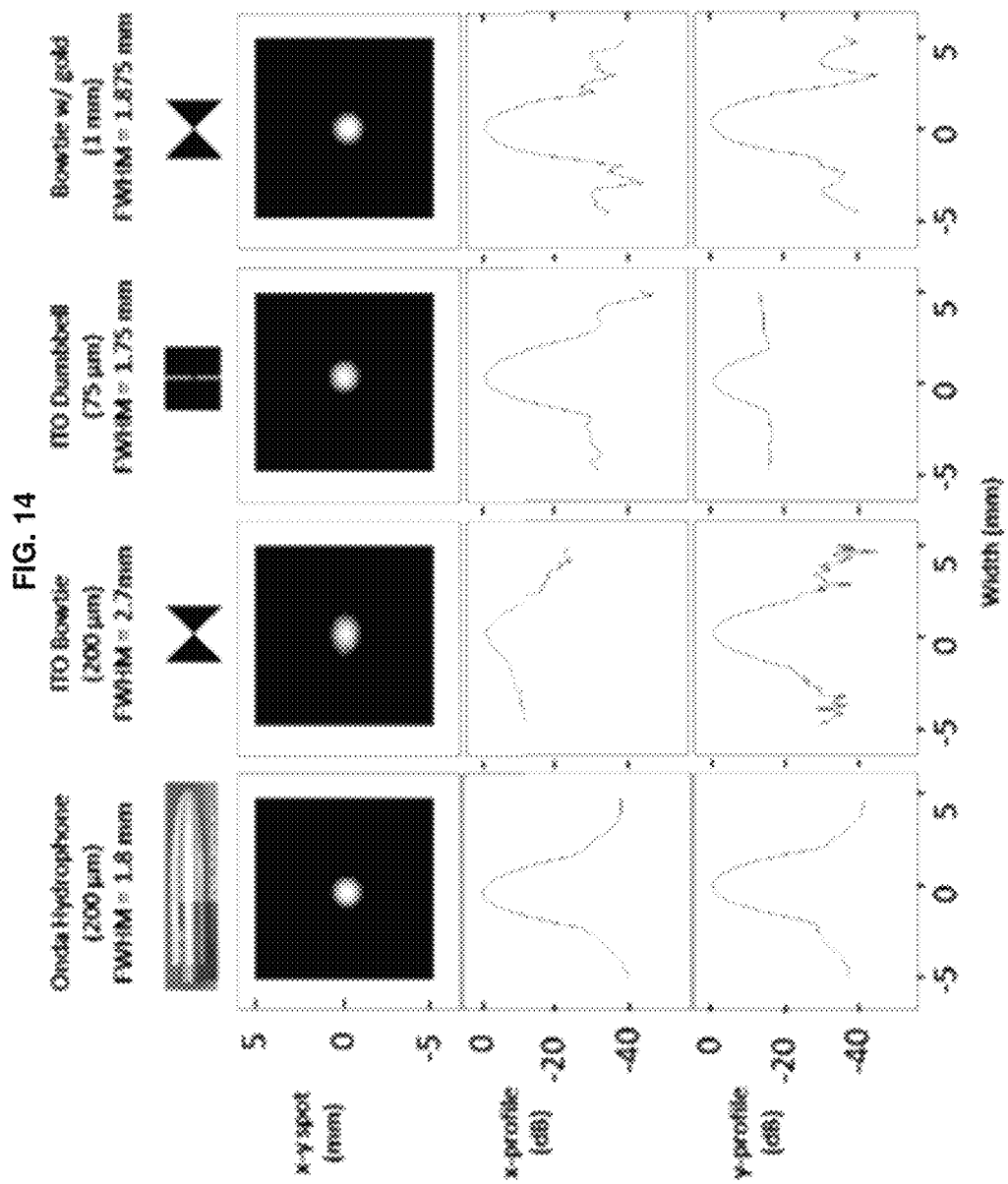

FIG. 17(b)  Side View  FIG. 17(a)

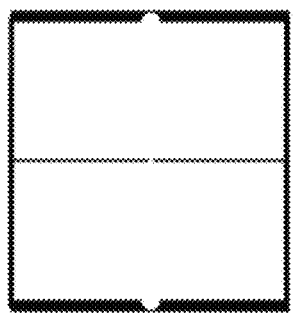
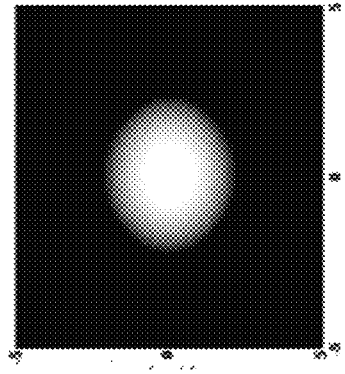
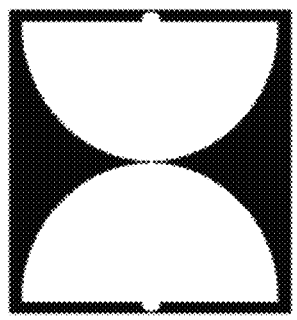
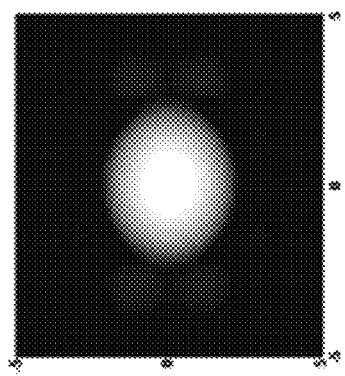
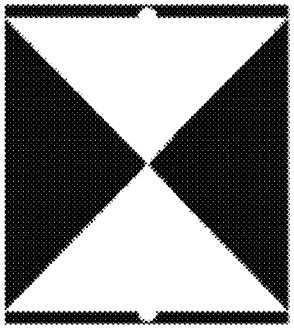
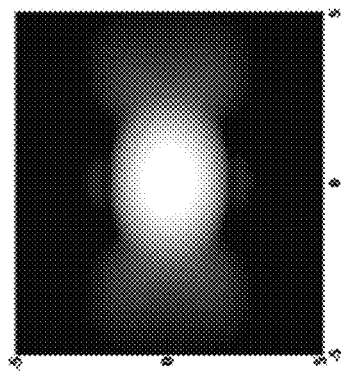
FIG. 20(a)
FIG. 20(b)

Beam pattern (40dB)

Dumbbell (Rel=1, 40dB)

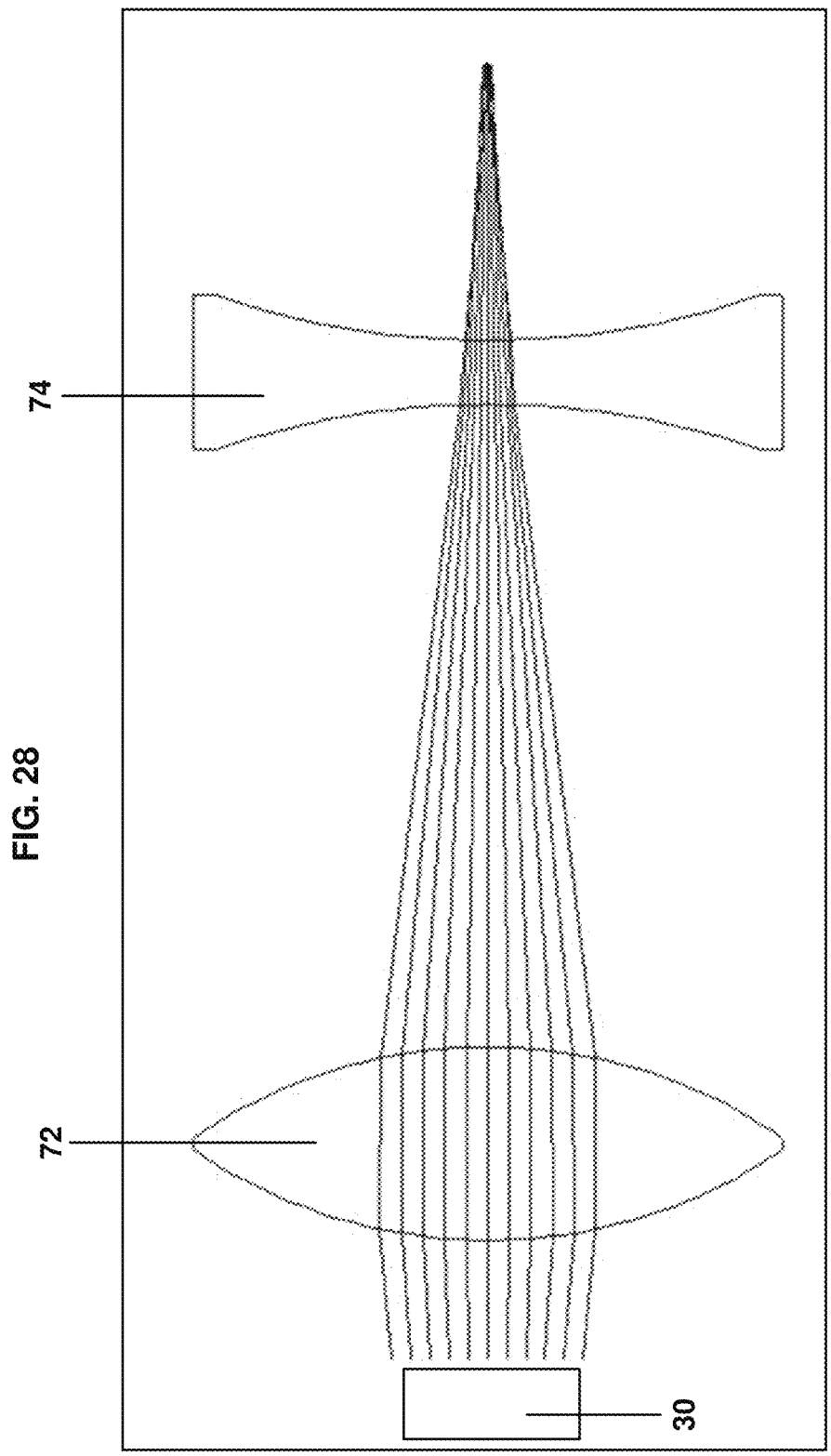

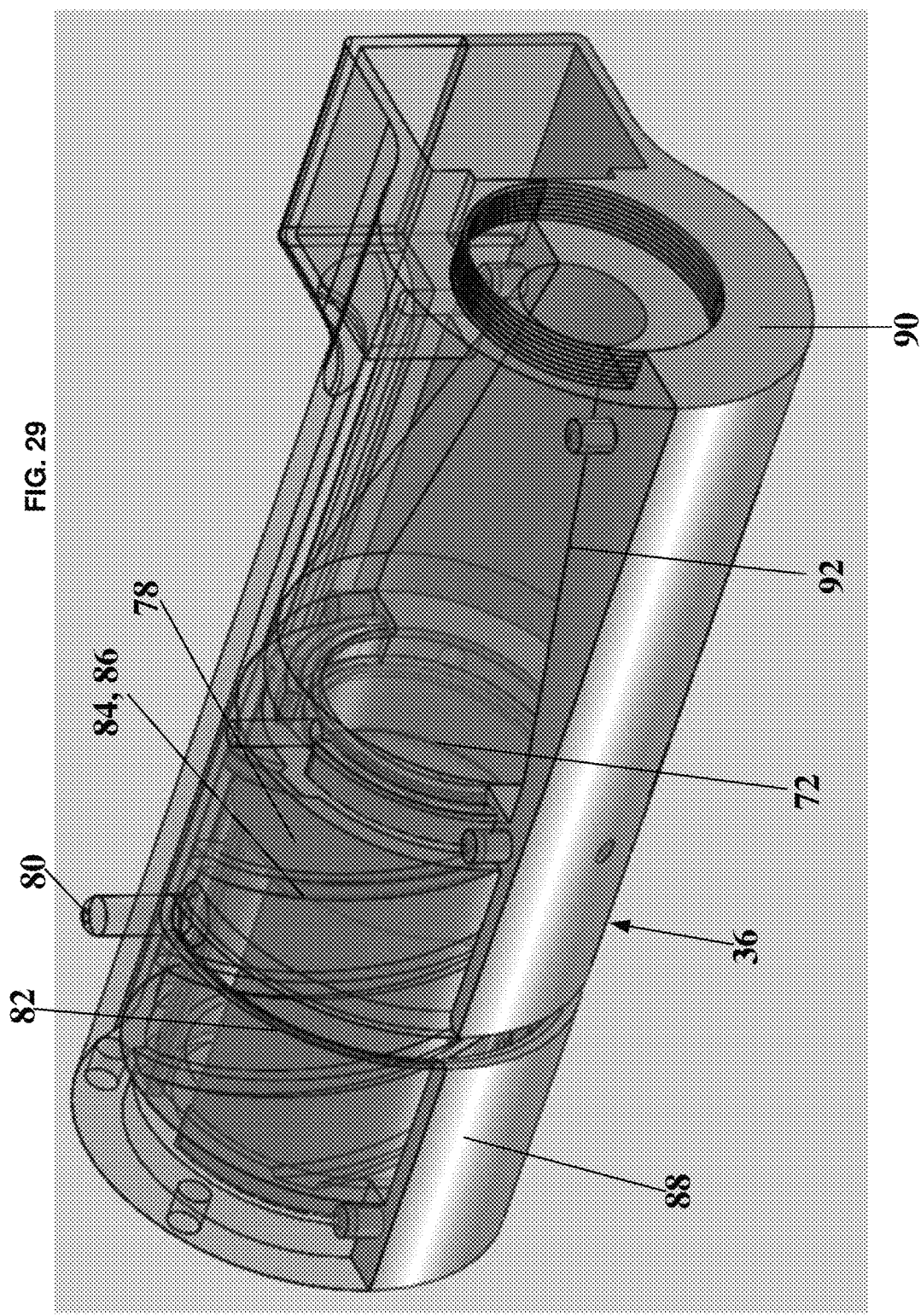

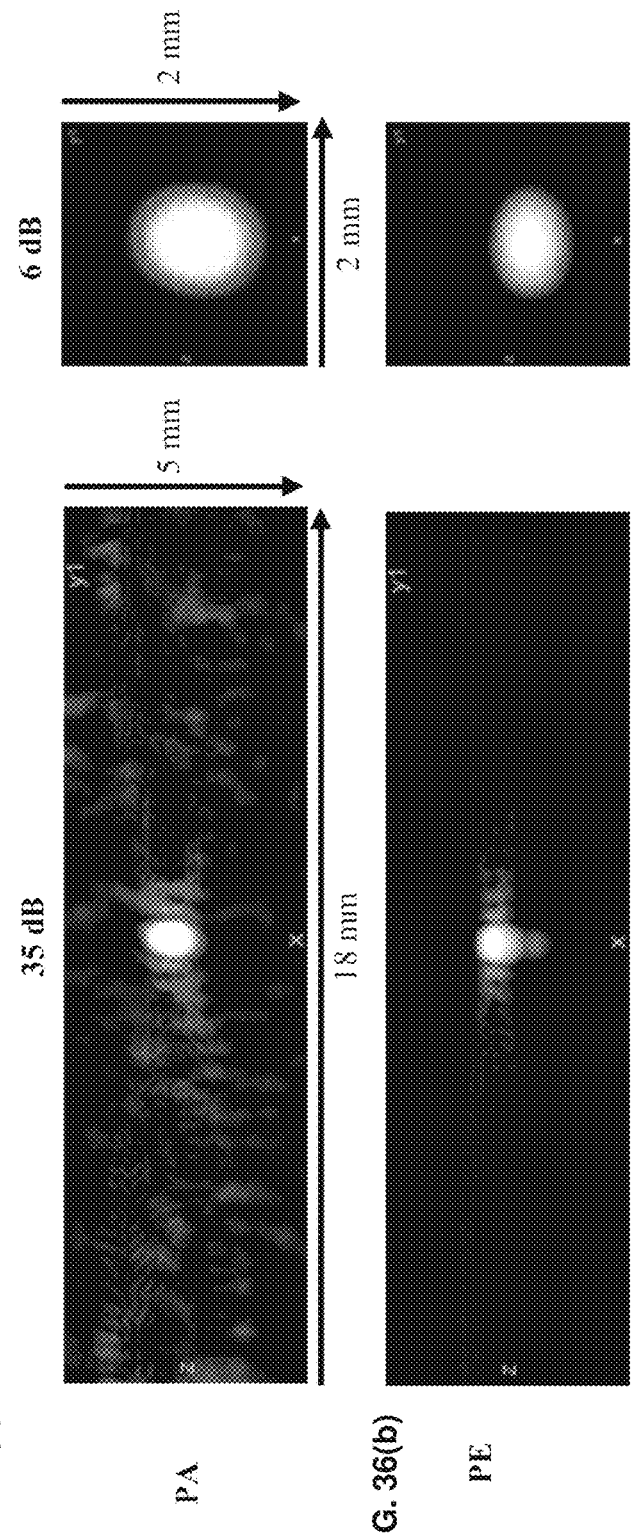
FIG. 36(a) PA
FIG. 36(b) PE under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample, under the sample.

ULTRASONIC/PHOTOACOUSTIC IMAGING DEVICES AND METHODS

CROSS-REFERENCE TO RELATED APPLICATION

This application is a divisional of U.S. patent application Ser. No. 13/517,942, filed Jun. 20, 2012, which is the U.S. National Stage of International Application No. PCT/US2011/022420, filed Jan. 25, 2011, which in turn claims priority to and the benefit of U.S. Provisional Patent Application No. 61/336,647, filed Jan. 25, 2010, and U.S. Provisional Patent Application No. 61/337,607, filed Feb. 10, 2010, all of which are incorporated herein by reference in their respective entireties.

ACKNOWLEDGMENT OF GOVERNMENT SUPPORT

This invention was made with government support under Grant No. 0853618 awarded by National Science Foundation and Grant No. R01 EB009353 awarded by National Institutes of Health. The government has certain rights in the invention.

FIELD

This disclosure pertains to, inter alia, imaging devices and methods based on at least two of the following principles for imaging and detection: ultrasonic, photoacoustic, and acousto-electric.

BACKGROUND

In medicine, the ability to obtain an image of a disease situs, especially one that is located depth-wise in a patient's tissue mass, is an important part of diagnosis and therapy. Cancer is an exemplary disease condition in which imaging is key. For example, with breast cancer, X-ray mammography is an important imaging modality used mainly for primary screening, while other imaging modalities such as ultrasonography and magnetic resonance offer second-stage detection that can provide useful information without having to perform an invasive procedure such as a biopsy. Unfortunately, X-ray mammography, in addition to using hazardous ionizing radiation and engendering patient discomfort, produces a high number of false-positives, has relatively low sensitivity, and sometimes produces false-negatives especially in radiographically dense breast tissue.

Another important imaging modality for various disease-related and other purposes is ultrasonic scanning, which has high sensitivity but low tissue specificity. Ultrasonic imaging is performed using an ultrasonic scanning machine to which a "probe" comprising one or more piezoelectric transducers is connected. Electrical pulses produced by the machine are converted by certain of the piezoelectric transducer(s) into corresponding ultrasound pulses of a desired frequency (usually between 2 and 18 MHz). The sound is focused either by the shape of the sending transducer(s), a "lens" in front of the transducer, or a complex set of control pulses from the ultrasonic scanning machine. Focusing produces a shaped acoustic wave propagating from the transducer. The sound wave enters the sample (e.g., a subject's body) and converges to focus at a desired depth in the sample. Most ultrasonic probes include a face member made of a material providing impedance matching for transmitting ultrasonic pulses efficiently into the subject's body. Also, a hydrogel is usually applied between the subject's skin and the face member of the probe for efficient propagation of sound waves to and from the probe. Portions of the sound wave are reflected from various tissue layers and structures in the sample, particularly from loci exhibiting density changes. Some of the reflected sound returns to the probe, in which certain transducer(s) convert the received sound into corresponding electrical pulses that are converted by the ultrasonic scanning machine into an image.

Photoacoustic imaging (PAI) is an emerging biomedical imaging modality based on the photoacoustic effect. In PAI, light pulses (often from a laser) are delivered to a target locus ("situs") in or on a sample. Some of the pulse energy is absorbed at the situs and converted into heat. The transient heating causes a corresponding transient thermoelastic expansion of the situs, which produces a corresponding wideband ultrasonic emission from the situs. The generated ultrasonic waves are detected using one or more ultrasonic transducers that convert the detected waves into corresponding electrical pulses that are processed into corresponding images. The optical absorption of light by a biological sample is closely associated with certain physiological properties such as hemoglobin concentration and/or oxygen saturation. As a result, the magnitude of ultrasonic emission (the photoacoustic signal, which is proportional to the local energy deposition) from the situs reveals physiologically specific optical absorption contrast that facilitate formation of 2-D or 3-D images of the situs. Blood usually exhibits greater absorption than surrounding tissues, which provides sufficient endogenous contrast to allow PAI of blood vessels and tissues containing same. For example, PAI can produce high-contrast images of breast tumors in situ due to the greater optical absorption by the increased blood supply provided by the body to the tumor. Whereas conventional X-ray mammography and ultrasonography produce images of benign features as well as pathological features, PAI can produce information more specific to the malignant condition, such as enhanced angiogenesis at the tumor site.

Significant challenges currently limit PAI from widespread clinical use. For example, the geometrical constraints of the ultrasonic detector usually prevent direct illumination of the tissue, resulting in "dark" fields being present in locations where illumination is most needed. This situation is shown in FIG. 1, depicting a conventional arrangement of an ultrasonic detector array and two lasers. The respective beams produced by the lasers cross each other and thereby produce two dark fields, one being in the near field. Since the near field cannot be illuminated, a longer path length is required for ultrasonic waves from the illuminated region to the sensor array. FIG. 1 also shows that direct illumination of the situs becomes increasingly difficult as the physical dimensions of the detector increase, especially if the detector comprises an array of detector elements. Desirably, the detector should be acoustically coupled directly in front of the target situs tissue as the situs is being illuminated. But this is not possible in FIG. 1. In certain other conventional devices, illumination light is directed around a single-element detector. Unfortunately, these conventional devices require complicated optics and difficult setup procedures involving custom-made parts and sensitive alignments, and are too fragile to apply in a clinical setting. With these conventional devices it is also difficult to couple sufficient light to the small available illumination area, especially in view of the safety limits for exposure to laser light. In addition, most of these designs require application of complex deconvolution algorithms for making direct quantitative measurements.

Other limitations of conventional clinical PAI imaging include: (1) scan times are slow (>15 minutes) due to a lack of appropriate parallel receiving architecture; (2) conventional pulse echo (PE) images cannot be obtained simultaneously with the PAI images; and (3) the current PAI apparatus are bulky and expensive (most use a large laser that is difficult to transport).

Hence, it would be desirable to be able to obtain more informational images of a situs by both ultrasonography and PAI applied in a manner that produces real-time image information by these modalities that exploit different contrast mechanisms.

SUMMARY

Various aspects of the invention are directed to, inter alia, devices for obtaining data of a sample and also to acoustic detectors, imaging devices, photoacoustic-enabling devices, and methods for producing data concerning a situs in or on a sample.

An embodiment of a device for obtaining data of a sample comprises a light-beam source, an acoustic-wave source (e.g., source of ultrasonic pulses), an optical element, and an acoustic detector device. The optical element is transmissive to a light beam produced by the light-beam source while also being reflective to acoustic waves produced by the acoustic-wave source. The optical element is placed to direct the transmitted light beam and the reflected acoustic wave simultaneously along a first axis to be incident at a situs in or on a sample to cause the sample to produce acoustic echoes from the incident acoustic waves while also producing photoacoustic waves from the incident light beam photoacoustically interacting with the situs. The acoustic detector device is placed to receive and detect the acoustic echoes and the photoacoustic waves from the situs.

In some embodiments the light beam beam produced by the source is incident along the first axis to the optical element while acoustic waves from the acoustic-wave source are incident along a second axis (different from the first axis) to the optical element. The acoustic echoes and photoacoustic waves produced by the situs and returning to the optical element are reflected by the optical element along the second axis to the detector. The acoustic echoes and photoacoustic waves can co-propagate as a combined acoustic beam to the acoustic detector. The first axis desirably is normal to the situs, and the second axis desirably is perpendicular to the first axis.

In some embodiments the acoustic detector device comprises the acoustic-wave source. The acoustic-wave source can be, but need not be, an ultrasonic scanning probe used with a conventional ultrasonic scanning system. Certain of the acoustic detector devices can be called "photoacoustic-enabling devices" (PEDs) because they enable the scanning probe (and ultrasonic imaging system to which the probe is connected) to obtain, in addition to pulse-echo and closely related image data, photoacoustic data regarding the situs. These data can be obtained simultaneously to produce images of the situs obtained in real-time by two different imaging modalities.

The light-beam source desirably is a source of light pulses (often, but not necessarily, in the form of a pulsatile laser) while the acoustic-wave source desirably is a source of ultrasonic pulses. The device can further comprise a controller connected to the light-beam source, the acoustic-wave source, and the acoustic detector device. Among its various functions, the controller desirably synchronizes output of light pulses from the light source with output of acoustic pulses from the acoustic-wave source.

In some embodiments the first optical element is placed also to receive the acoustic echoes and the photoacoustic waves from the situs and to reflect both to the acoustic detector.

In many embodiments the optical element comprises a parallel-plate element. The parallel-plate element can be oriented at respective 45° angles to the light beam and to the acoustic waves. An exemplary parallel-plate element is a microscope slide made of glass or quartz. (Quartz would be appropriate over glass if the wavelength of light produced by the light-beam source were, for example, in the UV range.) An optical element fashioned from a microscope slide is inexpensive, light-weight, rugged, easily cut to a required size if necessary, easily mountable, and effective.

The device can further comprise an optical system situated between the light-beam source and the optical element. The optical system shapes the beam of light produced by the light-beam source for efficient transmission through the optical element and impingement at the situs. By way of example, the optical system shapes the beam to converge as desired at the situs. To such end, the optical system desirably comprises at least one axially movable lens element for selectively adjusting light-beam focus appropriate for a given depth of the situs in the sample. An optical fiber or analogous component can be coupled between the light-beam source and the optical system to prevent the device placed relative to the situs being encumbered by the light source.

The device desirably further comprises an index-matching liquid between the optical element and the sample. The index-matching fluid has an index of refraction selected according to the refractive index of the sample. For medical or biological samples, a suitable index-matching fluid is water. Other commercially available liquids alternatively can be used. The liquid can be contained in a housing that also includes the optical element.

The acoustic detector device includes one or more acoustic detectors. Many embodiments comprise an array of multiple acoustic detectors. The array can be one-dimensional (particularly a linear array), two-dimensional (particularly a planar array), or three-dimensional. In some embodiments at least one acoustic detector is configured as an acousto-electric hydrophone as described herein.

In embodiments comprising at least one acousto-electric hydrophone, the hydrophone comprises a first electrode, a second electrode, and a sensitivity zone located between and in electrically conductive contact with the electrodes. The electrodes are connected so as to pass an electrical current through the sensitivity zone. The sensitivity zone is acousto-electrically responsive to incident acoustic-pressure waves by producing a change in voltage across the electrodes. The change in voltage is a signature of at least one parameter of the pulses of acoustic pressure incident to the sensitivity zone. These hydrophones, which can be in the form of an array of detectors, have broader applicability than being used as acoustic detectors of devices as summarized above. The hydrophones also can be used as acoustic detectors with any of various other devices, such as but not limited to, pulse-echo imaging devices.

Another aspect of the invention is directed to devices for imaging a situs in a sample. An embodiment of such a device comprises an ultrasonic-detector portion and a photoacoustic portion. The ultrasonic-detector portion comprises at least one ultrasonic transmitter and at least one ultrasonic receiver. The photoacoustic portion comprises a detector mount, an acoustic-reflection element, and an illumination portion. The ultrasonic-detector portion is coupled to the detector mount such that at least one ultrasonic transmitter and at least one ultrasonic receiver are oriented to send and receive, respectively, ultrasonic beams propagating on a first axis. The illumination portion is coupled to the detector mount such that the illumination portion directs a pulsatile or modulated light beam along a second axis that is different from (desirably perpendicular to) and intersects the first axis. The acoustic-reflection element is configured to transmit the light beam from the illumination portion and simultaneously to reflect the ultrasonic beam sent from the ultrasonic transmitter. The acoustic-reflection element is coupled to the detector mount to receive and transmit the light beam along the second axis, to receive the ultrasonic beam along the first axis, and to reflect the ultrasonic beam to co-propagate with the transmitted light beam along the second axis to the situs. Thus, the situs is induced simultaneously to produce pulse echoes and photoacoustic pulses that co-propagate from the situs along the second axis to the acoustic-reflection element. The acoustic-reflection element reflects the pulse echoes and photoacoustic pulses along the first axis to at least one ultrasonic receiver.

The imaging device can further comprise a light source that produces the pulsatile light beam, and a light conduit coupled to the light source and to the illumination portion to conduct the light beam from the light source to the illumination portion. In some embodiments the illumination portion further comprises an optical system situated between the light conduit and the illumination portion to shape the light beam for entry into the acoustic-reflection element. The imaging device also desirably includes a chamber or the like, situated between the acoustic-reflection element and the sample, that contains an index-matching fluid selected based upon an index of refraction of the sample. Alternatively, the acoustic-reflection element may be in contact with the fluid.

Yet another aspect of the invention is directed to methods for producing data concerning a situs in or on a sample. An embodiment of such a method comprises combining a pulsed or modulated light beam and a pulsed acoustic beam to form an energy beam in which the acoustic beam is in-line with the light beam and the energy beam includes both light pulses and acoustic pulses. The energy beam is impinged at a situs on or in the sample to cause the situs to produce pulse echoes in response to the acoustic pulses incident at the situs and photoacoustic pulses in response to the light pulses incident at or in the vicinity of the situs. The acoustic echoes and photoacoustic pulses are detected to produce data concerning the situs.

Desirably, the light beam and the train of acoustic pulses are coaxial with and co-propagate with each other. The light beam in the energy beam desirably comprises a train of light pulses, and the acoustic-pulse beam in the energy beam desirably comprises a train of acoustic pulses. The light pulses and acoustic pulses in the energy beam desirably are synchronous with each other.

In some embodiments, producing the energy beam comprises producing the pulsed or modulated light beam propagating along a first axis extending to the situs, producing the acoustic-pulse beam propagating along a second axis different from the first axis, and combining the light beam and the acoustic-pulse beam so that the resulting energy beam propagates along the first axis to the situs. The acoustic echoes and photoacoustic pulses can be co-propagated as a returning acoustic-wave beam back along the first axis. The returning acoustic-wave beam is then split from the first axis to an acoustic-detector device. More specifically, the returning acoustic-wave beam can be split from the first axis to the second axis, along which the returning acoustic-wave beam propagates to the acoustic-detector device.

Detecting the acoustic echoes and the photoacoustic pulses in the returning acoustic-wave beam is performed using an acoustic-detector device comprising an array of multiple acoustic detectors that produce respective data from respective acoustic waves detected by the acoustic detectors. The method can further comprise processing the data to produce an image of the situs.

In various embodiments of the method, combining the pulsed or modulated light beam and the acoustic-pulse beam comprises interacting these beams with an optical element that transmits incident light and reflects incident acoustic waves, such that the light beam passes through the optical element and the acoustic-pulse beam is reflected by the optical element to form the energy beam.

The foregoing and additional features and advantages of the invention will be more readily apparent from the following detailed description, which proceeds with reference to the accompanying drawings.

BRIEF DESCRIPTIONS OF THE DRAWINGS

FIG. 1 shows oblique illumination used in conventional photoacoustic imaging devices, showing especially the dark fields that are not imaged.

FIG. 2(a) depicts an imaging device according to the first representative embodiment, including an illumination source (e.g., pulsed laser) coupled to an optical chamber, an acoustic-reflection chamber coupled to the optical chamber, and ultrasonic probe coupled to the acoustic-reflection chamber. The device of this embodiment is configured as a "PED" (photoacoustic enabling device) that enables a conventional ultrasonic probe array, used for conventional ultrasonic imaging, to be used also for photoacoustic imaging, including simultaneous imaging in real-time using both techniques.

Figure 4A:
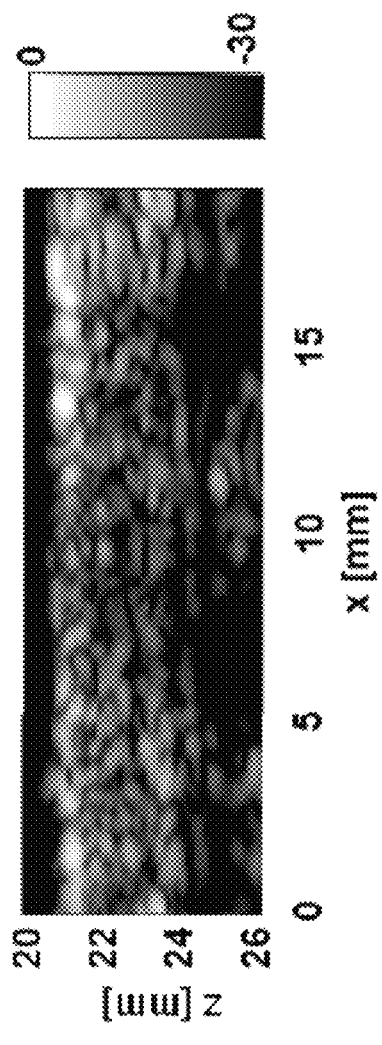
Figure 4B:
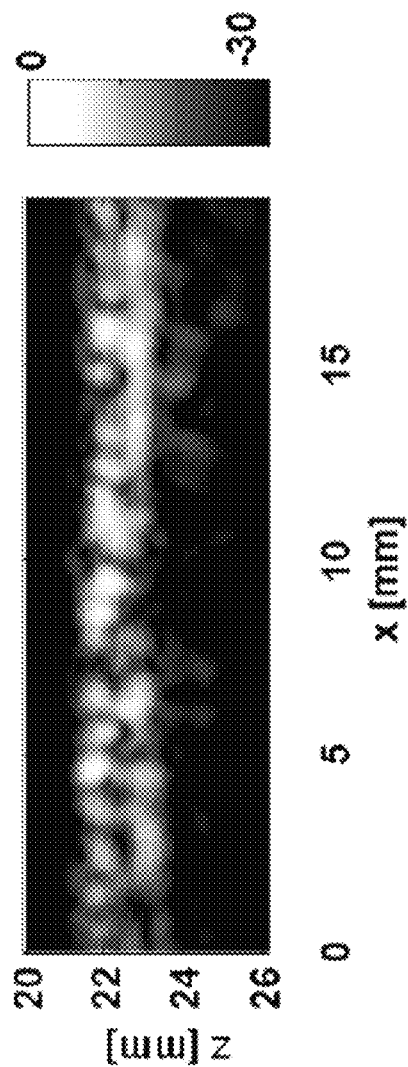

FIGS. 4(a) and 4(b) are longitudinal images obtained of a rat's tail obtained by real-time photoacoustic imaging and by simultaneous real-time photoacoustic imaging using an embodiment of an imaging device. Tail diameter was about 5 mm; light wavelength was 700 nm; scale bars are in dB.

Figure 5A:
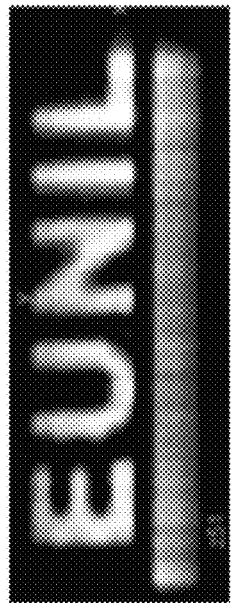

FIG. 5(a) is a photograph of a design that has been laser-printed on a transparency, used as a test phantom in Example 2.

Figure 5B:
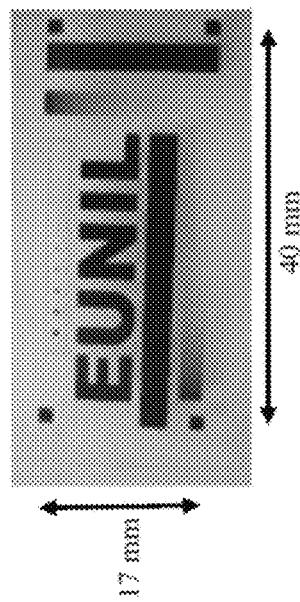

FIG. 5(b) is an image representing maximum projection along the axial (z) direction of the phantom of FIG. 5(a), produced with scan data acquired using a conventional method involving imaging a phantom in water with transillumination.

Figure 5C:
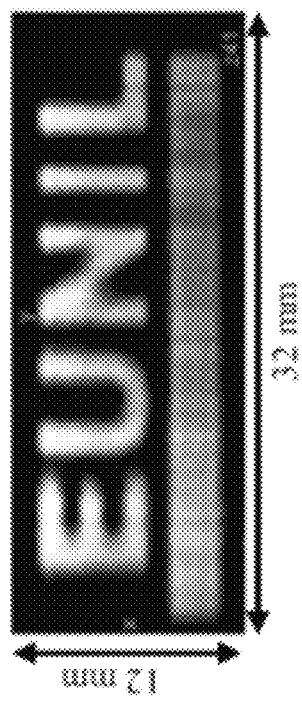

FIG. 5(c) is an image similar to that in FIG. 5(b) but produced with scan data obtained using a device according to the first representative embodiment.

Figure 6A:
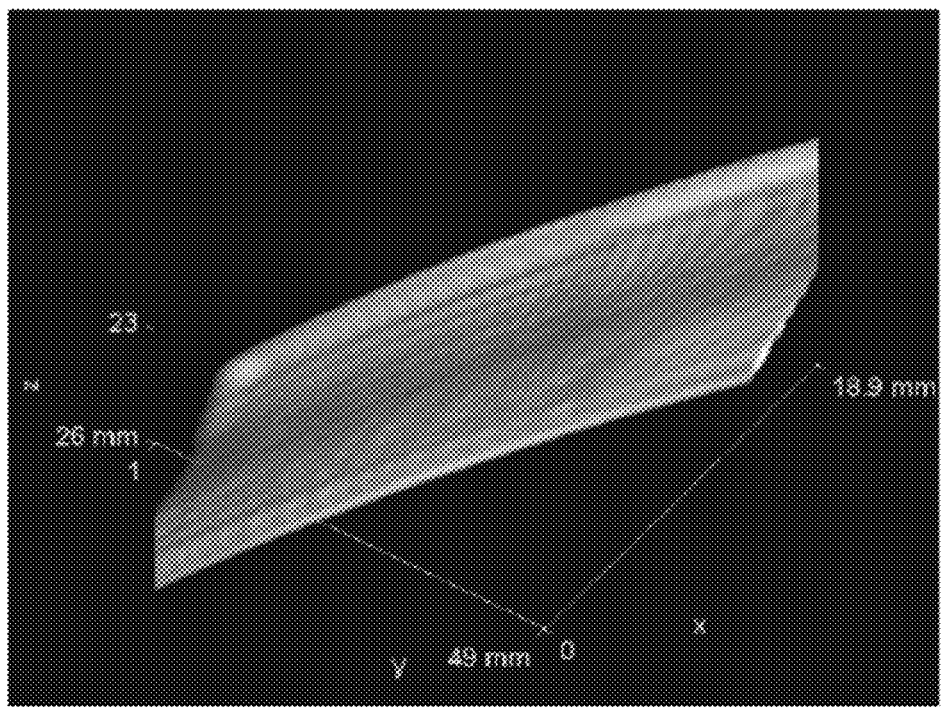
Figure 6B:
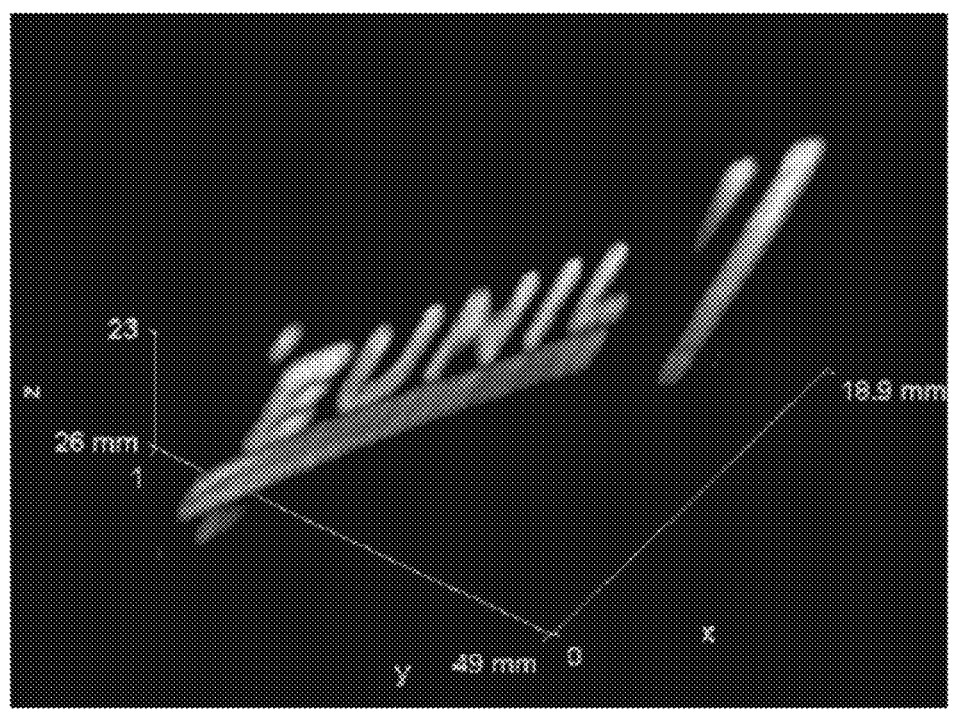

FIG. 6(a) is a 3-D rendering of the pulse-echo image of the transparency phantom, discussed in Example 2, used as a control for FIG. 6(b).

FIG. 6(b) is a 3-D rendering of the photoacoustic image of the transparency phantom, discussed in Example 2.

Figure 7A:
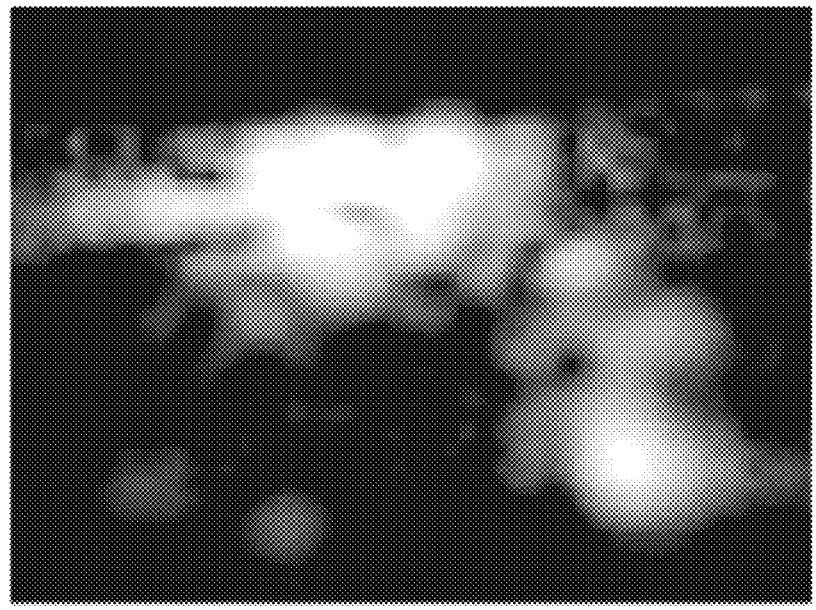

FIG. 7(a) is an image of an excised mouse pancreas as obtained by pulse-echo imaging, displayed with a dynamic range of −40 dB from peak intensity, as discussed in Example 3.

Figure 7B:
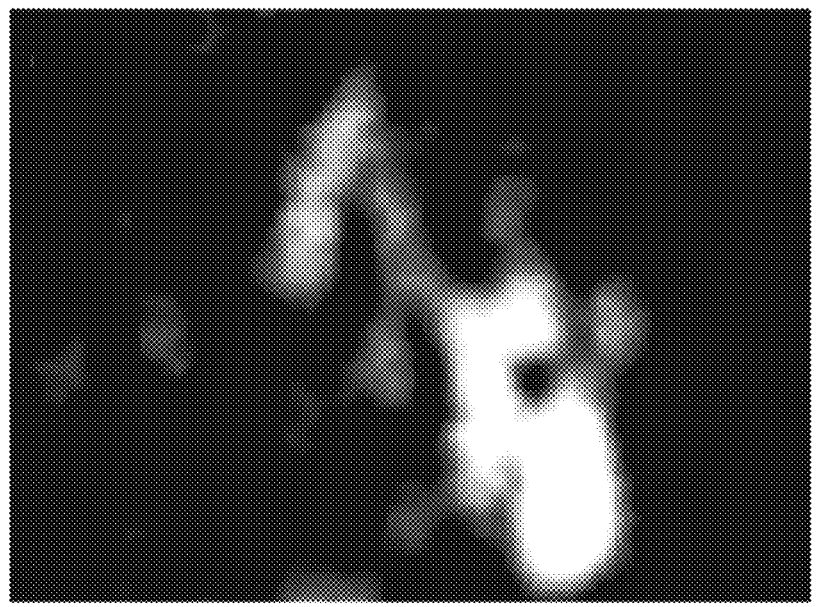

FIG. 7(b) is an image of the excised mouse pancreas shown in FIG. 7(a), but obtained by photoacoustic imaging using 800-nm light and a dynamic range of −15 dB from peak. The strong signal in the lower right quadrant suggests blood in that region.

Figure 8:
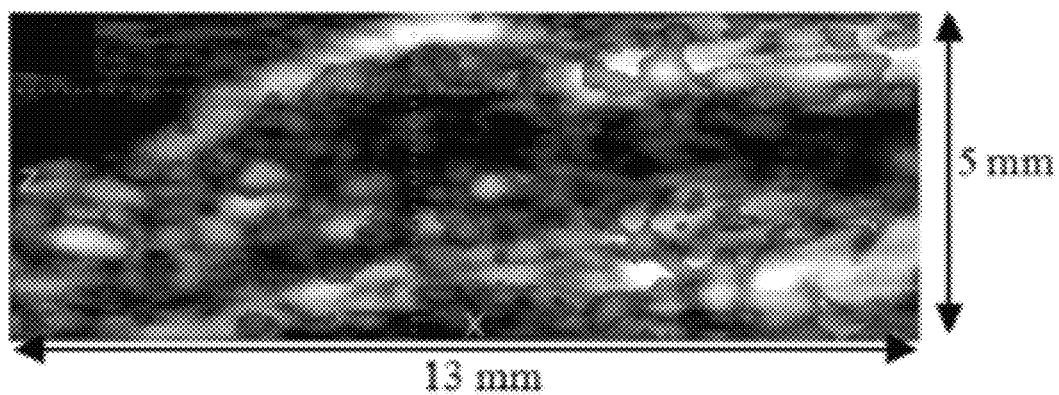

FIG. 8 is an in vivo photoacoustic image of a pancreatic tumor in a mouse (sagittal plane), as discussed in Example 3.

FIG. 9(a) is a plan view of a rectangular dumbbell acousto-electric hydrophone according to the third representative embodiment. The close-up image is of the 200 μm×200 μm sensitivity zone of the hydrophone.

Figure 9B:
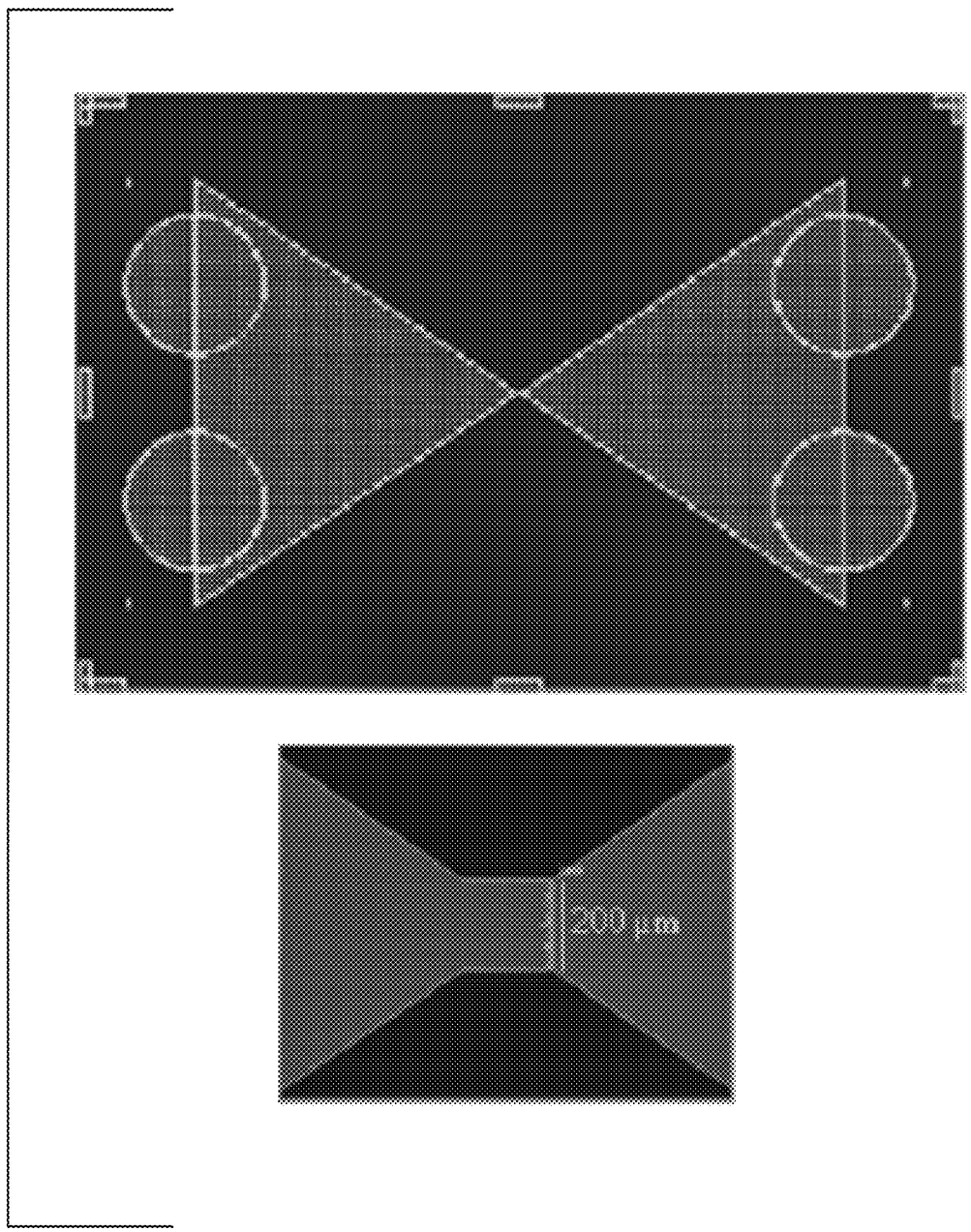

FIG. 9(b) is a plan view of a bowtie acousto-electric hydrophone according to the third representative embodiment. The close-up image is of the 200 μm×200 μm sensitivity zone of the hydrophone.

Figure 10:
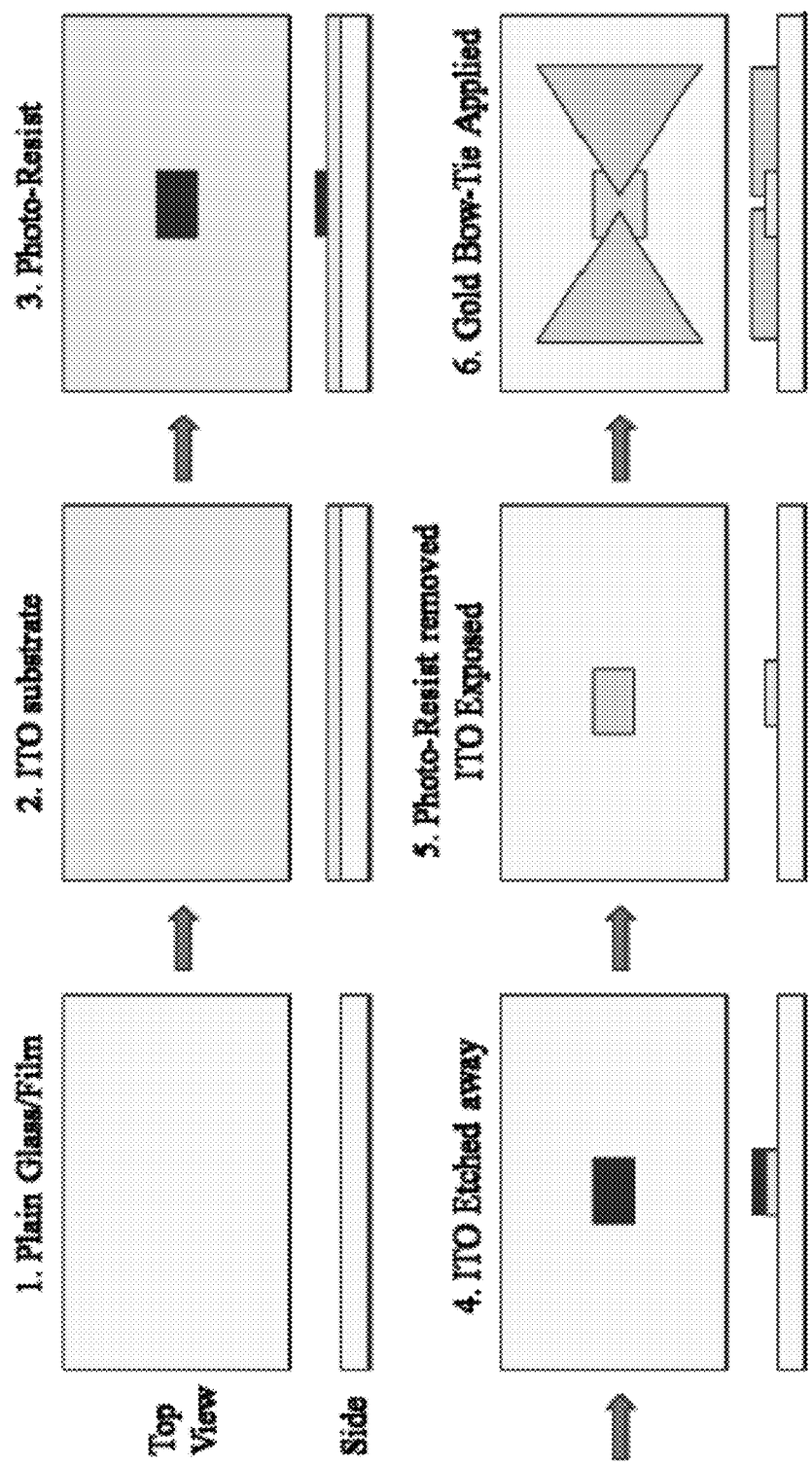

FIG. 10 is a schematic diagram of a photolithography process as used for fabricating an acousto-electric bowtie hydrophone, as discussed in the third representative embodiment.

Figure 11:
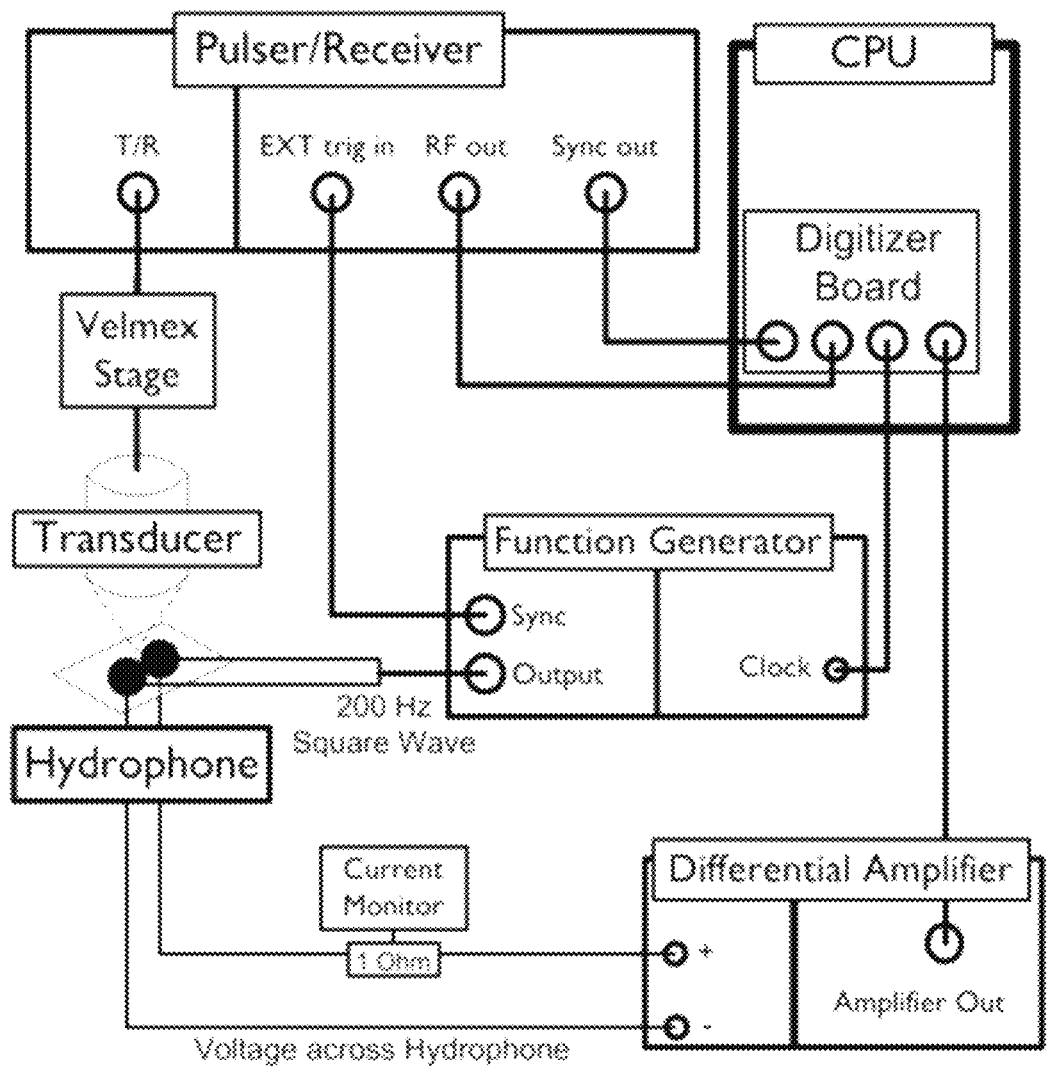

FIG. 11 is a schematic diagram of a test setup used for testing hydrophones, as discussed in Example 4.

Figure 12A:
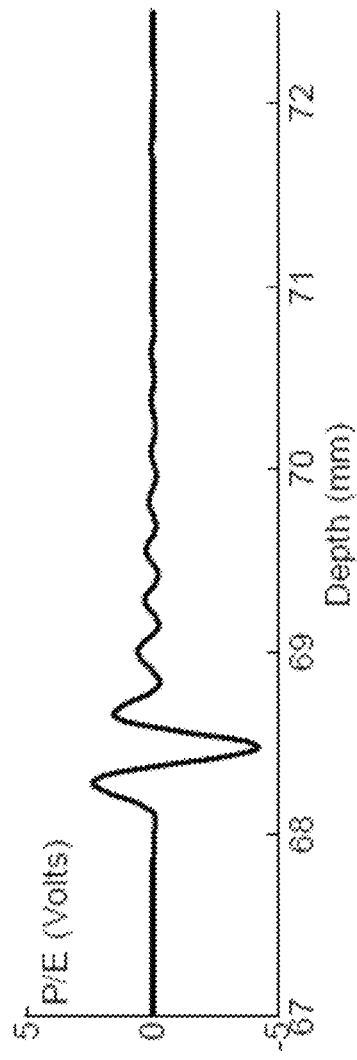

FIG. 12(a) is an A-line pulse-echo response of an indium-tin-oxide (ITO) dumbbell hydrophone, with a 75 μm×75 μm square sensitivity zone, to a pulse produced by a 2.25 MHz transducer, as discussed in Example 4.

Figure 12B:
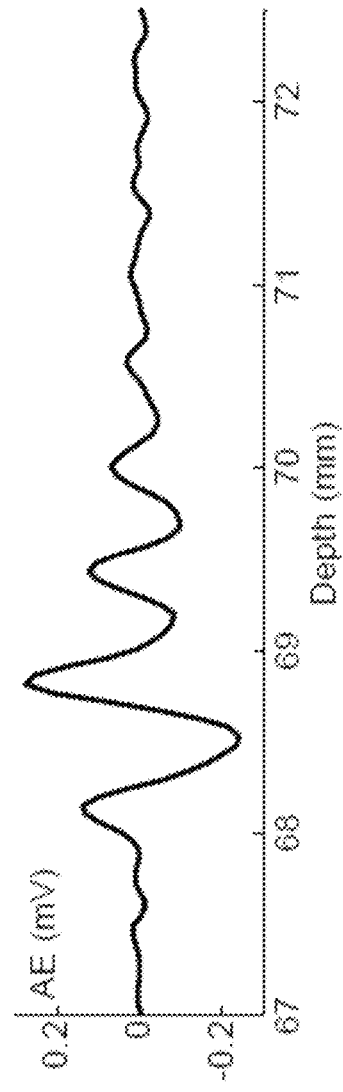

FIG. 12(b) is an acousto-electric response produced by the same hydrophone, as used in FIG. 12(a), at 500 kPa and 10-V applied voltage. The depth in mm is based on the measured response time multiplied by the speed of sound in water.

Figure 13:
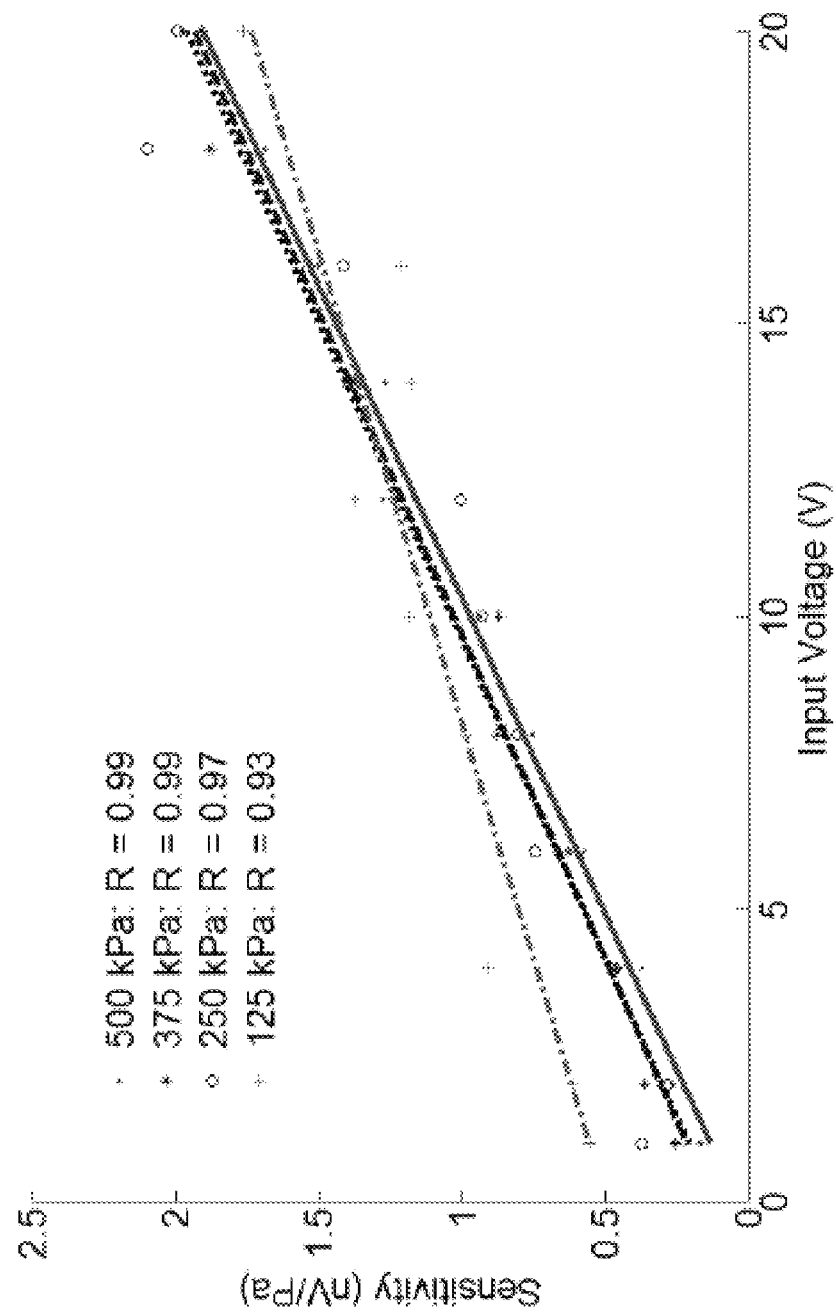

FIG. 13 is a plot of sensitivity versus applied voltage for a 100% ITO dumbbell hydrophone with a sensitivity zone of 75 μm×75 μm, at transducer pressure levels of 125 kPa, 250 kPa, 375 kPa, and 500 kPa, as discussed in Example 4. The fitted lines indicate a good linear response for all transducer pressures.

FIG. 14 shows beam profiles, with −6 dB spot images, for four hydrophones evaluated in Example 4. The 200 μm×200 μm bowtie and the 75 μm×75 μm dumbbell hydrophones were 100% ITO; the 1 mm×1 mm bowtie hydrophone was overlaid with gold electrodes except at the sensitivity zone.

Figure 15A:
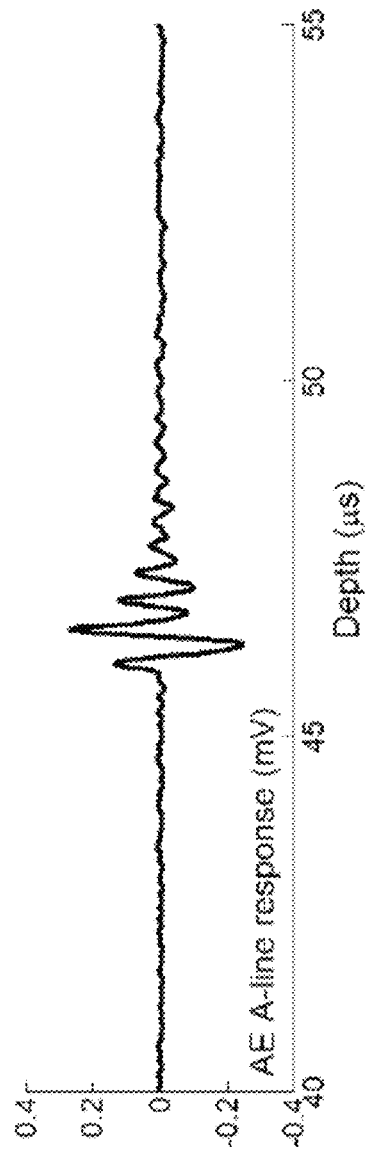
Figure 15B:
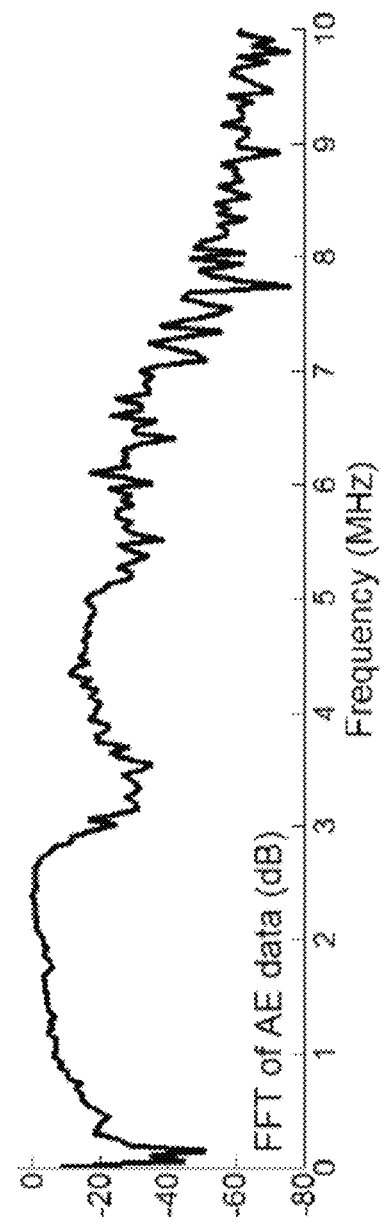

FIGS. 15(a) and 15(b) are plots of bandwidth for a 100% ITO (no gold) dumbbell hydrophone having a 75 μm×75 μm sensitivity zone, as discussed in Example 4. FIG. 15(a) is an AE signal time trace, and FIG. 15(b) is a corresponding fast Fourier transform showing $2^{nd}$ and $3^{rd}$ harmonics of the response to a 2.25 MHz transducer.

Figure 16A:
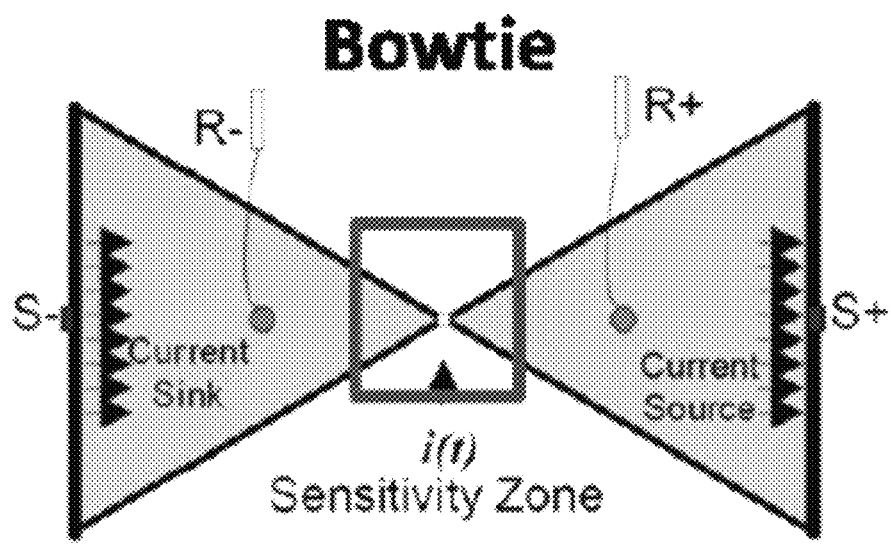

FIG. 16(a) is a schematic diagram of the fourth representative embodiment, detailing especially the bowtie hydrophone in which gold leads in the shape of a bow-tie converge to the sensitivity zone in the center. A first pair of electrodes is used to inject AC electrical current (typically ~200 Hz) into the hydrophone, and a second pair of electrodes is used for detecting the acousto-electric signal produced by the hydrophone.

Figure 16B:
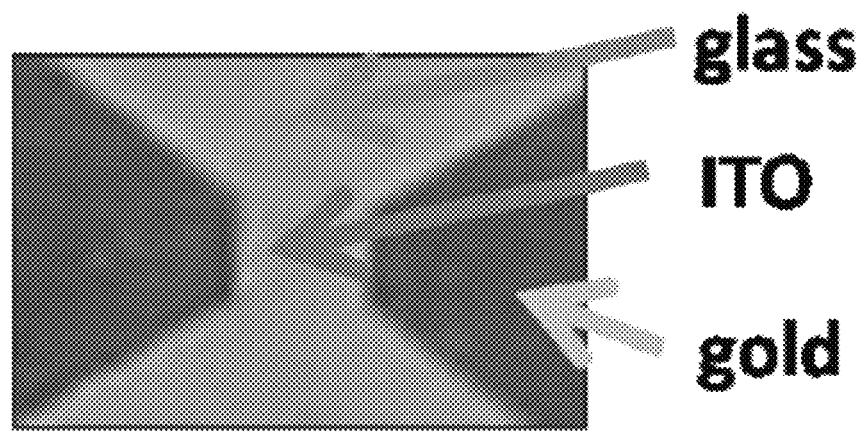

FIG. 16(b) shows the sensitivity zone of the hydrophone of FIG. 16(a).

Figure 17C:
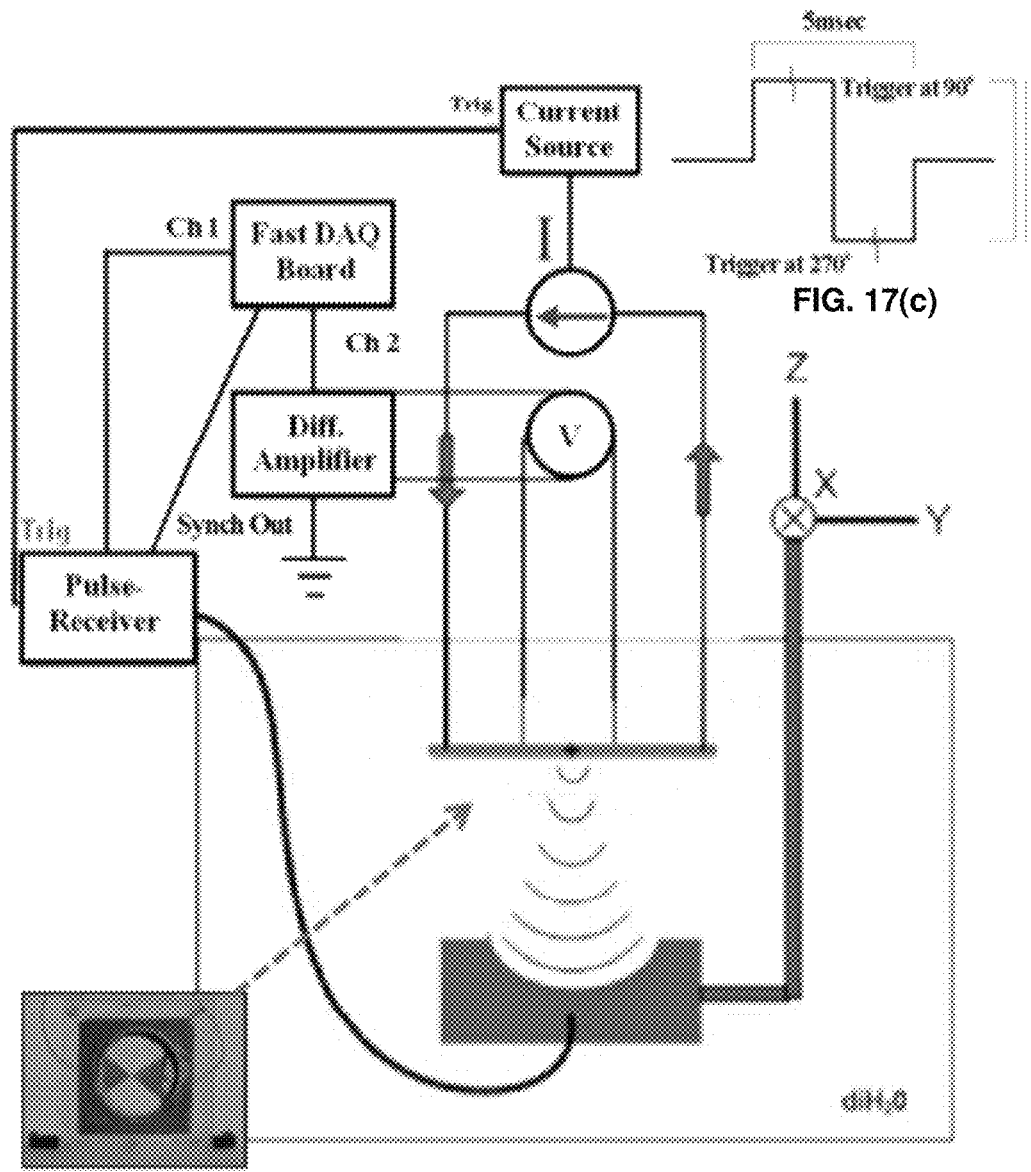

FIG. 17(a) is a schematic diagram of the experimental setup for evaluating hydrophones, as discussed in the fourth representative embodiment. A current source injected a 200-Hz rectangular waveform into the hydrophone. Acousto-electric signals were acquired at the maximum) (90° and minimum)(270° of the waveform (FIG. 17(c)).

FIG. 17(b) depicts a subject bowtie hydrophone.

FIG. 17(c) is a plot of the rectangular waveform of electrical current as injected into the hydrophone.

Figure 17D:
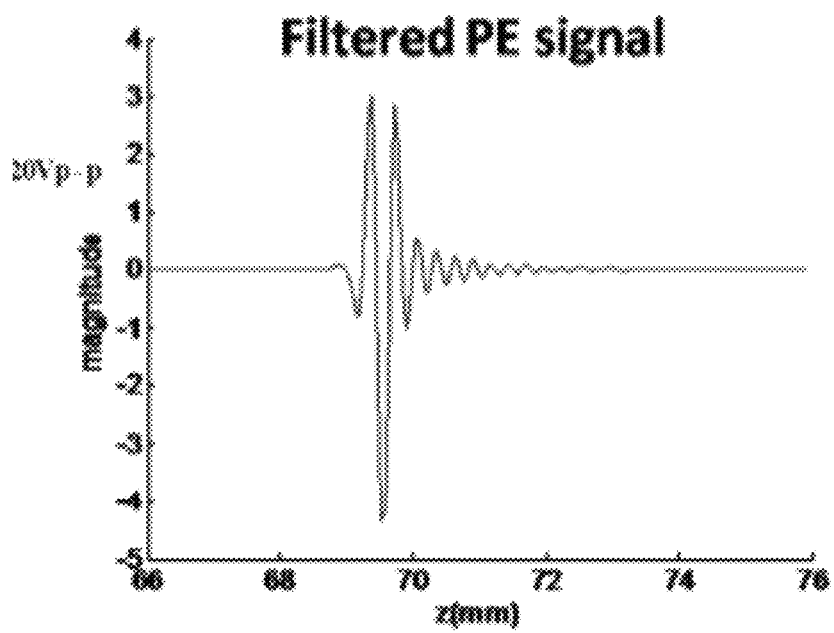

FIG. 17(d) is a plot of a typical pulse-echo signal produced by the hydrophone at the maximum and minimum of the current waveform.

Figure 17E:
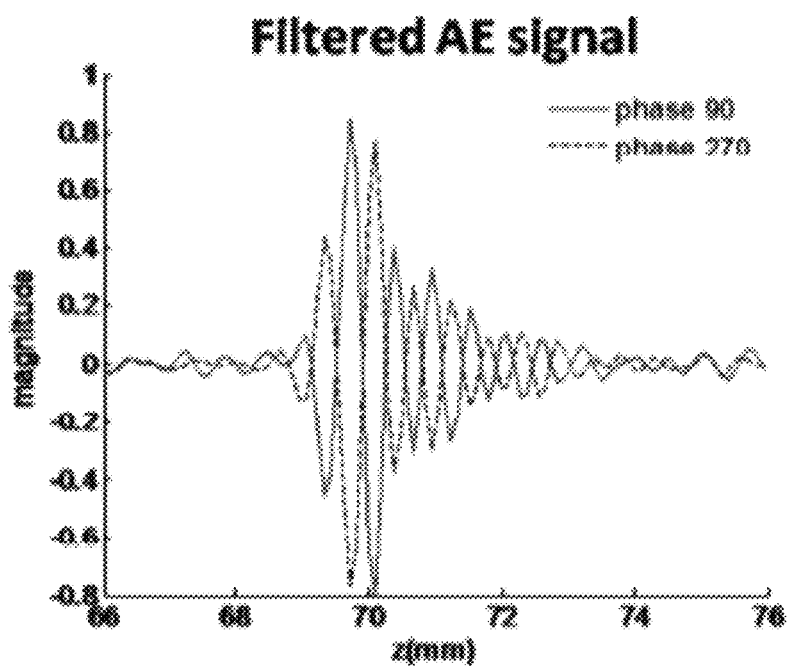

FIG. 17(e) is a plot of a typical acousto-electric signal produced by the hydrophone at the maximum and minimum of the current waveform. Common mode noise was reduced by subtracting acousto-electric signals having opposite phase.

Figure 18A:
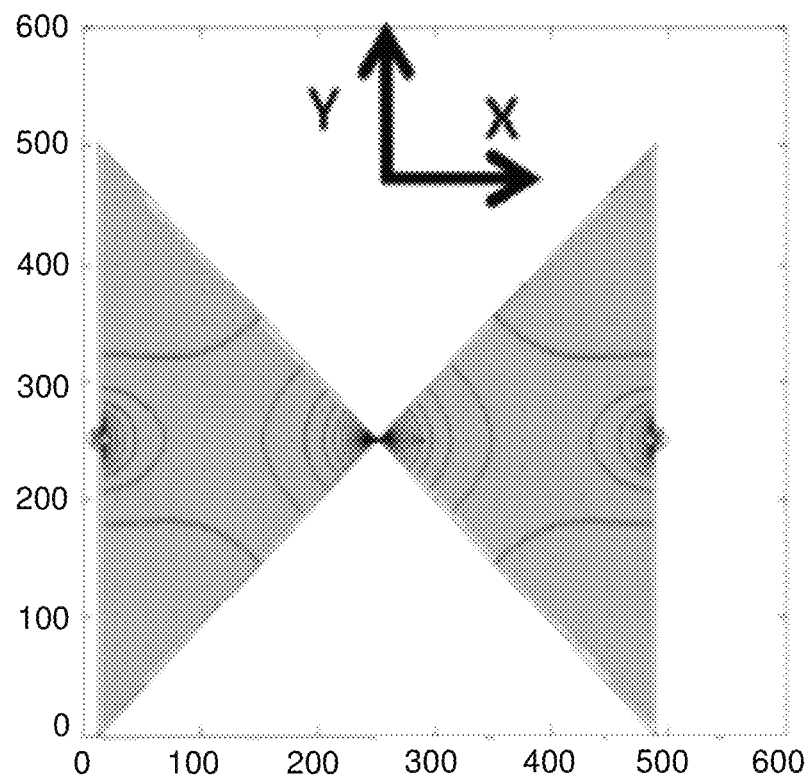

FIG. 18(a) shows the current distribution and electric field simulated by the conductive media DC application in the MATLAB partial differential equation toolbox, in which two electrodes are defined by Dirichlet boundary conditions, and the other two electrodes are defined by Neumann boundary conditions, as discussed in the fourth representative embodiment.

Figure 18B:
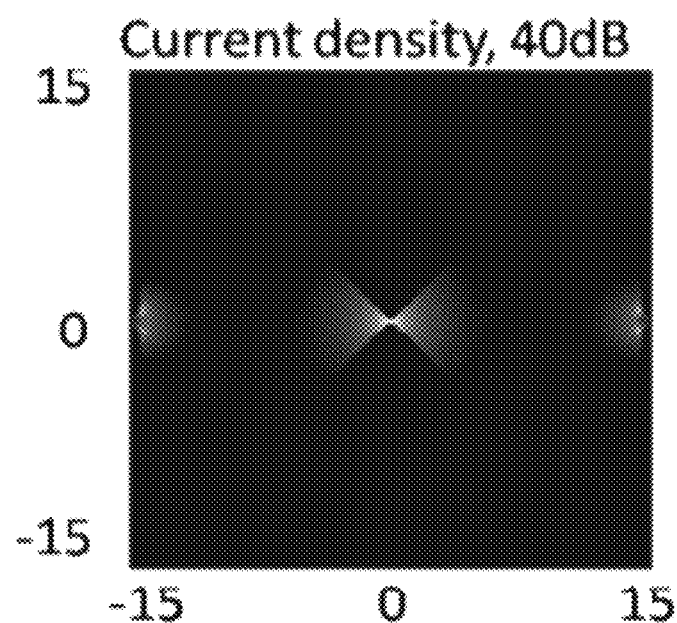

FIG. 18(b) shows the current-density distribution of the lead field as calculated based on the simulated potential in electric field and mesh information.

Figure 18C:
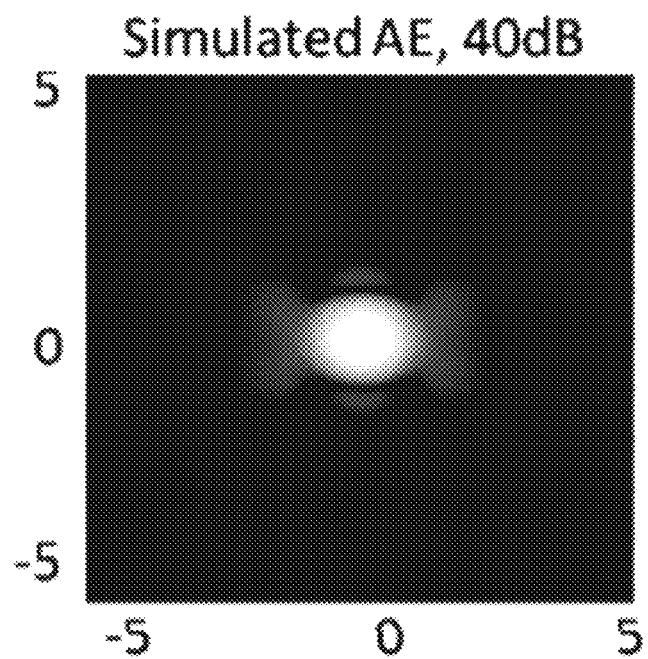

FIG. 18(c) shows a simulated AE envelope dB plot at the focus of the bowtie hydrophone, having a sensitivity zone of 200 μm×200 μm. The dimensional unit in FIGS. 18(b) and 18(c) is mm.

Figure 19:
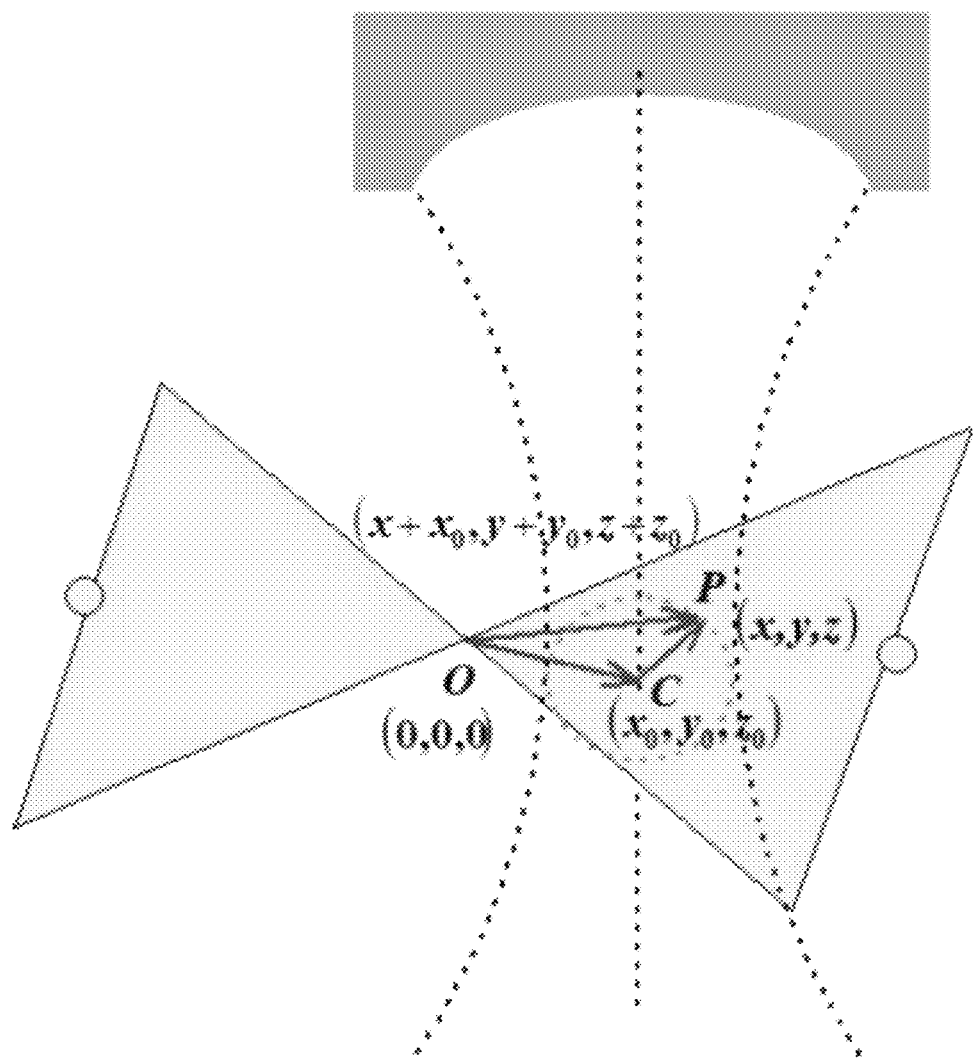

FIG. 19 is a schematic of the AE effect on the bowtie hydrophone, as discussed in the fourth representative embodiment. The coordinate center O(0, 0, 0) is at the center of the sensitivity zone. The transducer center is $C(x_0, y_0, z_0)$, and any point P in the ultrasound pressure field (x, y, z) can be described in the electric field as $(x+x_0, y+y_0, z+z_0)$.

Figure 20C:
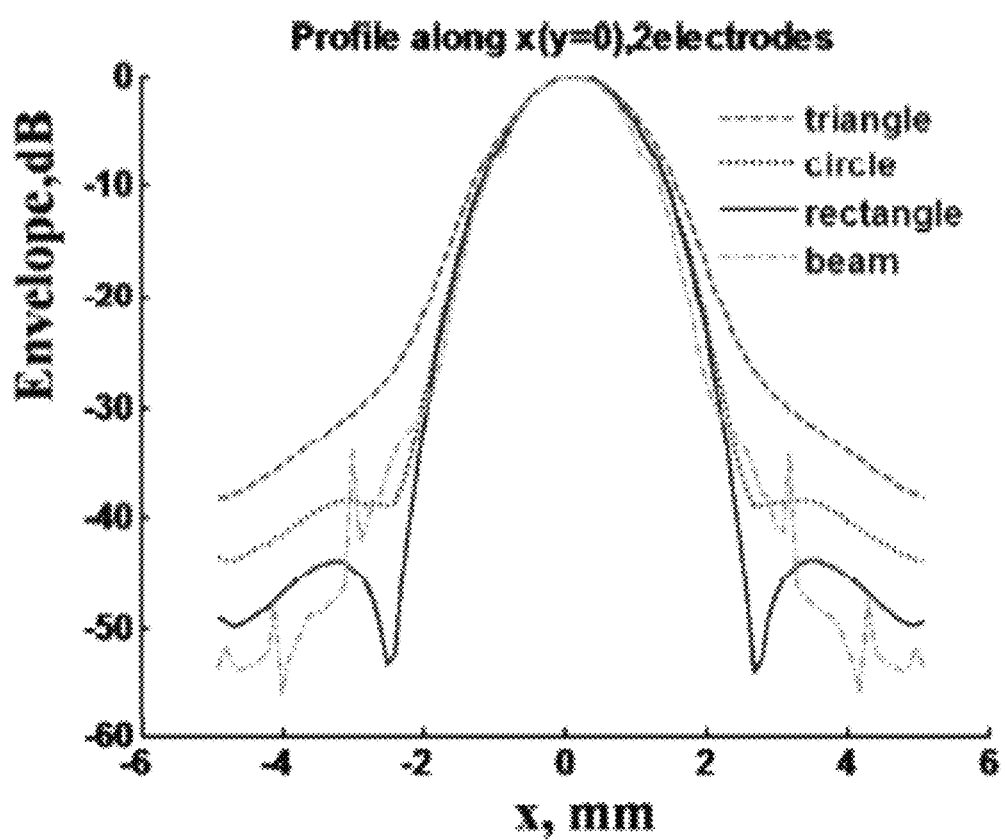
Figure 20D:
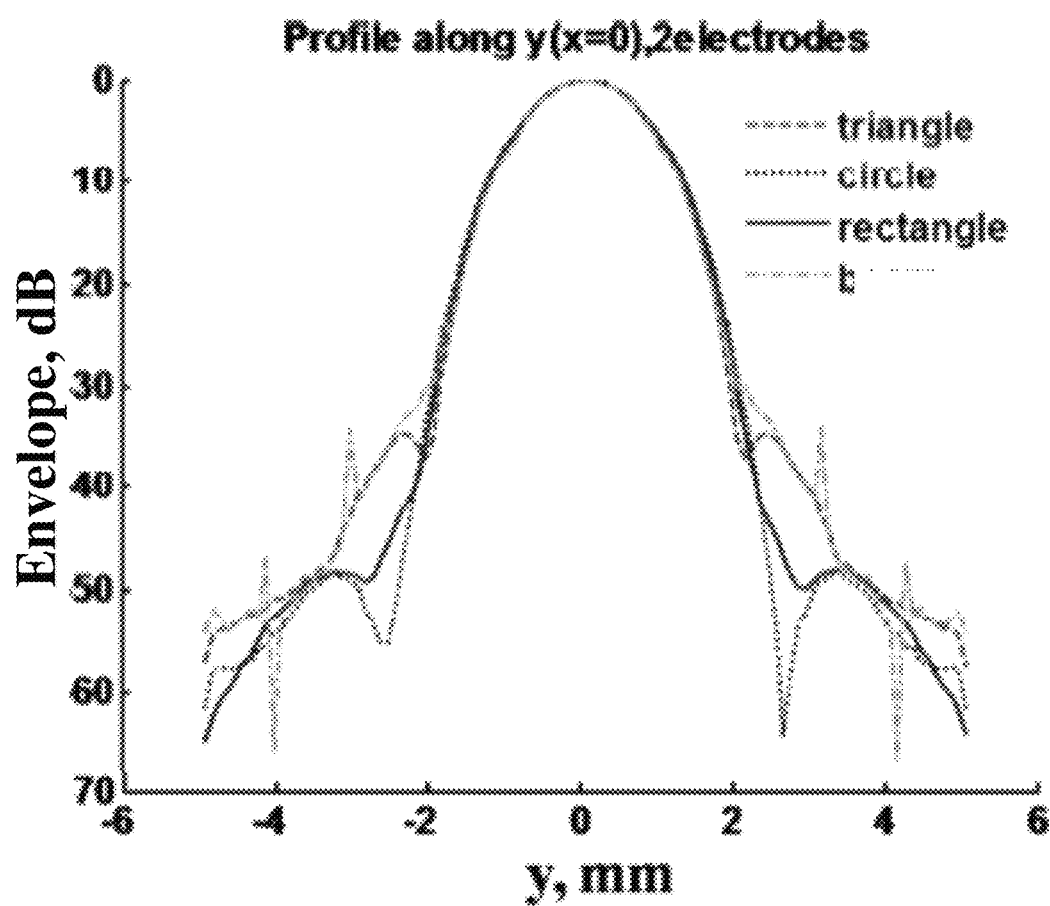

FIGS. 20(a)-20(d) depict simulation results obtained with hydrophones having different respective shapes, as discussed in the fourth representative embodiment. The three shapes are triangular bowtie, circular dumbbell, and rectangular dumbbell (FIG. 20(a)), each with a center area (sensitivity zone) of about 200 μm×200 μm. FIG. 20(b) shows respective simulated acousto-electric signals, along the x-y plane, at the focus for each hydrophone; FIG. 20(c) shows the acousto-electric profile at the center in the x-direction; and FIG. 20(d) depicts the center profile in the y-direction.

Figure 21A:
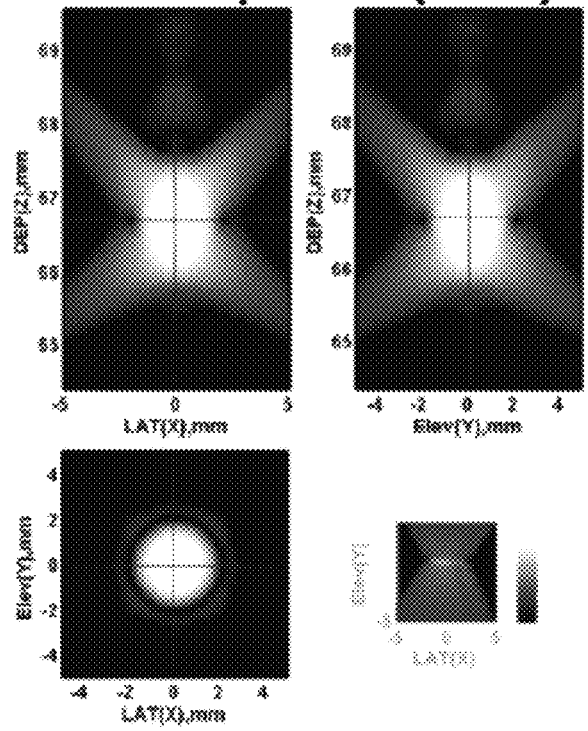
Figure 21B:
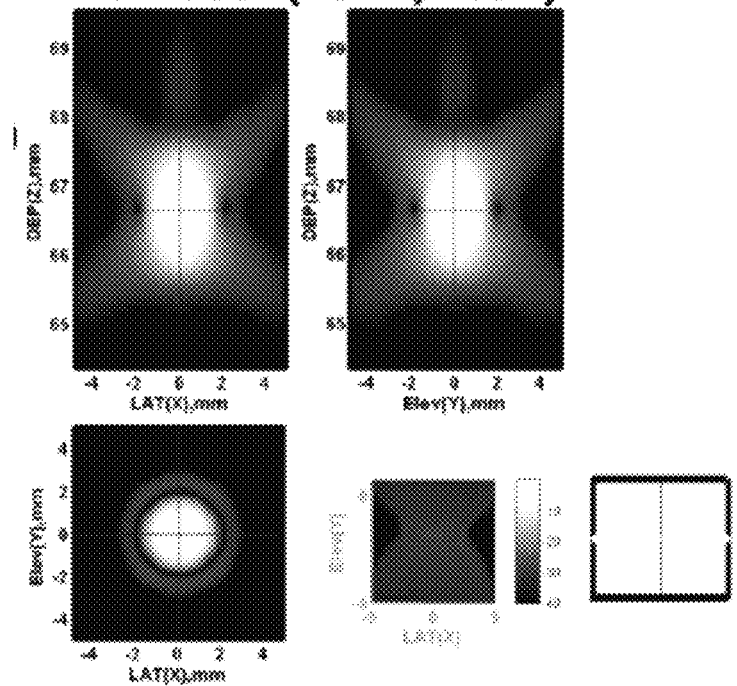
Figure 21C:
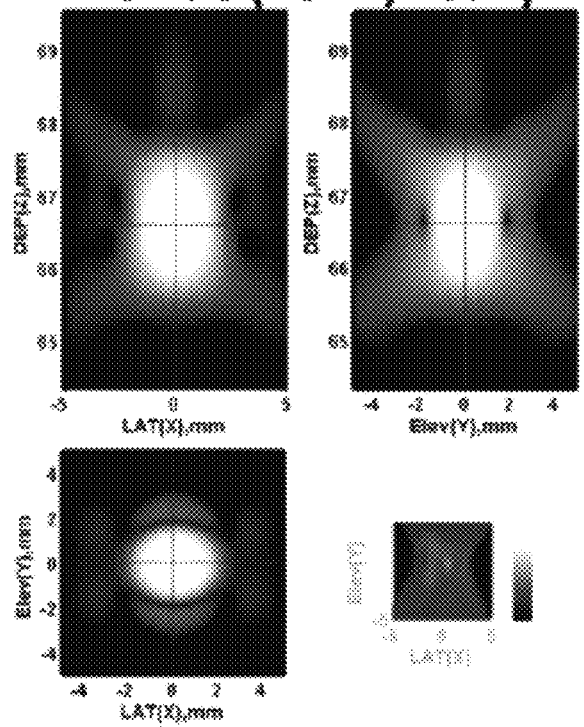
Figure 21D:
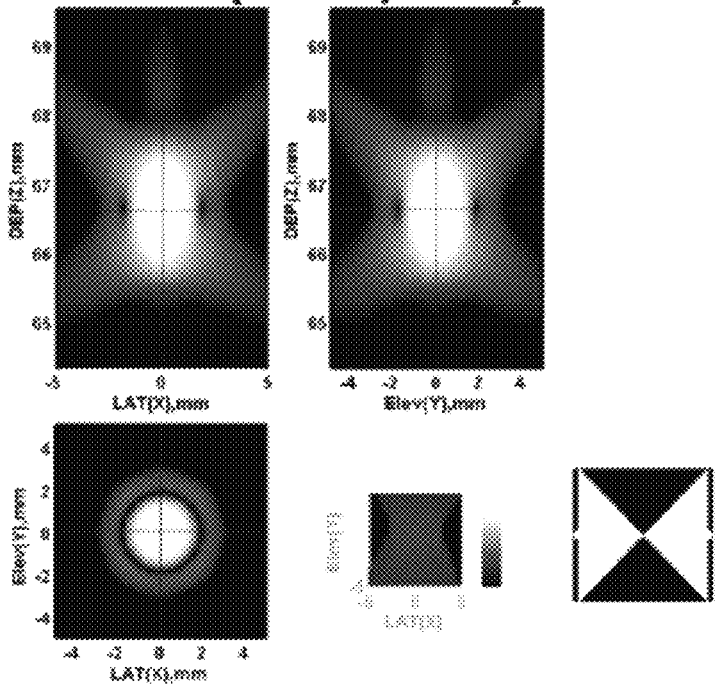

FIGS. 21(a)-21(d) are 3-D images of the cross-sectional 40-dB envelope of simulations discussed in the fourth representative embodiment. FIGS. 21(a)-21(c) show comparisons between the beam pattern (FIG. 21(a)), rectangular dumbbell at Rel=1 (FIG. 21(b)), bowtie at Rel=1 (FIG. 21(c)), and rectangular dumbbell at Rel=50 (FIG. 21(d)).

Figure 22A:
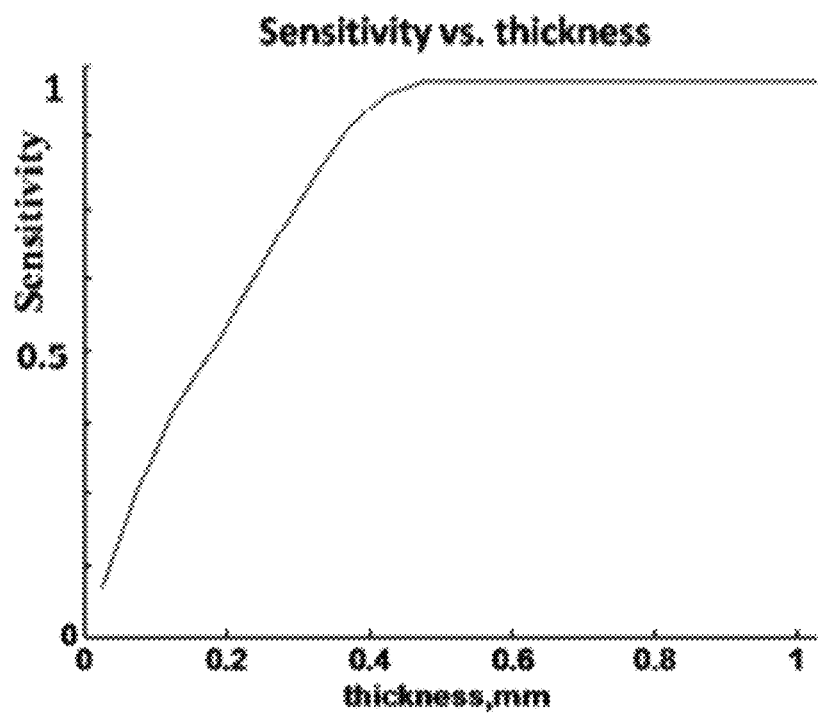

FIG. 22(a) is a plot of simulation data indicating that hydrophone sensitivity increases with thickness, up to more than half the wavelength of the transducer, beyond which sensitivity is substantially constant, as discussed in the fourth representative embodiment.

Figure 22B:
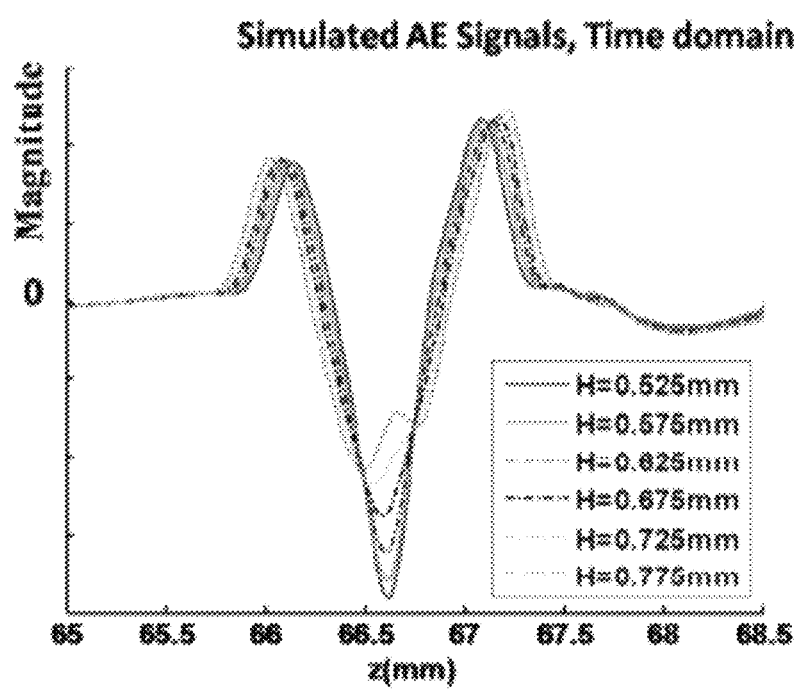

FIG. 22(b) is a plot of simulated acousto-electric A-lines at the center of the cross-section.

Figure 22C:
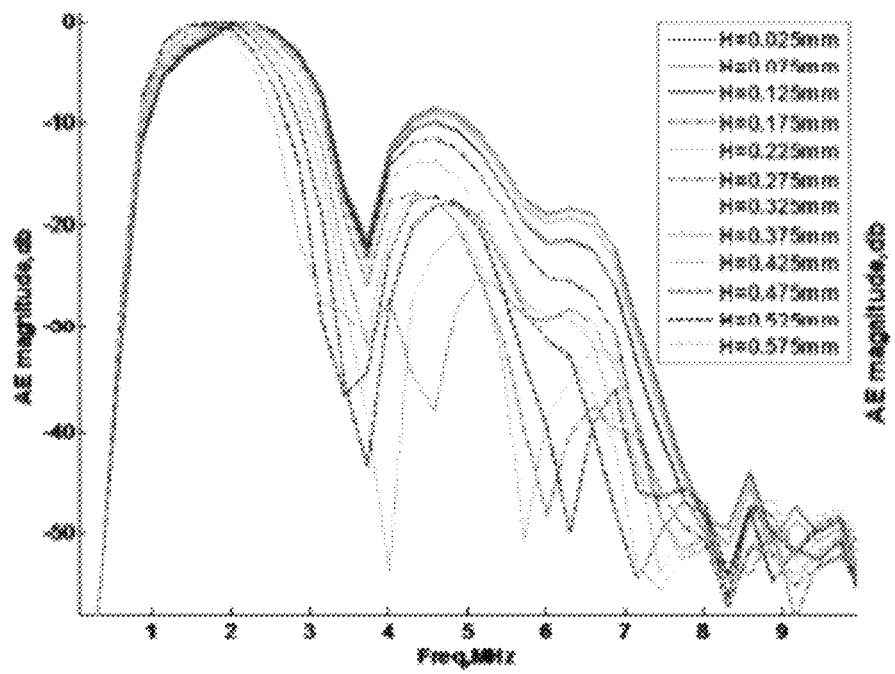

FIG. 22(c) is a plot of the spectrum of the simulated acousto-electric A-lines for thickness at about half wavelength.

Figure 22D:
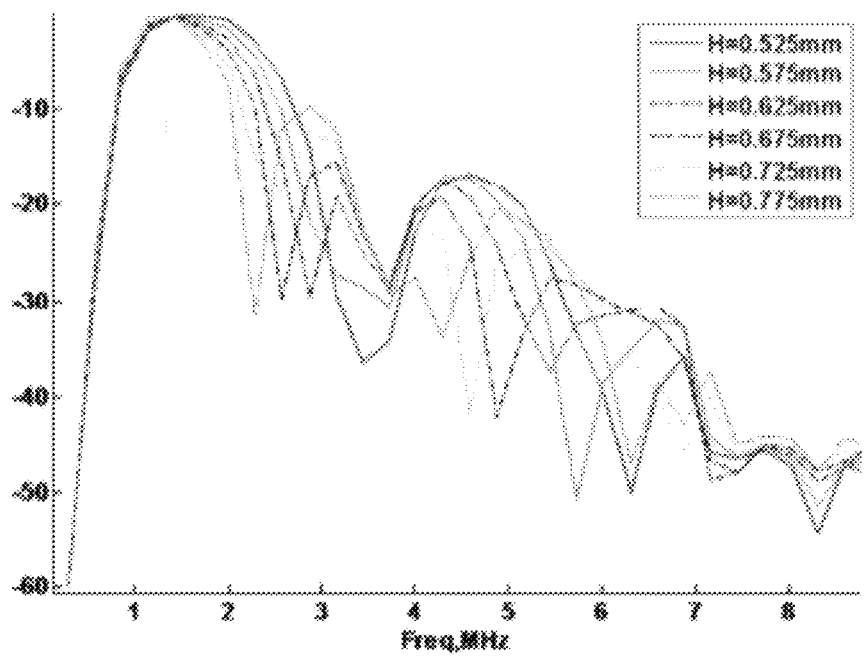

FIG. 22(d) is a spectrum of the simulated acousto-electric A-lines for thickness greater than half wavelength. The center frequency of the transducer is 2.25 MHz, and its wavelength is about 657 μm.

Figure 23A:
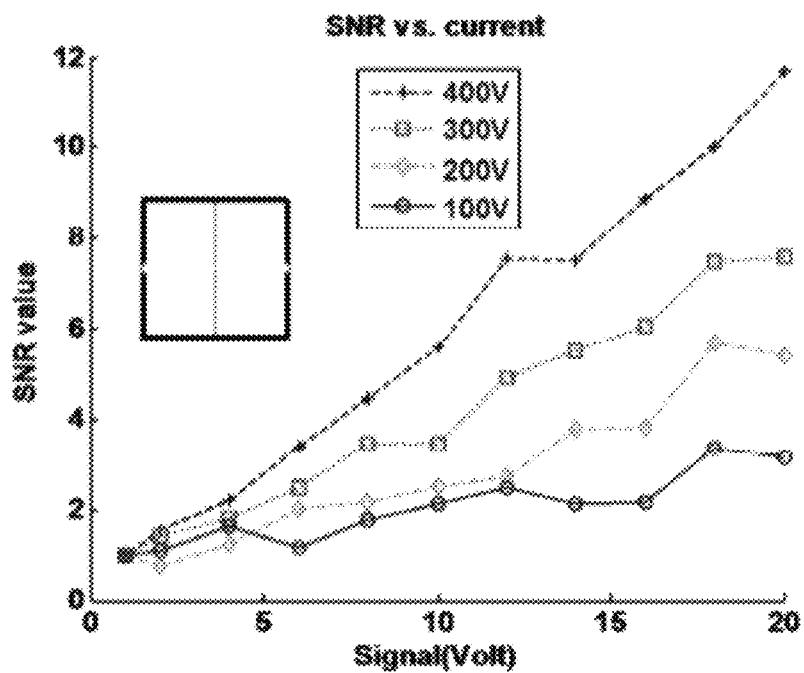
Figure 23B:
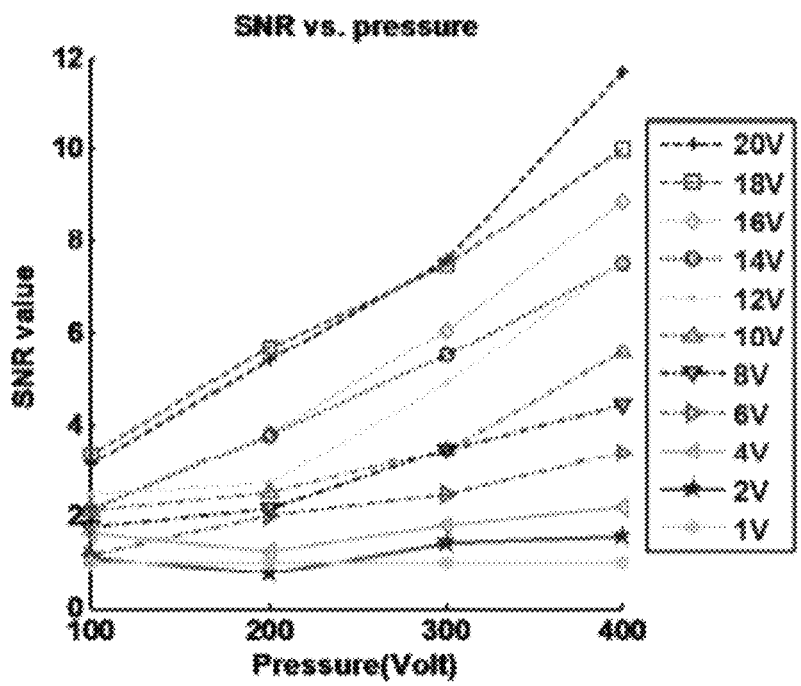

FIGS. 23(a) and 23(b) are plots of signal versus signal-to-noise (SNR) produced by a rectangular dumbbell hydrophone of the fourth representative embodiment. FIG. 23(a)

is a plot of SNR versus current at 100 V, 200 V, 300 V, and 400 V, and FIG. 23(b) is a plot of SNR versus pressure at various voltages.

Figure 24A:
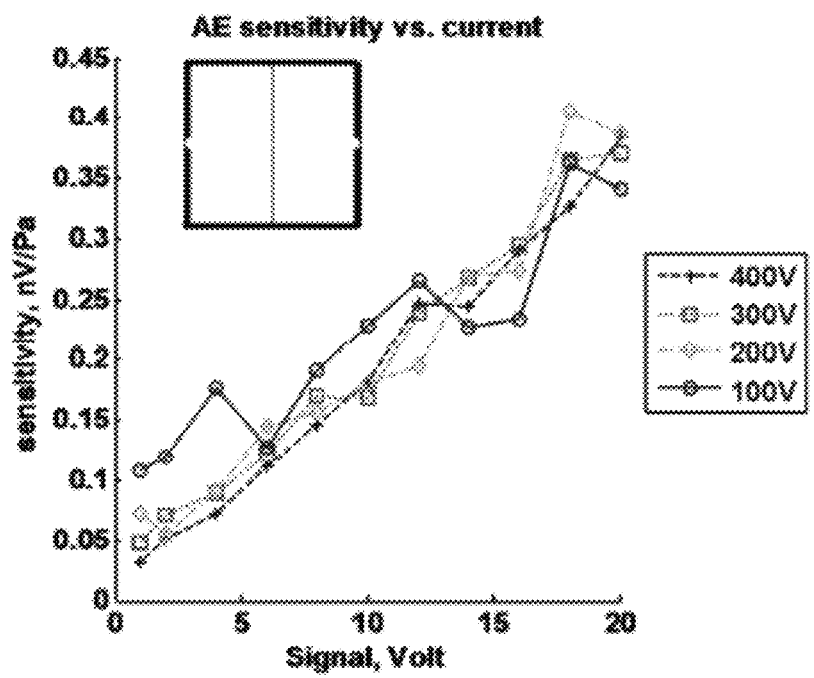
Figure 24B:
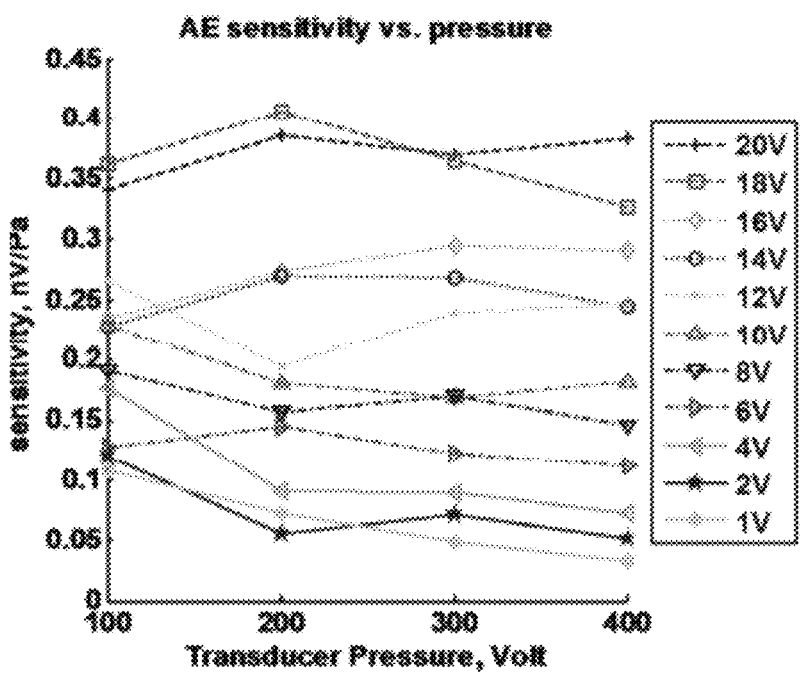
Figure 24C:
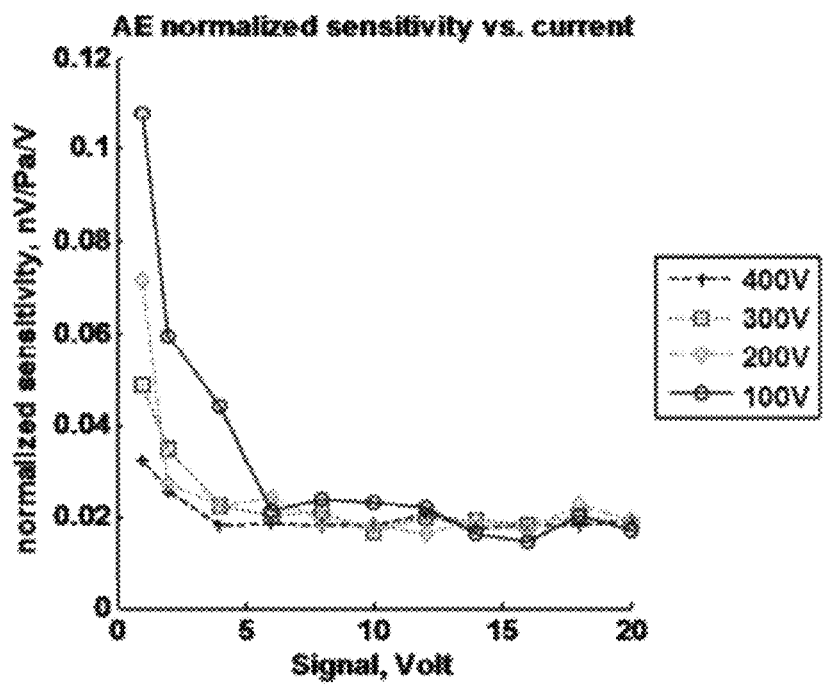
Figure 24D:
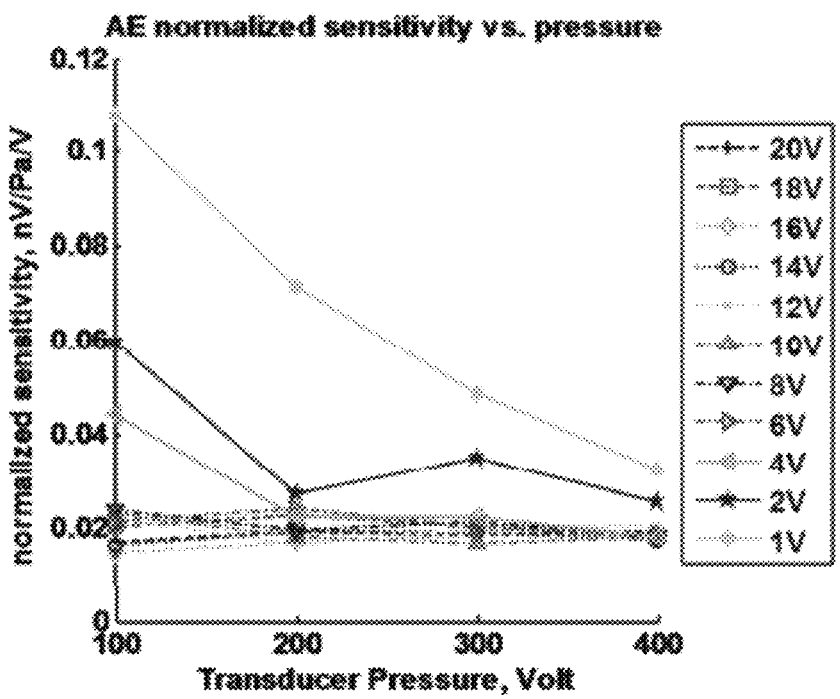

FIGS. 24(a)-24(b) are plots of sensitivity data, and FIGS. 24(c)-24(d) are plots of normalized sensitivity obtained with a dumbbell (Rel=1) hydrophone according to the fourth representative embodiment, showing the effects of injected current and transducer pressure.

Figure 25A:
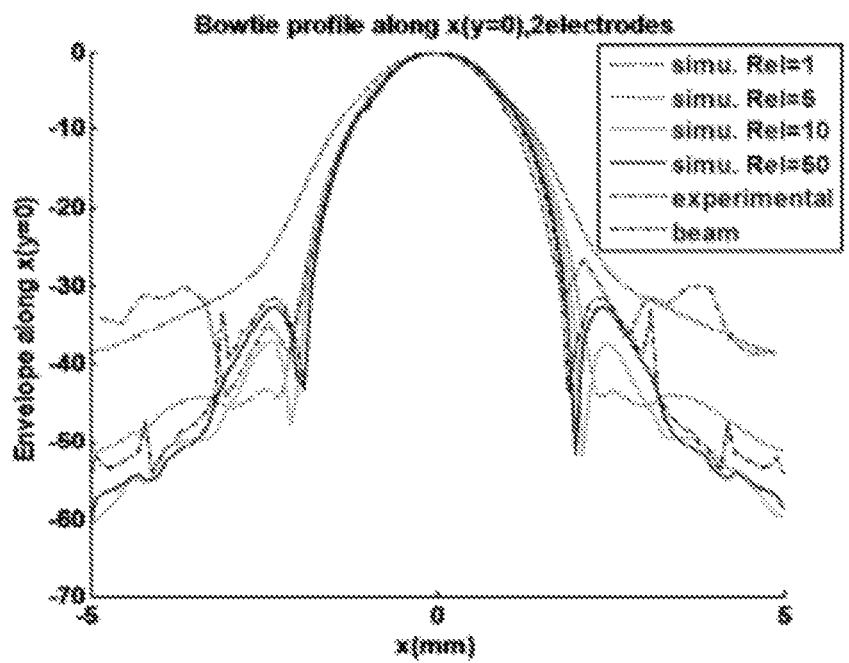
Figure 25B:
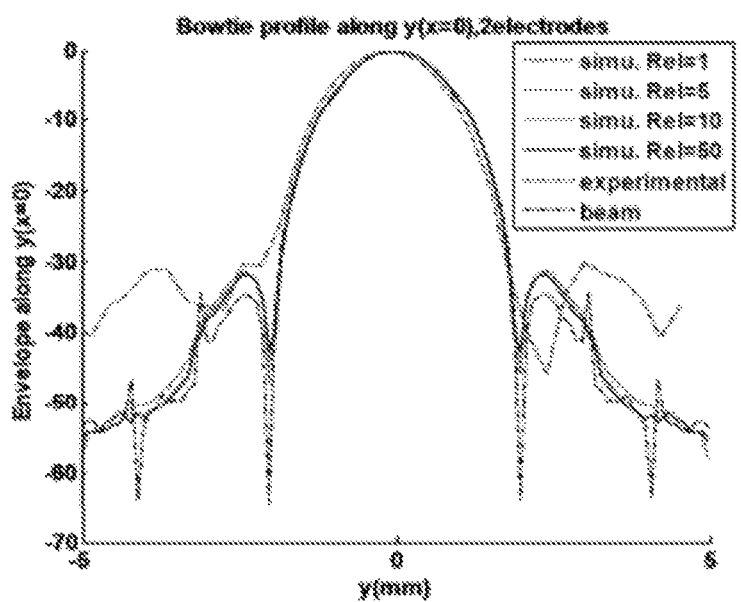
Figure 25C:
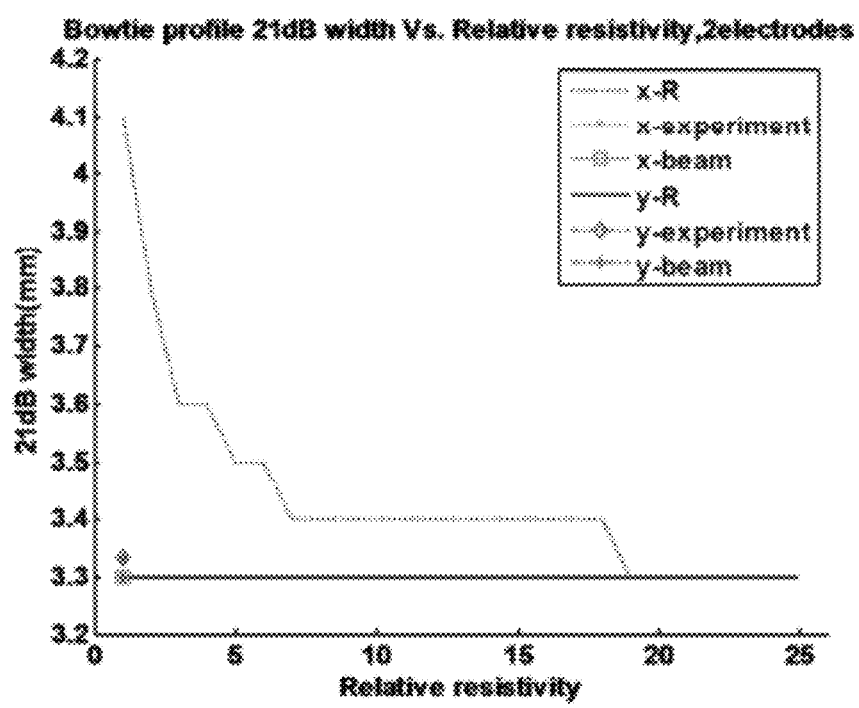

FIGS. 25(a)-25(c) depict the effects of the relative resistivity of ITO/gold (Au) over the AE bowtie hydrophone beam pattern. "Experimental" denotes a bowtie hydrophone with ITO in the sensitivity zone (200 μm×200 μm) center and gold in the remaining areas of the hydrophone. "Beam" denotes the transducer beam pattern on a focus simulated by FIELD II. "Simu. Rel" denotes simulated AE signals on the focus with different respective relative resistivities of ITO/Au. FIG. 25(a) shows an exemplary profile in the center, along the x-direction. In FIG. 25(b), each profile of simulated AE signals with different respective Rel values has almost the same shape as the transducer "beam" pattern along the y-direction. FIG. 25(c) shows a determination of the lowest relative resistivity of ITO/Au that can produce an ideal or experimental result.

Figure 26:
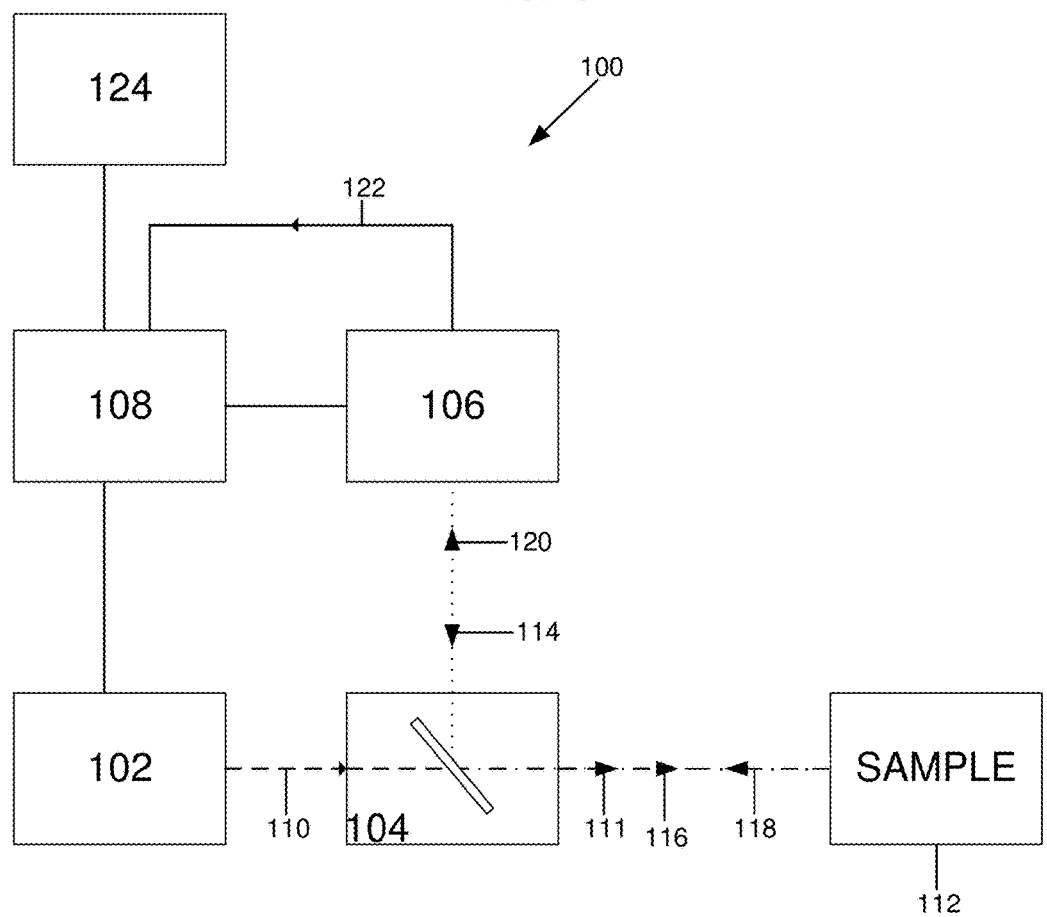

FIG. 26 schematically depicts a general configuration of an imaging device according to the invention.

Figure 27A:
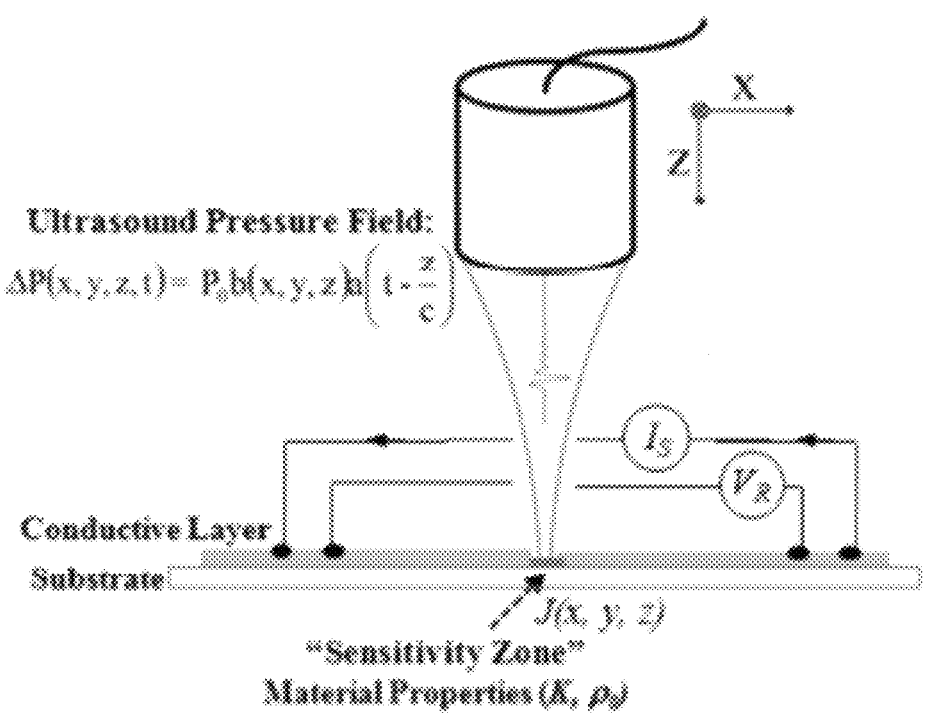

FIG. 27(a) is a schematic diagram of an acousto-electric hydrophone usable with an imaging device as disclosed herein. Depicted are the ultrasound pressure field, the sensitivity zone, and connections to electrical current.

Figure 27B:
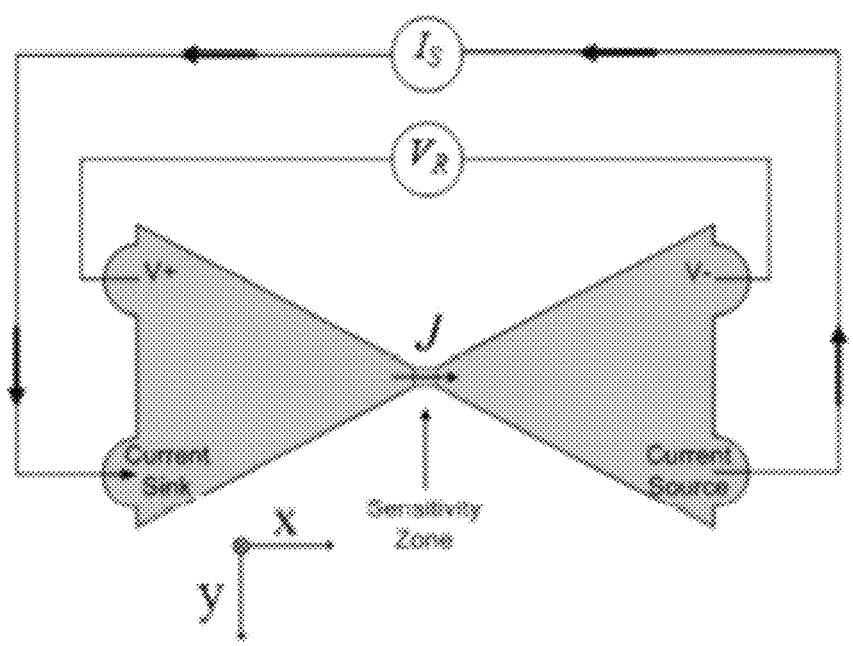

FIG. 27(b) is a schematic diagram including a plan view of the hydrophone shown in FIG. 27(a), as connected to electrical current. AE signals produced by the hydrophone are detected at $V_R$.

FIG. 28 is an optical diagram of the optical system discussed in Example 5.

FIG. 29 is an image of the optical chamber of the embodiment discussed in Example 5.

Figure 30:
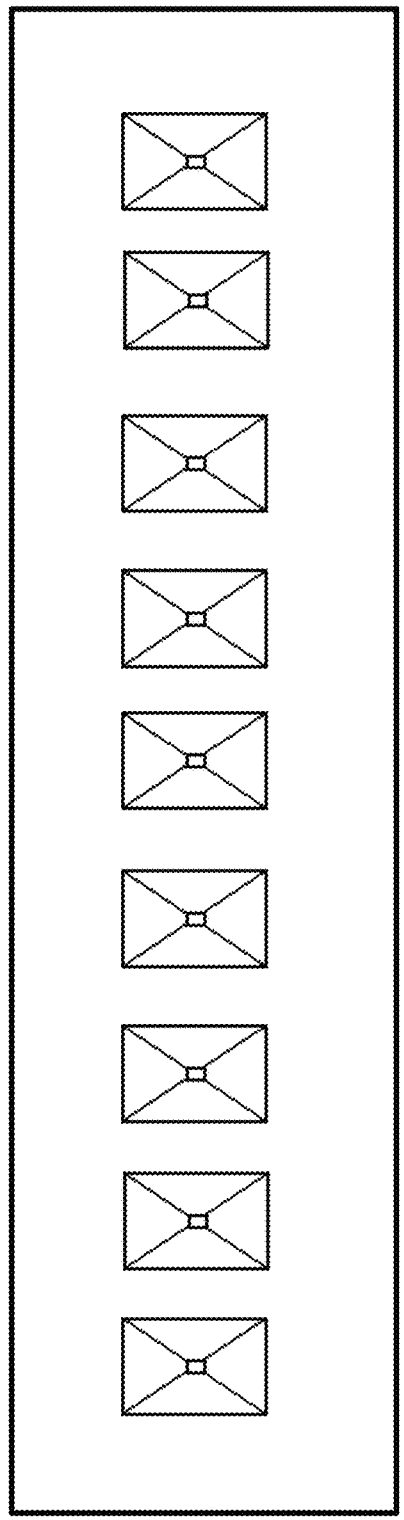
Figure 31A:
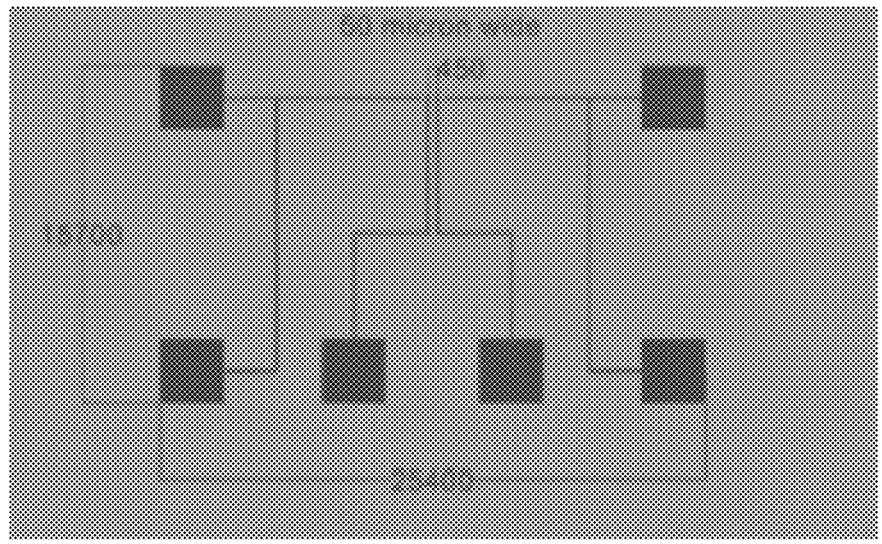
Figure 31B:
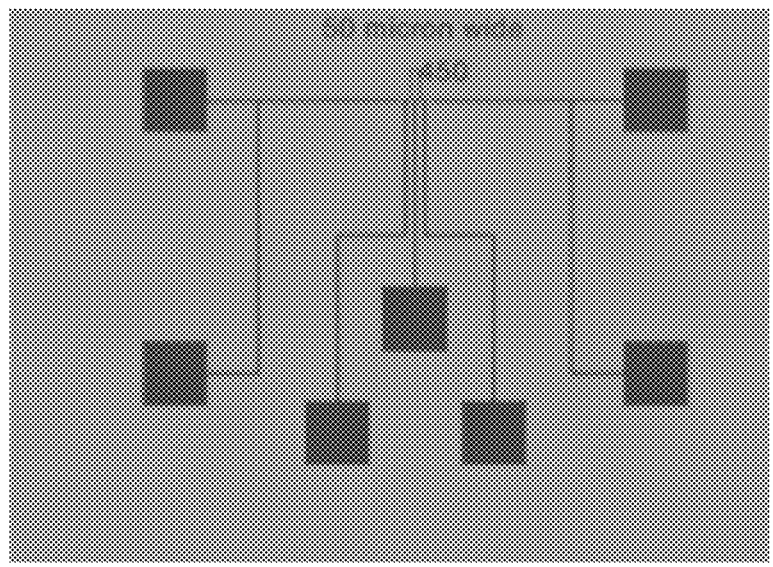
Figure 31C:
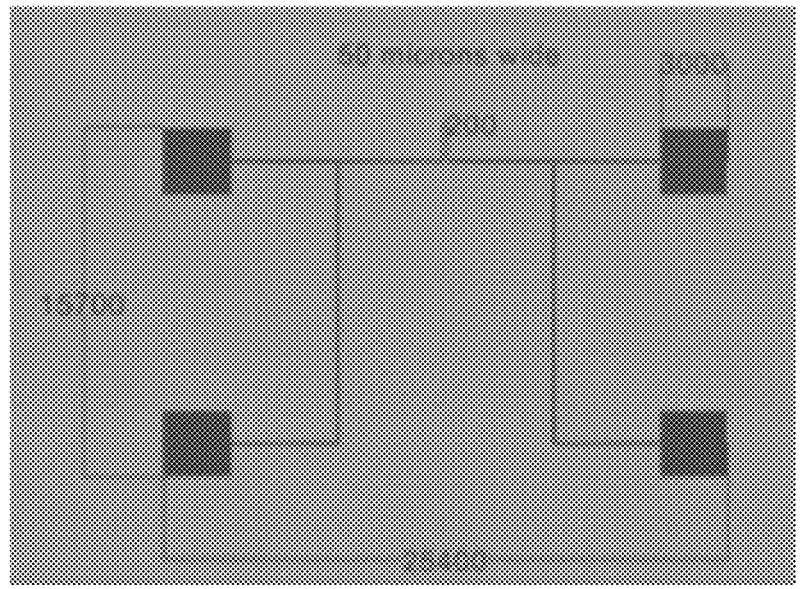
Figure 31D:
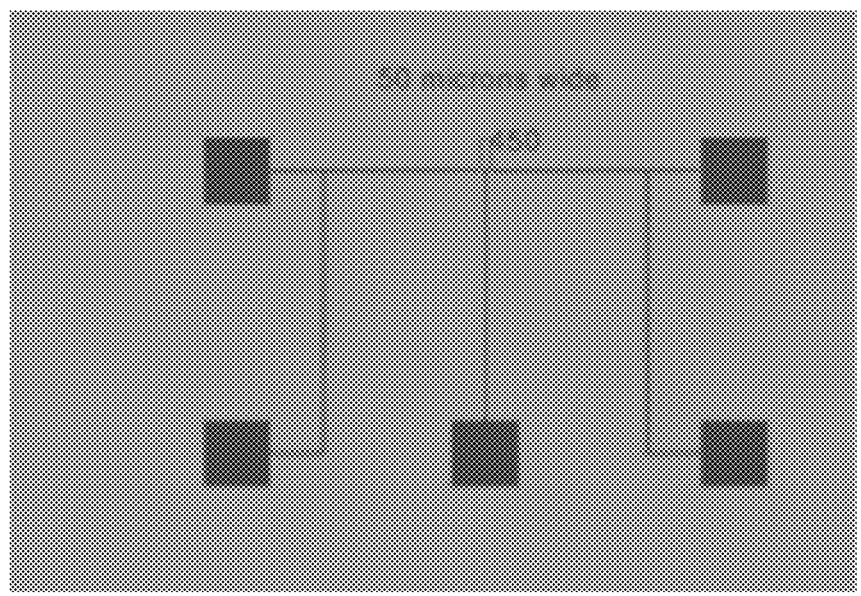

FIG. 30 depicts an exemplary linear (1-D) array of detectors (e.g., hydrophones) usable with any of various embodiments of an imaging device.

FIGS. 31(a)-31(d) depict respective exemplary 2-D arrays of detectors.

Figure 32A:
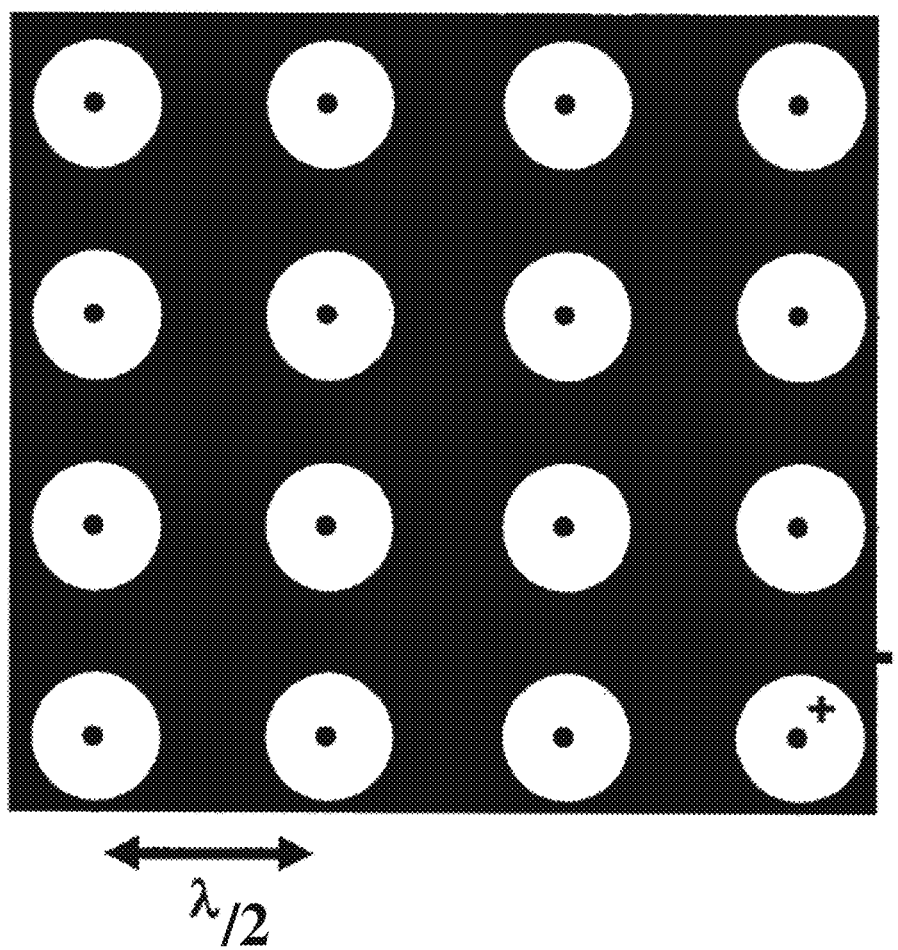

FIG. 32(a) is a schematic diagram of an embodiment of a planar (2-D) detector array comprising sixteen individual acousto-electric detectors, as discussed in the fifth representative embodiment. The incident ultrasonic waves are perpendicular to the page.

Figure 32B:
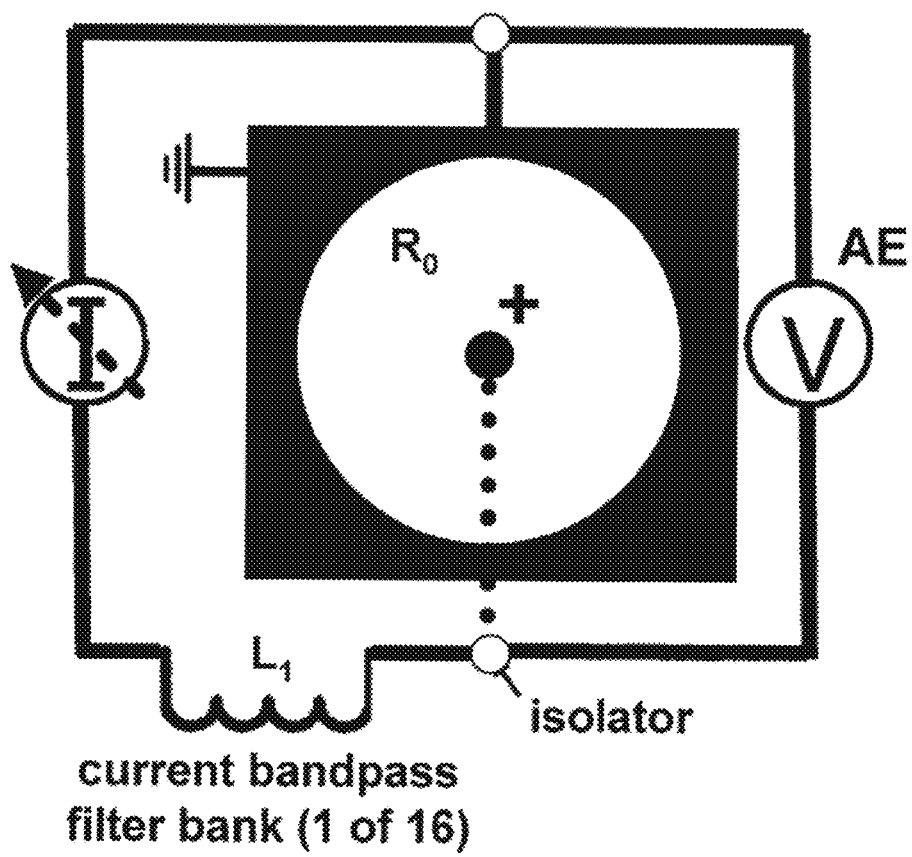

FIG. 32(b) depicts the electrical connections for each detector in FIG. 32(a).

Figure 33A:
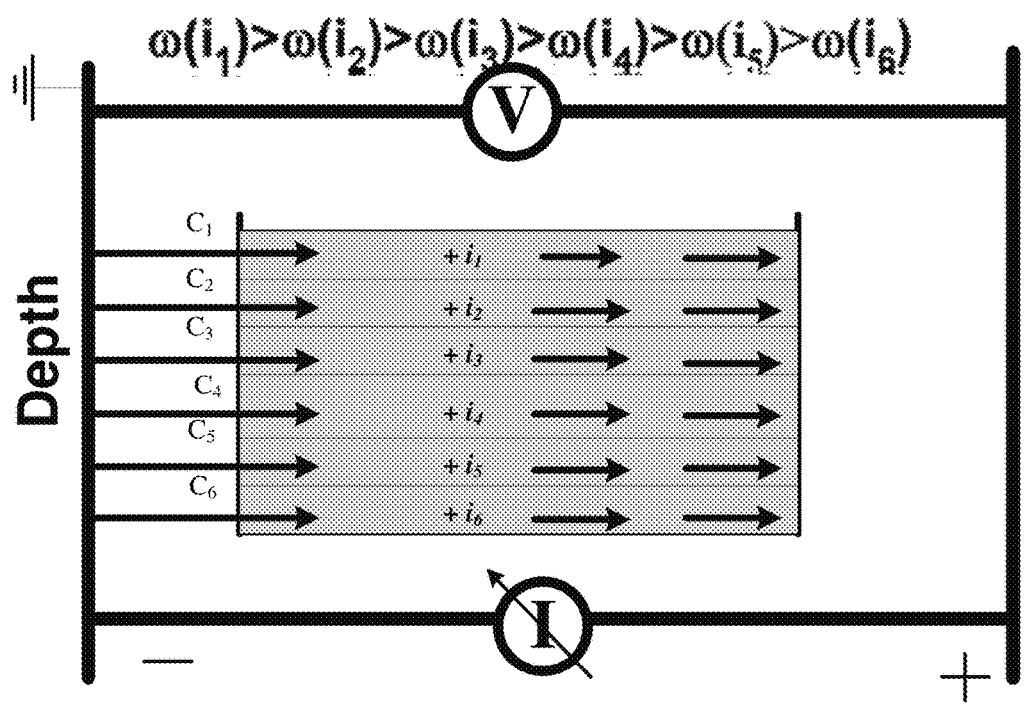

FIG. 33(a) depicts an embodiment of a 3-D array of ultrasonic detectors, as discussed in the fifth representative embodiment. Current frequency is encoded according to layer.

Figure 33B:
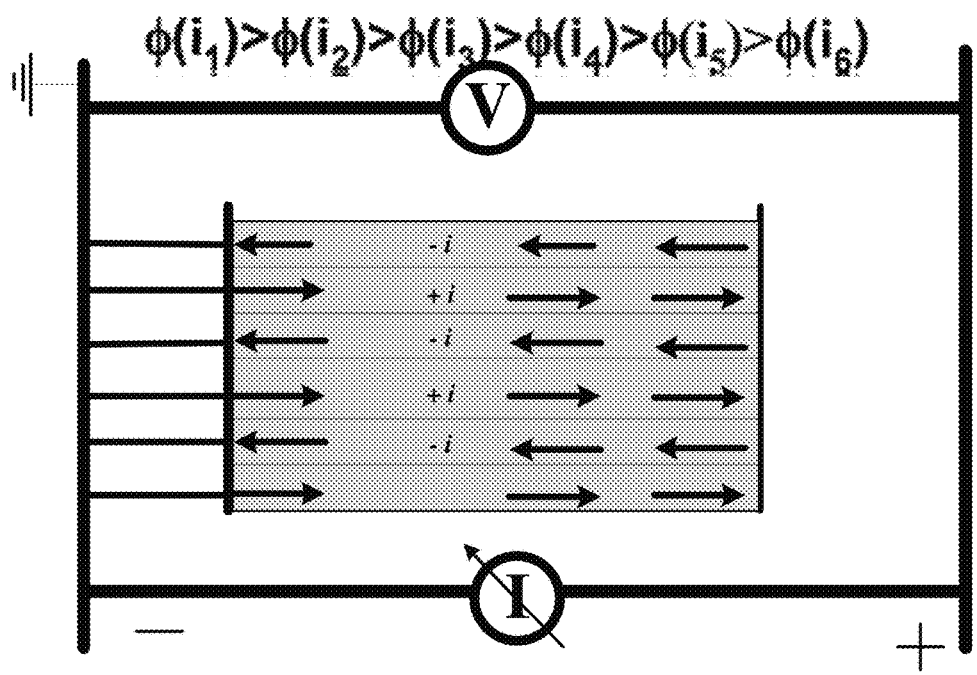

FIG. 33(b) depicts the array of FIG. 33(a), in which current phase is encoded according to layer.

Figure 34:
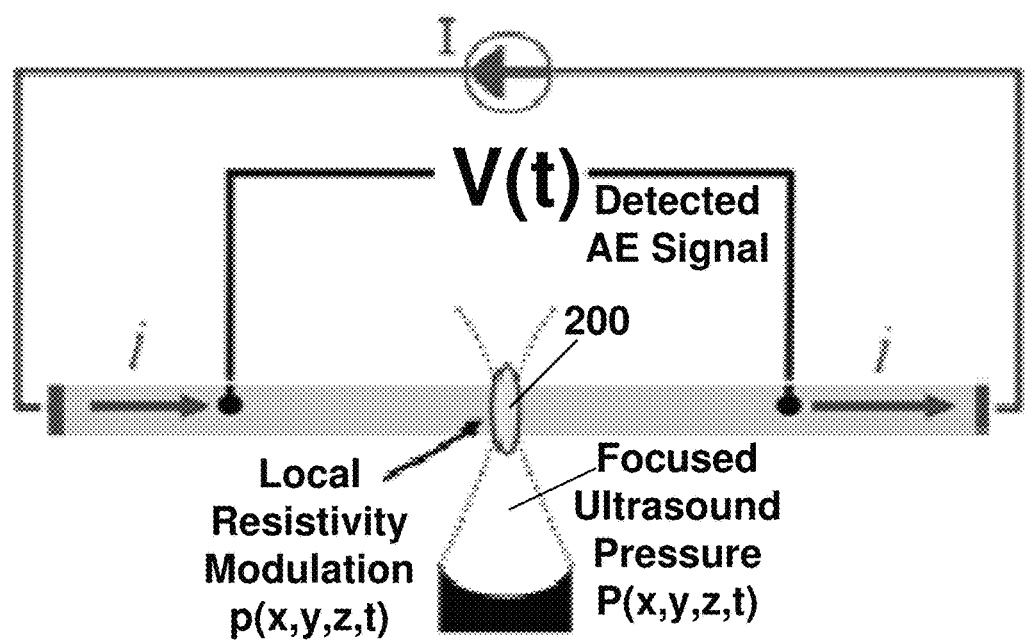

FIG. 34 is a schematic diagram of the acousto-electric effect that is the operational basis of certain ultrasonic detectors utilized in the subject imaging devices.

Figure 35:
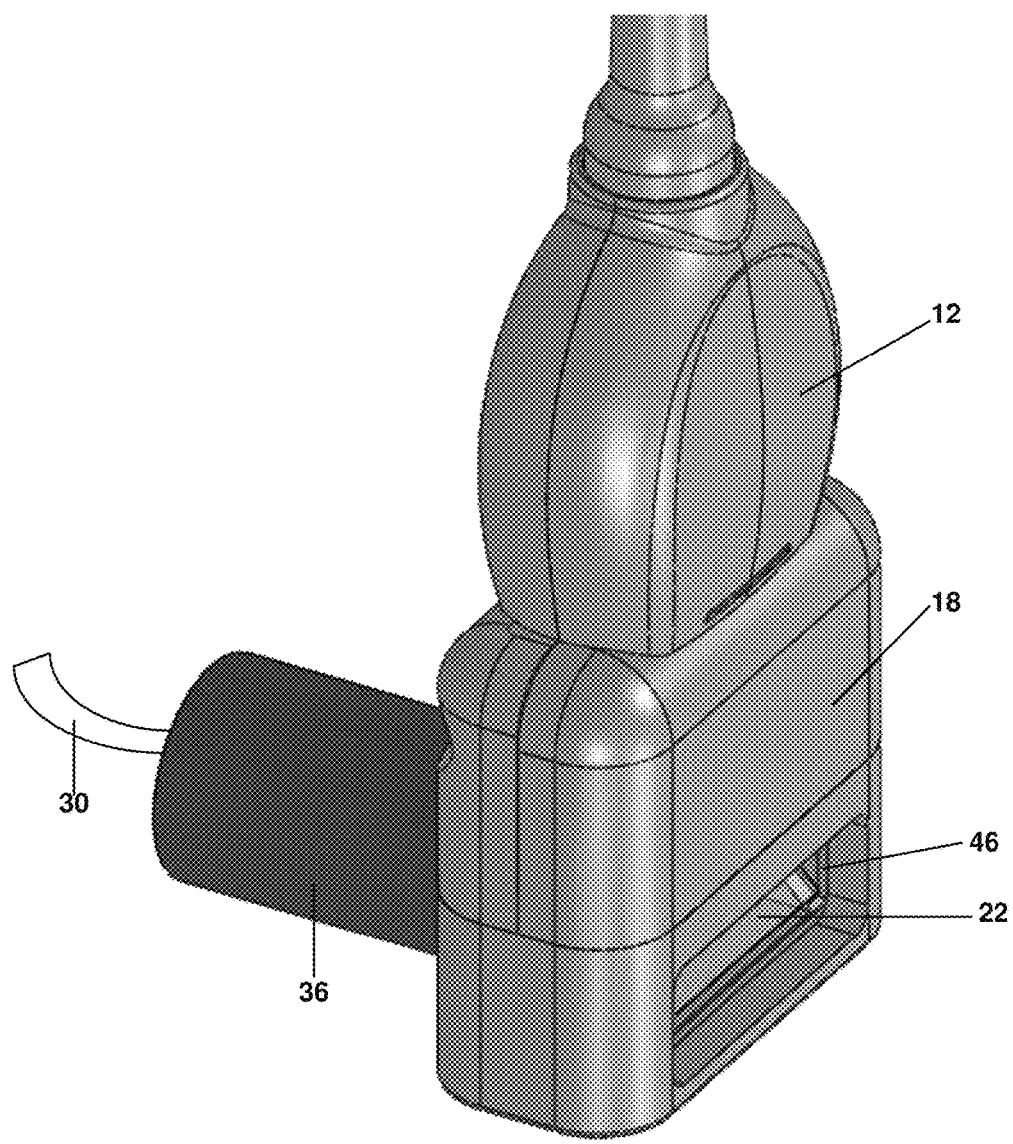

FIG. 35 is a perspective view of the first representative embodiment.

FIGS. 36(a) and 36(b) are images obtained using a microscope slide as the US reflector 12, as described in Example 1. The images are of a cross-section of a 127-μm thick Teflon blue wire. FIG. 36(a) shows features down to −35 dB, at which beam-forming artifacts and noise can be seen. FIG. 36(b) shows signals about the FWHM. Both figures show close co-registration of the PE data with the PA data. The figures were plotted on exactly the same scales. The symmetrical characteristic of these images illustrates the accurate imaging capability of this embodiment.

DETAILED DESCRIPTION

The following disclosure is presented in the context of representative embodiments that are not to be construed as being limiting in any way. This disclosure is directed toward all novel and non-obvious features and aspects of the various disclosed embodiments, alone and in various combinations and sub-combinations with one another. The disclosed methods, apparatus, and systems are not limited to any specific aspect or feature or combination thereof, nor do the disclosed embodiments require that any one or more specific advantages be present or problems be solved.

Although the operations of the disclosed methods are described in a particular, sequential order for convenient presentation, it should be understood that this manner of description encompasses rearrangement of the operations, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other things and methods.

This disclosure sometimes uses terms like "produce," "generate," "select," "receive," "exhibit," and "provide" to describe the disclosed methods. These terms are high-level abstractions of the actual operations that are performed. The actual operations that correspond to these terms may vary depending on the particular implementation and are readily discernible by one of ordinary skill in the art.

The singular forms "a," "an," and "the" include the plural forms unless the context clearly dictates otherwise. The term "includes" means "comprises." Unless the context dictates otherwise, the term "coupled" means mechanically, electrically, or electromagnetically connected or linked and includes both direct connections or direct links and indirect connections or indirect links through one or more intermediate elements not affecting the intended operation of the described system.

Certain terms may be used such as "up," "down," "upper," "lower," and the like. These terms are used, where applicable, to provide some clarity of description when dealing with relative relationships. But, these terms are not intended to imply absolute relationships, positions, and/or orientations.

The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about" or "approximately." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

The following explanations of terms are provided to better describe the present disclosure and to guide those of ordinary skill in the art in the practice of the present disclosure.

The "acousto-electric effect" (AE effect) is based upon interactions of a propagating acoustic wave with charged particles in a conductive material situated at a location where the acoustic wave is incident. More specifically, the AE effect is based upon the acousto-electric equation:

$$\frac{\Delta \rho}{\rho_0} = -k\Delta P \quad (1)$$

where $\rho_0$ is initial electrical resistivity of a conductive material, $\Delta \rho$ is change in resistivity, P is pressure of the incident acoustic wave, and k is an interaction constant. See FIG. 34, in which acoustic pressure P(x, y, z, t) is focused on a conductive location 200 across which an electrical current I is passed. By Ohm's Law, as the electrical current is passing through the location 200, and as the location experiences the acoustic pressure, the location experiences a local resistivity modulation ρ(x, y, z, t). The resistivity modulation is proportional to the electrical current density in the material, and the resistivity changes are proportional to the corresponding pressure changes. The resistivity change is detected as an AE signal V(t).

The "acousto-optical (AO) effect" pertains to a relationship of a change in index of refraction of a material to a change in stress on the material using an acoustic wave incident on the material. As the incident acoustic wave applies pressure on the material, the index of refraction of the material changes in response to the applied pressure. The change in refractive index, in turn, changes the focal length of the material, which can correspond to a change in image size produced by a beam of light passing through the material. The change in image size can be detected using a fixed detector and quantified. The irradiance (energy per unit area) on the detector changes in response to the incident acoustic waves.

A "hydrophone" is a sensor or detector of acoustic waves, typically ultrasonic waves. Most hydrophones comprise a piezoelectric transducer that produces electrical pulses in response to pressure pulses, associated with ultrasonic waves, incident on the transducer. A hydrophone can be used for detection of ultrasonic waves propagating through various media, such as water or living tissue. Many hydrophones can detect sound waves propagating through air, but for best performance in detecting sound waves propagating through tissue (which contains a large amount of water), the hydrophone desirably is impedance-matched to the water in the tissue (which is denser than air). A poor acoustic impedance match typically reduces sensitivity of the hydrophone.

"Photoacoustic Imaging" (PAI) is an imaging technique exploiting the photoacoustic effect. The photoacoustic (PA) effect has been known since 1880, when Alexander Graham Bell observed the creation of acoustic waves in and by a sample being exposed to pulses of light. Nowadays, the light pulses are usually produced by a laser that can concentrate the pulses onto a small region in the sample. The resulting intermittent heating of the region exposed to the light pulses causes the material in the region to expand and contract. The resulting oscillatory motion of the exposed region generates acoustic waves that propagate through the sample and can be detected and interpreted to form an image using the same principle underlying ultrasonic imaging. The ultrasound image is based on optical absorption. Three-dimensional imaging is possible, with excellent tissue penetration. This technique is capable of high spatial resolution and exhibits high sensitivity.

A "piezoelectric" material is a material that, whenever acoustic or pressure waves propagate through the material, produces a corresponding voltage signal that can be processed. Conversely, whenever a piezoelectric material is electrically stimulated, it produces a corresponding acoustic wave.

"Pulse echo" (PE) imaging (also termed "ultrasonic imaging" and "ultrasound imaging") is an imaging technique using ultrasonic waves. The ultrasonic waves are delivered into a sample, and the returning signal is measured. Both can be achieved using a single ultrasonic transducer that converts input electrical pulses to ultrasonic waves sent into the sample and that converts ultrasonic waves returning from the sample into respective electrical pulses. More than one transducer can be used for both sending and receiving, and/or one transducer can be utilized for sending and another can be utilized for receiving ultrasonic waves. Further alternatively, multiple transducers (usually arranged in a defined array) can be used for receiving ultrasonic waves. Portions of the ultrasonic waves sent from the transducer are reflected from layers between different tissues, particularly wherever there are density changes in the sample. Reflected waves are converted by a receiving transducer into respective electrical pulses. The distance between a receiving transducer and a situs in the sample (at which the ultrasonic waves are incident) can be determined from data concerning total elapsed time between the moment the ultrasonic signal was sent and the moment it returned as a reflected wave to the transducer. The density of an object can be determined from the intensity of the returning ultrasonic wave. These two factors (time and intensity) are usually all that are needed to produce an ultrasound image.

"Resistivity" is a measure of the strength with which a material opposes the flow of electrical current. A material having low resistivity readily allows flow of electrical charges (current). Resistivity (ρ) defined by ρ=E/J, where ρ is the static resistivity (Ω·m), E is the magnitude of the electric field (V/m), and J is the magnitude of the current density (A/m$^2$). Most resistors and conductors have a uniform cross-section exhibiting a uniform flow of electric current, in which case $$\rho = R\frac{A}{\ell},$$

where R is the electrical resistance (Ω) of a unit of the subject material, l is the length of the unit of material, and A is the area of the cross-section of the unit of material. Electrical resistivity is the inverse of the electrical conductivity (σ) of the material: ρ=1/σ.

"Ultrasonic Detector" (also termed "ultrasound detector") is a detector sensitive to ultrasonic waves such that an input ultrasonic wave produces a corresponding electrical pulse or signal. Many types of ultrasonic detectors include and exploit the properties of piezoelectric materials. Ultrasonic detectors can be used singly or in an array such as a linear array.

An "ultrasonic scanner" is a system device used in conjunction with at least one ultrasonic transducer. When the system is connected to an ultrasonic transducer, the system processes electrical pulses produced by the transducer to generate image data and other useful information. For example, a scanner can produce the following from received ultrasonic waves (e.g., pulse echoes): (a) elapsed time from the instant the outgoing acoustic pulse was produced to the instant the returning acoustic pulse was detected; (b) the strength of the echo; (c) the focal length of a phased array of acoustic pulses; and (d) images of the sample based on (a), (b), and (c). Various scanners operate in one or several modes: (1) "A-mode", in which a single ultrasonic transducer scans a line through the sample to produce echoes that can be plotted as functions of depth along the line; (2) "B-mode", in which a linear array of transducers simultaneously scans a plane through the sample to produce echoes that can be plotted as a two-dimensional image; (3) "M-mode", in which a sequence of B-mode scans are made, in which the respective images follow each other in sequence on a display screen, thereby allowing imaging of motion; and (4) "Doppler-mode" in which the Doppler effect is exploited to produce velocity information associated with the image, useful in imaging blood flow, for example.

An "ultrasonic transducer" is a device that converts received ultrasonic waves into corresponding electrical pulses, that converts input electrical pulses into corresponding ultrasonic waves, or both. (An ultrasonic transducer that converts received ultrasonic waves into corresponding electrical pulses is an "ultrasonic detector," defined above.) Most conventional ultrasonic transducers comprise a piezoelectric element (usually a ceramic or crystal material that exhibits the piezoelectric effect), and many include means for directing and focusing the ultrasonic waves produced by the transducer.

An "ultrasonic wave" or "ultrasound wave" or simply "ultrasound" (US) is an acoustic wave having a frequency greater than the threshold of human hearing (greater than approximately 20 kHz). US waves useful for imaging purposes are generally safe, if not excessively intense, when used around or upon living tissue. Consequently, they are generally useful for medical imaging in non-invasive procedures.

An imaging device 100 as generally configured according to the invention is shown schematically in FIG. 26. The device 100 comprises a light-beam source 102, a light-transmitter/sound-reflector 104, a sound-generator/receiver 106, and a controller 108. The light-beam source 102 desirably (but not necessarily) is a laser that produces a pulsed light beam 110 that can be directed to a sample 112. The wavelength and energy of the pulsed light beam 110 are sufficient to cause the sample 112 to exhibit the photoacoustic effect as the sample receives the pulsed light beam. The light-transmitter/sound reflector 104 is situated relative to the light-beam source 102 to receive the pulsed light beam 110 and to transmit the beam 111 downstream to the sample 112. Meanwhile, the sound generator/receiver 106 produces pulses 114 of ultrasonic waves directed to the light-transmitter/sound reflector 104. To produce these pulses 114, the sound-generator/receiver 104 comprises at least one ultrasonic transducer (not detailed) or analogous device. The light-transmitter/sound-reflector 104 receives the ultrasonic pulses 114 and reflects them as output sound pulses 116 toward the sample 112. The ultrasonic pulses 114, 116 are suitable for ultrasonically imaging a region of the sample 112 on which the pulses converge. Desirably, the light beam 111 and the output ultrasonic pulses 116 interact at the same location and at the same instant in time on or in the sample 112. The light-transmitter/sound-reflector 104 is also situated to receive, as input, ultrasonic pulses 118 output (as pulse echoes and as a result of the photoacoustic effect) by the sample 112, and to reflect these ultrasonic pulses as corresponding input sound pulses 120 to the sound-generator/receiver 106.

The device 100 can include one or more optical elements (not shown) for shaping the beam 110 as required. For example, a converging lens can be placed in the path of the beam 110 to "focus" the beam at the desired depth in the tissue. This focusing lens can be mounted in a manner allowing axial motion of the lens, in the manner of a "zoom" lens. In an alternative zoom lens arrangement, a diverging lens is included with the converging lens, wherein either the converging lens is axially movable relative to a stationary diverging lens, or the diverging lens is axially movable relative to a stationary convergent lens. The lenses are not limited to spherical lenses; one or more aspherical lens can be used. Further alternatively, one or more cylindrical lenses can be used, particularly if: (a) linear illumination of the sample is desired, and (b) the sound-generator/receiver 106 comprises a linear array of ultrasonic detectors.

For imaging living tissue, the power of the light beam as incident on the tissue should not be so high that it causes injury to the tissue. A sensible upper limit for the focused energy of the light beam is 25 mJ/cm$^2$.

The light beam 110 between the light-beam source 102 and light-transmitter/sound-reflector 104 can be conducted using an optical fiber. Considerations useful for selection of the optical fiber include throughput, damage threshold, and spectral range. The throughput and the damage threshold are specifically affected by the core diameter of the fiber, whereas the spectral range is varied by the transmissivity of the material.

An exemplary light-beam source 102 is a Nd:YAG laser pulsed at 5-nm pulse intervals. An exemplary output energy of such a laser is approximately 40 mJ. With a safety factor of 2.5, optical fibers with damage thresholds of 100 mJ can be used. The optical fiber desirably transmits light in the spectral range of 700-1000 nm, indicating use of a multi-mode fiber. An exemplary fiber is a 1.5 mm diameter multimode fiber manufactured by Ceramoptic.

The numerical aperture (NA) of the optical fiber corresponds to the largest angle at which light exits the fiber. This angle, denoted relative to a surface normal $U_{norm}$, is related to the apical angle of a cone of light exiting the optical fiber, which impacts the throughput of the fiber. More specifically, NA=n sin($U_{norm}$). $U_{norm}$ can be determined from the NA and the index of refraction (n) of the interfacing medium:

$$U_{norm} = \sin^{-1}\left(\frac{NA}{n}\right) \quad (2)$$

If the interfacing medium is air, n=1. The solid angle (cone of light) leaving the fiber is:

$$\Omega = 2\pi(1-\cos(U_{norm})) \quad (3)$$

where $\Omega$ is the solid angle, in steradians (sr). From the solid angle and sectional area of the fiber, fiber throughput can be calculated:

$$T = A_{fiber}\Omega \quad (4)$$

Desirably, the light pulses 111 are synchronous with the ultrasound pulses 116 to achieve simultaneous production of ultrasonic echo pulses and ultrasonic photoacoustic pulses by the sample 112. To obtain this simultaneous production, the controller 108 controls at least the temporal aspects of light-pulse production by the light source 102 and of sound-pulse production by the sound generator/receiver 106.

The ultrasonic pulses 118 emanating from the sample 112 are a combination of "echo" pulses produced by reflection of the ultrasonic pulses 116 from the sample and ultrasonic pulses produced by the photoacoustic effect in or on the sample. These ultrasonic pulses 118 are reflected by the light-transmitter/sound reflector 104 as ultrasonic pulses 120 that propagate to the sound-generator/receiver 106.

The sound-generator/receiver 106 can be an integrated device that: (a) produces and outputs ultrasonic waves according to an input electrical signal, and (b) receives incoming ultrasonic waves and transduces them into corresponding electrical signals. An example integrated device in this regard is a conventional ultrasonic probe used with an ultrasonic imaging system. Alternatively, the sound-generator/receiver 106 can comprise respective separate devices for (a) producing and outputting ultrasonic waves and (b) receiving incoming ultrasonic waves.

For receiving ultrasonic pulses 120, the sound-generator/receiver 106 comprises an ultrasonic-detector array (not detailed). As an "array," the ultrasonic-detector array can comprise multiple discrete ultrasonic detectors arranged spatially, or alternatively can comprise a single ultrasonic detector configured to move and thus operate as a "synthetic array." Actual arrays comprising multiple individual detectors allow imaging of the sample without having to move the detectors manually.

An exemplary detector array is a linear array of multiple individual detectors, for example, sixteen individual detectors equidistantly spaced (see FIG. 32(a), for example). The distance between the individual detectors in the array may affect various parameters such as bandwidth. The widest bandwidth can be achieved if the distance between adjacent detectors in the array is $\lambda/2$, for example, where $\lambda$ is the wavelength of the acoustic wave. Since $\lambda$ is inversely proportional to frequency, the relative distance between individual detectors can be determined easily for a given frequency response. The sensitivity of an individual detector is greatest when its thickness is $\lambda/10$. Alternatively to linear arrays, the detectors may be arranged into any of various 2-D arrays.

Upon receiving the sound pulses 120, the detector array in the sound-generator/receiver 106 produces corresponding electrical pulses 122 that are routed to the controller 108 (or to a different controller, not shown), which decodes the pulses to produce an image on, for example, a display 124.

Thus, the device provides simultaneous imaging of a particular location (situs) of the sample by both pulse-echo imaging and photoacoustic imaging. This is made possible because ultrasonic pulses used for pulse echo and light pulses used for photoacoustic imaging impinge at the same location in or on the sample.

The detector array can comprise piezoelectric detectors, which work well and have a long track record of reliability. However, the detectors are not limited to piezoelectric transducers. Another type of detector that can be used in the array is an acousto-electric (AE) "hydrophone," as disclosed herein, that exploits the interaction of an ultrasonic pressure wave and electrical current flowing through an electrically conductive material of the hydrophone. An hydrophone comprises a small region of high current density J (the "sensitivity zone"). The sensitivity zone has a defined width to provide it with a desired resistivity $\rho_0$. The resistivity is responsive to incident acoustic pressure waves, which allows mapping of the ultrasound pressure field represented by peak pressure $P_0$, beam pattern b, and pressure pulse a. FIGS. 27(a) and 27(b) depict general aspects of this hydrophone (see also FIG. 34). Equation (1) relates the detected AE signal (VAE) at the focal position $(x_0, y_0, z_0)$ to the electrical, material, and ultrasound parameters:

$$V^{AE}(x_0, y_0, z_0) = -k\rho_0 P_0 \quad (5)$$
$$\iiint J(x-x_0, y-y_0, z-z_0)b(x, y, z)a\left(t - \frac{z}{c}\right)dxdydz$$

The fundamental relationship of Equation (5), based on the general AE equation (Equation (1)), directly relates properties of the acoustic field to the detected signal. If the sensing element of the hydrophone is thin relative to the acoustic wavelength (e.g., $\lambda/10$) and small compared to the size of the ultrasound focal spot, then the hydrophone sufficiently samples the acoustic beam pattern over the region of constant current density J of the sensing element. The detected AE signal is linearly proportional to the injected bias current I (gain mechanism controlled by the operator) and local pressure AP (measured parameter). Finally, the full 3-D spatial pattern of the ultrasound beam can be obtained by either: (1) mechanically or electronically steering the ultrasound beam relative to the hydrophone or (2) incorporating the hydrophone with an array of detectors.

Another type of ultrasonic detector that can be used is a capacitive micromachined ultrasonic transducer (CMUT). The CMUT operates in the same manner as a parallel-plate capacitor and comprises multiple superposed layers including a metal first electrode, a flexible membrane, a vacuum region, an insulator, and a bottom (second) electrode. As an acoustic wave makes contact with the flexible membrane, the membrane oscillates. The oscillation results in corresponding transient changes in the distance between the electrodes, which produces a change in voltage between them. The voltage changes can be signal-processed to produce an image. CMUTs can be manufactured on a micrometer scale, which allows the fabrication of detector arrays comprising large numbers of individual detectors.

The light-transmitter/sound-reflector 104 is generally an optical element that is transparent to light produced by the light source 102 and that is reflective to the acoustic waves with which the imaging device 100 operates. A particularly desirable configuration of the light-transmitter/sound-reflector 104 is a thin parallel-plate element such as a conventional glass or quartz microscope slide or portion thereof. Alternatively, the parallel-plate element can comprise multiple optical components assembled into a parallel-plate element. Further alternatively, the light-transmitter/sound-reflector 104 can be a prism (e.g., right-angle prism) or other suitably shaped element, so long as it is transparent to the light and reflective to the sound. Advantages of the thin parallel-plate configuration are: (a) its thinness prevents refractive shifting of transmitted light relative to the optical axis, and (b) low cost and simplicity. A particularly advantageous orientation of the thin parallel-plate configuration relative to the light and to the sound is 45° to both. This "dual 45" configuration provides high transmission to incident light from the source 102 and high reflection of incident acoustic waves. It also causes light produced by the source 102 and acoustic waves produced by the sound-generator/receiver 106 to be combined into a coaxial beam of both light and sound that is directed to the sample 112 for imaging the sample simultaneously by both ultrasonic pulse-echo and photoacoustic imaging. Thus, sound and light are simultaneously incident at the same location (situs) in or on the sample 112.

Simultaneous imaging is facilitated by the controller 108, which desirably is configured (programmed) to synchronize light pulses produced by the source 102 with sound pulses produced by the sound-generator/receiver 106. This synchronization also allows acoustic pulses photoacoustically produced by the sample 112 to be detected in a temporally coordinated manner relative to the pulse echo pulses reflected from the same location in or on the sample. The resulting images of the situs by two different imaging modalities working simultaneously provides more image-producing data and hence better images.

If desired or required, a substance can be placed between the light-transmitter/sound-reflector 104 and the sample 112 to achieve approximate matching of index of refraction in this location to the refractive index of the sample 112. Index-matching in this manner ensures minimal loss of light and of acoustic signal, which maximizes imaging efficiency. The particular index-matching substance that is used depends upon the particular wavelength of light produced by the source 102. For visible wavelengths of light, for example, water is suitable for this purpose. Water significantly absorbs light above approximately 900 nm.

First Representative Embodiment

Figure 1:
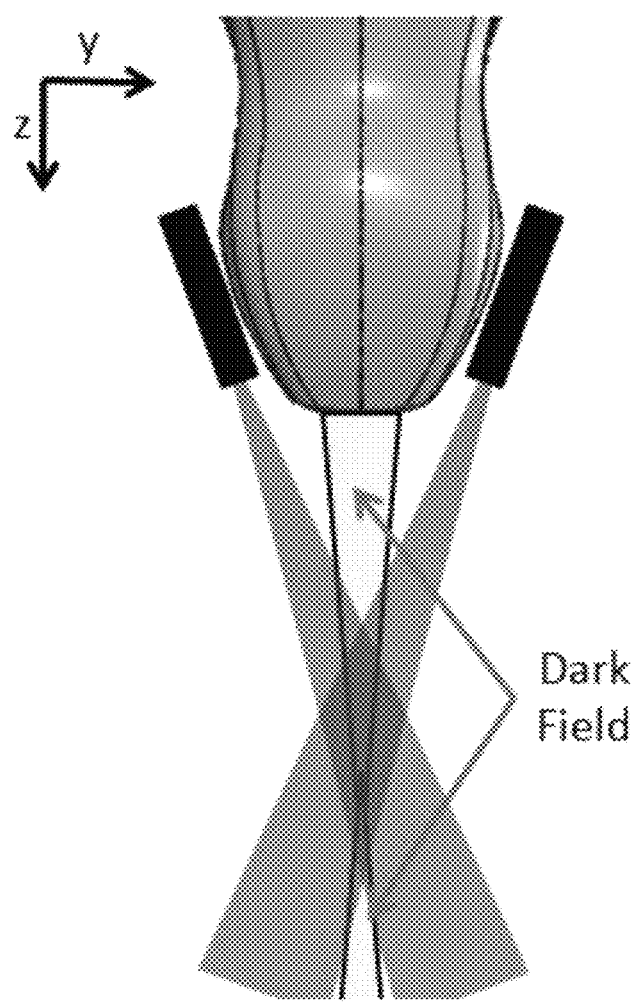
Figure 2A:
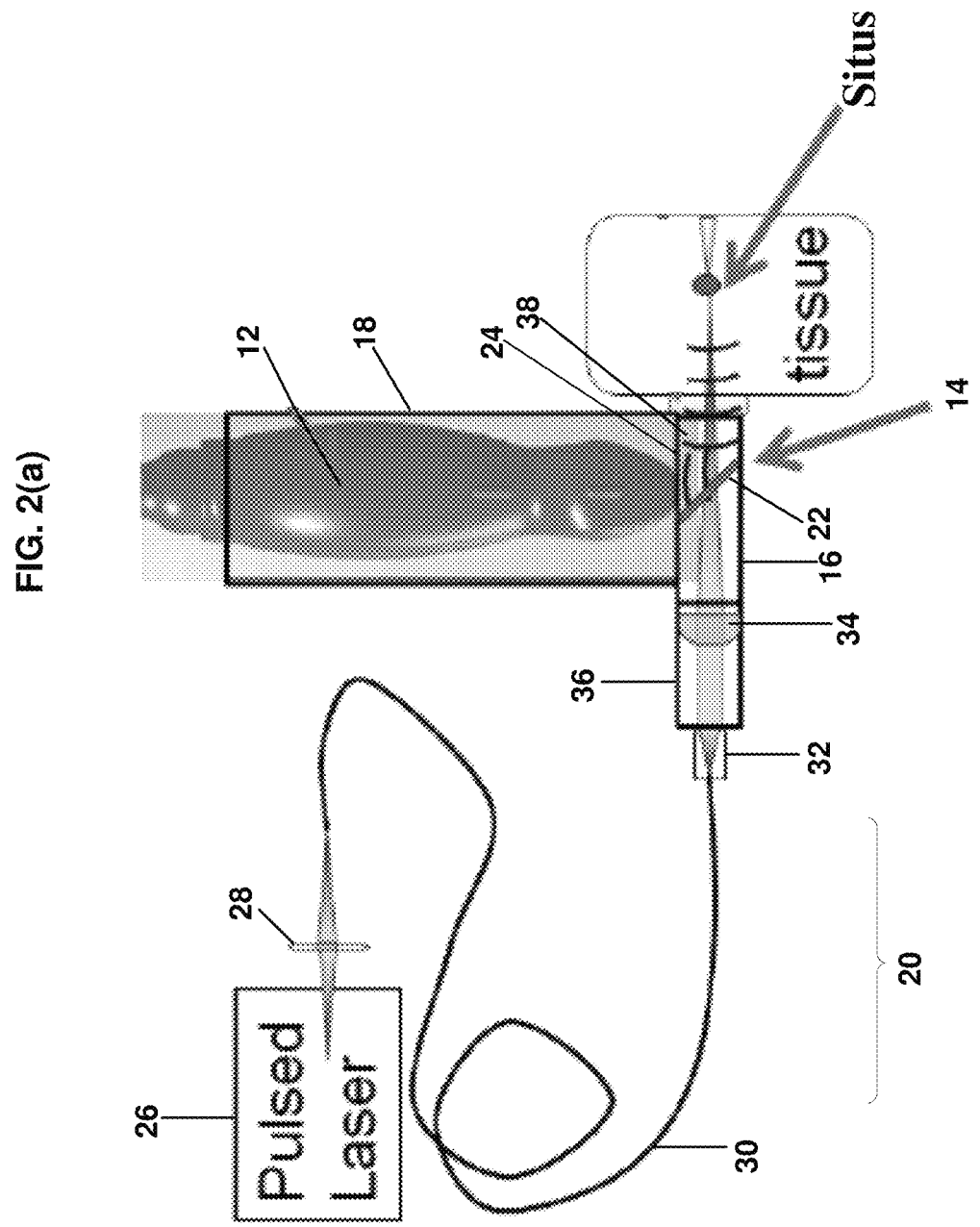
FIG. 2(b) is an elevational section of the device shown in FIG. 2(a).
FIG. 2(c) is an elevational section of the device according to a second representative embodiment.

A first embodiment of an imaging device 10 is configured as a "photoacoustic enabling device" (PED) because it enables a conventional ultrasonic probe to perform real-time and simultaneous acquisition of both ultrasonic (US) data and photoacoustic (PA) data using in-line illumination. To such end the PED can be attached to and interfaced with the ultrasonic probe. Alternatively, the imaging device 10 can include its own US transmitter(s) and detector(s) built-in to the imaging device. The device 10 is shown in FIGS. 2(a) and 2(b). In FIG. 2(a) the device 10 includes an ultrasonic (US) detector portion 12 and a photoacoustic (PA) portion 14. The US detector portion 12 can be configured as a conventional US detector array. The PA portion 14 comprises an acoustic-reflection chamber 16, a detector mount 18, and an illumination portion 20. The detector mount 18 holds the US detector portion 12 in place, the acoustic-reflection chamber 16 comprises an optically transparent US reflector 22 and a chamber 24 containing index-matching liquid 38. The illumination portion 20 of this embodiment comprises a light source 26, coupling optics 28, a multi-mode fiber 30, a fiber collimator 32, and a focusing lens 34. The multi-mode fiber 30 is connected to the light source 26 and to the acoustic-reflection chamber 16, thereby allowing the light source 26 to be remote from the acoustic-reflection chamber. Alternatively, the fiber 30 can be eliminated by incorporating the light source 26 with other components of the device 10 to provide an integral structure.

Further detail of the imaging device 10 is shown in FIG. 2(b), which depicts particularly the US detector portion 12 and PA portion 14. The US detector portion 12 is a conventional US probe (e.g., zOneUltra by Zonare Medical Systems) having a linear array of US detector elements (not shown). The PA portion 14 includes the detector mount 18, the chamber 24, and an optical chamber 36. The chamber 24 contains the index-matching liquid (e.g., water) 38 and the optically transparent US reflector 22. The US reflector 22 is oriented at 45° to the US detector portion 12. The optical chamber 36 houses the focusing lens 34, which desirably is mounted relative to the optical chamber so that the lens 34 can move along its axis A as required for focusing the light beam. Example dimensions of the optical chamber 36 are 1 inch diameter and 2.5 inches length. Between the chamber 24 and the optical chamber 36 is a first window 40 that isolates the air inside the optical chamber from the liquid 38 inside the chamber 24. The multi-mode fiber 30 is coupled to the distal end of the optical chamber 36 via a fiber coupler 42 (desirably an SMA fiber coupler) to deliver light from the source 26 to the lens 34. The chamber 24 includes a drain/fill port 44 by which index-matching liquid 38 can be added to or removed from the chamber 24 (capacity in this embodiment is approximately 20 mL). The opposite end of the chamber 24 includes a second window (sample-coupling membrane) 46, wherein the chamber 24, the US detector portion 12, the first window 40, and the second window 46 form a sealed enclosure for the index-matching liquid 38.

Light from the source 26 enters the optical chamber 36 via the fiber coupler 42 and propagates along the optical axis A to the lens 34. The light passes axially through the lens 34, through the first window 40, through the US reflector 22, and through the second window 46. During use, the device 10 is placed so that the second window 46 is situated adjacent the tissue or other sample (FIG. 2(a)). This arrangement allows the light passing from the reflector 22 through the second window 46 to enter the sample. The light is focused by the lens 34 to the desired depth in the sample so as to converge at a desired situs in the sample. Interaction of the light with the sample at the situs causes the situs to produce corresponding pulses of ultrasound by the PA effect. Meanwhile, US pulses from the US detector portion 12, reflecting from the US reflector 22, also enter the sample. The resulting ultrasound pulses (pulse echoes and US pulses produced by the photoacoustic effect) produced in the sample pass through the second window 46, reflect from the US reflector 22, and enter the US detector portion 12.

A key component in the device 10 is the US reflector 12, which is optically transparent and acoustically reflective. The US reflector 12 desirably does not adversely affect illumination in any way. Example configurations of the US reflector 22 include right-angle prisms, parallel-prism reflectors, and simple glass planes (e.g., 1-mm thick microscope slide). In some devices the right-angle prism (e.g., 25-mm right-angle prism) may exhibit undesirable chromatic aberration, which can complicate alignment. Parallel-prism reflectors provide achromatic transmission, substantially free from optical deviations and dispersions. A glass plate is effectively an extension of a parallel-plate reflector, wherein the glass plate is simply thinner. Use of a thinner plate reduces optical displacement due to refraction. However, the plate should not be so thin that it transmits acoustic waves rather than reflecting them. The acoustically reflective surface desirably is at 45° relative to the US detector portion 12 to obtain near 100% theoretical acoustic reflection.

The first window 40 can be, for example, a glass or rigid, transparent polymer plate that is fully transmissive to the light beam while being sufficiently rigid to remain sealingly attached to the chamber. The second window 46 is an acoustic window that desirably is maximally transmissive to the US waves from the sample and to the light beam. Thus, the second window 46 can be a polymeric membrane or other thin film (e.g., Tegaderm™ from 3M™).

The light source 26 is a source of a pulsed or modulated light beam, such as (but not necessarily) a pulsed laser. An example light source is a frequency-doubled Nd:YAG (Continuum™), which produces 5-ns pulses of wavelength in the range of 700-960 nm (approximately 40 mJ per pulse). These specifications are not intended to be limiting. The wavelength can be selected for optimum penetration into a sample and for optimum PA excitation, for example. The pulse rate and duration can also be selected as required. Furthermore, the light source 26 need not be a laser; the light beam can be produced by any of various sources other than lasers. Even a beam of sunlight can be used if the beam is pulsed or modulated as required to produce a photoacoustic response from the situs.

The "back-end" of the optical chamber 36 of this embodiment is where light is received from the multi-mode fiber 30. It will be understood that the back end can receive direct illumination, optically coupled, or fiber-coupled illumination from virtually any pulsed or modulated light source that is compatible with PAI. The components in the optical chamber 36 comprise collimating and/or focusing optics that direct light along the optical axis A through the US reflector 22 (e.g., parallel glass plate) to illuminate the situs of interest. The US detector portion 12, attached at a right angle to the optical axis A, receives photoacoustic waves generated in the sample and reflected from the US reflector 22. Thus, the optics downstream of the light source 26 are co-aligned with the US detector portion 12. Also, the index-matching liquid 38 (e.g., water) provides highly efficient optical and acoustic coupling at the US reflector 22. The device 10 provides real-time simultaneous and co-registered PE and PA imaging.

Although the US detector portion 12 is shown oriented at 90° to the optical axis, this is not intended to be limiting. The depicted 90° orientation is desirable for simplicity and for maximal efficiency. However, the relative orientation of the US detector and the optical axis can be varied without sacrificing efficiency by incorporating appropriate sonic waveguides and/or optical elements serving to bend the propagation of sound and light, respectively. Similarly, the optical chamber 36 need not be normal to the sample surface.

The optical chamber 36 can be made of any suitable rigid material, including but not limited to any of various metals or any of various engineering polymers.

A perspective view of a PED is shown in FIG. 35, in which surficial details can be seen. Shown are the US detector portion 12, the detector mount 18, the optical chamber 36, the second window 46, and the US reflector 22.

Second Representative Embodiment

This embodiment is a variation of the first embodiment 10, and is shown in FIG. 2(c). The depicted device 50 is similar in many ways to the first embodiment 10 shown in FIG. 2(b). The main difference is the inclusion, in this second embodiment 50, of a collimating lens 52 (desirably achromatic) situated upstream of and coaxially aligned with a converging lens 53. Thus, this embodiment is capable of both focusing and collimating input light. The two lenses 34, 52 are mounted in the optical chamber 56. For focusing the light at the desired situs in or on the sample, the collimating lens 52 can be mounted in a way allowing it to be axially movable, if desired, in the chamber 56 in the manner of a "zoom" lens. The convergent lens 34 can be fixed-mounted in the optical chamber 56. Other components shown in FIG. 2(c) are similar to corresponding components shown in FIG. 2(b) and thus have the same respective reference numerals and are not described further.

Third Representative Embodiment

This embodiment is similar to the first and second embodiments, except that, instead of utilizing a conventional ultrasonic probe as the US detector portion 12, as in the first and second embodiments, one or more hydrophones based on the acousto-electric (AE) effect are used. The AE hydrophone is based upon the AE equation (see above) and Ohm's Law. An electrical current is established across an electrically conductive material. Changes in resistivity of the material (caused by corresponding changes of acoustic pressure from an acoustic wave incident on the material) is translated directly into a change in voltage across the material. Thus, the AE hydrophone exploits an interaction between the incident acoustic pressure wave and the electrical current flowing through the conductive material to map an ultrasound beam pattern. For an isotropic medium, the fluctuations in voltage can be used to map the amplitude and phase of the acoustic field. By limiting the area of the resistive material, current can be constrained to a "sensitivity zone" of high current density, provided the area is smaller than the acoustic wavelength. Such an AE hydrophone has various advantages over traditional hydrophones, such as flexible configurations, choice of materials, simple construction, broadband capability, high sensitivity, and low cost.

Several configurations of AE hydrophones were developed that abruptly or progressively reduce the lateral extent of the resistive material to the desired size. Example configurations included "dumbbell" and "bowtie" configurations. FIGS. 9(a) and 9(b) depict an exemplary rectangular dumbbell configuration and an exemplary bowtie configuration, respectively. The sensitivity zone is a small region in the center of each figure. The large structures flanking the sensitivity zone to the left and right are respective electrodes. The round structures are locations at which respective wire leads can be attached. The respective close-ups show sensitivity zones having edge dimensions of 200 µm×200 µm. These patterns are formed in a resistive material. The electrodes include an upper gold layer that can cover the entire electrode up to the sensitivity zone, or be limited to the circles provided, or omitted altogether. The dimensions of the sensitivity zone establish the potential resolution of the hydrophone and also affect its sensitivity by controlling the resistance between the measuring electrodes.

Initial prototypes of the hydrophones were made having sensitivity zones with edge dimensions of 1 mm, 200 µm, 75 µm, and 30 µm, centered in a 20 mm×30 mm dumbbell or bowtie design. For the resistive material, indium tin oxide (ITO) was used, formed to a thickness of 100 nm. ITO was formed by e-beam evaporation onto an inert, insulative substrate such as glass or fused silica substrate. The thinner the thickness profile, the broader the expected bandwidth (BW). With a thickness of 100 nm, used with sound waves propagating through water, the expected bandwidth was 14.8 GHz. The ITO was shaped by photolithography into the dumbbell and bowtie patterns. The target resistivity of the devices was in the range of 1.5 k$\Omega$ to 10 k$\Omega$. Their initial resistances were measured at 300$\Omega$. Gold was then applied to the electrodes, up to the boundaries of the sensitive areas. Gold-coated electrodes allow conductive leads to be soldered easily to them (specifically to the round pads on each electrode).

In addition to passing induced current and measuring signal voltage, the electrodes define the sensitivity zone and help to control the resistance, and hence the current density and sensitivity, across the device.

The AE hydrophones can be made of any of various electrically conductive materials, including but not limited to carbon powder suspended in gel (e.g., glue or agarose); metal foil (e.g., copper foil), and surface-mounted resistive material. The substrate (e.g., glass or polymer) need not be rigid. The sensitivity zones are formed and located by locally reducing the width of the electrodes to confine the current and increase current density. Note also that use of ITO and of gold-coated ITO is not intended to be limiting. An advantage of ITO is that the sensitivity zone can be accurately shaped by photolithography at a size substantially less than 1 mm square.

An embodiment of a method for forming an AE hydrophone (shown having a bowtie configuration) is shown in FIG. 10. On the surface of a substrate (step 1) a film of ITO is formed (step 2). A hydrophone pattern is created in the ITO by masking and etching (positive photolithography) (step 3). The ITO is etched away (step 4), and remaining PR removed (step 5), leaving the patterned ITO on the substrate. The ITO in regions other than the sensitivity zone are plated with titanium (to facilitate adhesion) and with gold (step 6). If desired, the result of step 6 can be protectively coated for electrical insulation and water-proofing. Respective leads are attached (e.g., by soldering) to the electrodes.

Fourth Representative Embodiment

This embodiment is directed to certain configurations of AE hydrophones as determined by simulation.

The AE hydrophones can be made of substantially any conductive material. As a result, they are not limited to piezomaterials, thereby reducing cost. Each subject hydrophone comprises a central sensitivity zone of indium tin oxide (ITO), with the electrodes being made of ITO or gold (FIG. 16(b) or gold-plated ITO. The center frequency of the hydrophone determines the optimal size of the sensitivity zone. Resistivity $\rho_0 = \rho_0(x, y, z)$ can be variable on the surface of the hydrophone, and the relative resistivity is defined as the ratio of resistivity of the center area over that of the remaining conductive area.

The performance of a bowtie hydrophone can be improved by increasing its relative resistivity. "Rel" is relative resistivity between the center area and the conductive area. Rel=1 means the center area is the same material as the remaining conductive area. The larger the value of Rel, the higher the resistivity of the center conductive area.

MEMS techniques were used to fabricate the AE hydrophones. The simulation aimed at optimizing the design of the AE hydrophone with experimental validation. Multi-dimensional Fourier-based reconstructions were used to optimize the simulation speeds. Several shapes (e.g., bowtie and dumbbell) and a variety of relative resistivities ("Rel" values) were investigated to optimize the hydrophone configurations. Sensitivity and harmonic analyses were also made to investigate the effect of thickness and width of the hydrophone. The simulated curves that were obtained were used to calibrate the real relative resistivity from the experimental data.

As shown in FIGS. 16(a) and 17(a), a first pair of electrodes was used to inject current (AC, typically ~200 Hz) into the hydrophone, and a second pair was used for detecting the AE signal produced by the hydrophone. In the configurations shown in FIGS. 16(a) and 16(b), gold leads in the shape of a bow-tie converged to the resistive element (sensitivity zone) in the center of the hydrophone. The maximum (90°) or minimum (270°) current injection was synchronized with a square-wave pulser/receiver that excited a single-element focused transducer (2.25 MHz, f/1.8, focal length). Common mode noise can be reduced by subtracting the two AE signals with opposite phases. The AE signals, as well as simultaneously acquired pulse echo signals (PE) received by the transducer, were amplified, band-pass filtered, and captured with a fast 12-bit acquisition board. The pulse echo (PE) signal is the radio frequency (RF) signal received by the transducer. A 2-D raster scan provided a 3-D beam pattern based on AE signals was further compared with simulations generated in MATLAB™.

A conventional hydrophone (Onda type HGL-0200) was used as a reference standard for calibrating the pressure received by a subject AE hydrophone. The pressures at the focus under different respective pressures were obtained by sweeping the transducer voltage from high to low. The Onda hydrophone was operated with the same hardware and software filtering characteristics as used for the subject AE hydrophones to ensure consistency in making comparisons. Each AE hydrophone was evaluated at different pressures and injected bias voltages. The transducer pressure was determined by the input voltage to a 2.25 MHz ultrasound transducer (100 V to 400 V. These pressures were converted to pressures based on measurements with the calibrated conventional hydrophone. At each pressure the bias voltage through the AE hydrophone was determined by the applied voltage of the signal generator, variable from high (20 V) to low (0 V). The lowest was referred to as the noise (or "control") signal. The peak-peak value of filtered data was used for calculating sensitivity. The sensitivity of an AE hydrophone can be calculated by dividing the detected voltage by the transducer pressure.

FIG. 17(a) depicts the test setup for characterizing the AE hydrophones. FIG. 17(b) depicts a subject bowtie hydrophone. The current source injected a 200-Hz rectangular waveform into the hydrophone. AE signals were obtained at the maximum (90°) and minimum (270°) of the waveform (FIG. 17(c)). FIG. 17(d) depicts the pulse echo (PE) signal, and FIG. 17(e) shows the AE signals acquired at the maximum ("phase 90") and minimum ("phase 270") of the current waveform. Common mode noise was further reduced by subtracting the two AE signals having opposite phase.

It was assumed that a single-element 2.25-MHz concave transducer was excited by a square pulse obtained from the signal generator. The ultrasound pressure field b(x, y, z) can be created by convolving spatial impulse response in the Field II simulation software.

The electric simulations were based on lead field theory. The current density distribution J(x, y, z) and electric fields were simulated using MATLAB's partial differential equation toolbox. The electrodes (including injecting and detecting) were defined as Dirichlet boundary conditions, and the other boundaries were defined as Neumann boundary conditions. Finite-element analyses was used to simulate the current-density distribution in a purely resistive sample having the same geometry as the experimental one. The equation appropriate for a finite element simulation is the Poisson equation $-\nabla \cdot (\sigma \nabla \varphi) = \rho$ with the Neumann boundary condition $J \cdot n = 0$, where $\rho = \rho_0 [\delta(r-r_1) - \delta(r-r_2)]$ (see FIG. 18(a)) is a dipole with point charges located at positions $r_1$ and $r_2$ within the sample or on the boundaries, to account for an injected current or detecting electrodes. An adaptive mesh-refinement algorithm was used to improve the accuracy of the current-density distribution. FIG. 18(a) shows the refined mesh for a bowtie hydrophone. After computation, the electric voltage and mesh information were downloaded from pdetool. The current density can be calculated by $J = \nabla V$, while making sure that $J \cdot n = 0$ on the edge of hydrophone. In FIG. 18(b), the current density is highest in the center and electrode areas, and decreases quickly away from these areas.

FIGS. 18(a)-18(c) show an AE signal induced by a 2.25-MHz transducer on a bowtie hydrophone configuration having a central gap of 200 μm. Simulations were coincident with experimental results. FIG. 18(a) shows the current distribution and electric field simulated by the conductive media DC application in the MATLAB partial differential equation toolbox, in which two electrodes are defined by Dirichlet boundary conditions, and the other two electrodes are defined by Neumann boundary conditions. In FIG. 18(b) the current-density distribution of the lead field is calculated based on the simulated potential in electric field and mesh information. FIG. 18(c) shows a simulated AE envelope dB plot at the focus of the bowtie hydrophone, having a sensitivity zone of 200 μm×200 μm. The dimensional unit in FIGS. 18(b) and 18(c) is mm.

To avoid noise-related interference, the AE signal $V_i^{AE}$ at $(x_0, y_0, z_0)$ is applied to the band-pass filter with the same center frequency as that of the transducer. In FIG. 19, if the center of the beam pattern points at $C(x_0, y_0, z_0)$, then any point P in the ultrasound pressure field (x, y, z) can be described in the electric field as $(x+x_0, y+y_0, z+z_0)$:

$$V_i^{AE}(x_0,y_0,z_0,t) = -P_0 \iiint K_I \rho_0 (\tilde{l}_i^L \cdot J^I)(x+x_0,y+y_0,z+z_0)[\int b(x,y,z)a(t-z/c)h(t'-t)dt']dxdydz \quad (6)$$

where $P_0$ is the amplitude of the pressure pulse, $K_I = K_I(x, y, z)$ is the interaction constant having a value of approximately $10^{-9}$ Pa$^{-1}$, $\rho = \rho(x, y, z)$ is the resistivity, $J(x, y, z)$ is the current distribution of the hydrophone, b(x,y,z) is the ultrasound beam pattern, $$a\left(t - \frac{z}{c}\right)$$

is the pulse waveform, h(t) is the band-pass filter with the same center frequency as that of the transducer. FIG. 19 is a schematic of the AE effect on the bowtie hydrophone. The coordinate center O(0, 0, 0) is at the center of the sensitivity zone. The transducer center is $C(x_0, y_0, z_0)$, and any point P in the ultrasound pressure field (x, y, z) can be described in the electric field as $(x+x_0, y+y_0, z+z_0)$.

Since $K_I = K_I(x, y, z)$ and $\rho_0 = \rho_0(x, y, z)$, both depend upon material properties. They can be combined together with J(x, y, z) so that:

$$w_i(x, y, z) = K_I(x, y, z)\rho_0(x, y, z)(J_i^L \cdot J^I)(x, y, z) \text{ and} \quad (7)$$

$$p(w, y, z, t) = b(x, y, z)a\left(t - \frac{z}{c}\right) \quad (8)$$

where p(x, y, z, t) is the ultrasound wave field at time t, then $V_i^{AE}(x_0,y_0,z_0,t)$ can be calculated quickly by Fourier transform:

$$V_i^{AE}(x_0,y_0,z_0,t) = -P_0 \iiint w_i(x+x_0,y+y_0,z+z_0)[\int p(x,y,z,t)h(t'-t)dt']dxdydz = -P_0 F_{x,y,z}^{-1}\{W_i^*(k_x,k_y,k_z)F_{k_x,k_y,k_z}[F_t^{-1}(P(x,y,z,k)H(k))]\} \quad (9)$$

where $F_{x,y,z}^{-1}$ is the 3-D inverse Fourier transform over $(k_x, k_y, k_z)$, W is the x-y-z 3-D Fourier transform of w(x, y, z), W* is the conjugate of W, $F_{k_x,k_y,k_z}$ is the 3-D Fourier transform over (x, y, z), $F_t^{-1}$ is the inverse Fourier transform over k, P(x, y, z, k) is the 1-D Fourier transform of p(x, y, z, t) over time t, and H(k) is the Fourier transform of h(t).

A complete map of an ultrasound beam pattern was, therefore, obtained by scanning the ultrasound beam along the lateral and level directions over the surface of the AE hydrophone. If the hydrophone is thin compared to the wavelength) of the ultrasound, then the solution reduces to a double integral over the lateral and level directions at the depth of the hydrophone. If the AE hydrophone is oriented on the x-y surface plane, $w(x+x_0, y+y_0, z+z_0)$ becomes $w(x+x_0, y+y_0)$, and:

$$V_i^{AE}(x_0,y_0,t) = -P_0 \iiint w_i(x+x_0,y+y_0)[\int p(x,y,t)h(t'-t)dt']dxdy = -P_0 F_{x,y}^{-1}\{W_i^*(k_x,k_y)F_{k_x,k_y}[F_t^{-1}(P(x,y,k)H(k))]\} \quad (10)$$

Dimensional analysis over thickness and width can be done along a cross-section (x-z plane), in which $w(x+x_0, y+y_0, z+z_0)$ becomes $w(x+x_0, z+z_0)$, $J^I$ is assumed to be constant and independent of position (x, z) over the cross-section, and the unit vector of of $J^I$ is the same as $\tilde{l}_i^L$:

$$V_i^{AE}(x_0,z_0,t) = -P_0 \iiint w_i(x+x_0,z+z_0)[\int p(x,z,t)h(t'-t)dt']dxdz = -P_0 F_{x,z}^{-1}\{W_i^*(k_x,k_z)F_{k_x,k_z}[F_t^{-1}(P(x,z,k)H(k))]\} \quad (11)$$

where $w_i(x, z) = K_I(x, z)\rho_0(x, z)J^I$. The connection between the electrodes and the sensitivity zone is usually the small area around the center of the cross-section; the detected $V_i^{AE}$ be the average value over the area around the center. For convenience, the connection can be assumed to be one point on the center, in which event the detected $V_i^{AE}$ is the value on the center.

A 3-D simulation of the magnitude of the AE signal was created by convolving the ultrasound field (simulated with Field II™) with the current-density distribution in the lead field. This convolution can be accelerated using a Fast Fourier Transform algorithm. Combining the ultrasound beam and bowtie electric field, the simulated result shown in FIG. 18(b) and FIGS. 20(a) and 20(b).

FIGS. 20(a)-20(d) depict simulation results obtained with hydrophones having different respective shapes. The AE signals produced by the hydrophones were induced by a 2.25-MHz transducer. The three hydrophone shapes were triangular bowtie, circular dumbbell, and rectangular dumbbell (FIG. 20(a)), each with a sensitivity zone of about 200 μm×200 μm. In the simulations it was assumed that each hydrophone had identical resistivity. FIG. 20(b) shows the respective simulated AE signals, along the x-y plane, at the focus for each hydrophone. The bowtie hydrophone had the highest side-lobes and largest beam width in the x-direction. FIG. 20(c) shows the AE profile at the center in the x-direction. FIG. 20(d) depicts the center profile in the y-direction. The rectangular dumbbell hydrophone had the smallest full width at half maximum (FWHM) and lowest side-lobes in the x-direction. The circular dumbbell hydrophone had the lowest side-lobes, but the rectangular dumbbell exhibited the most rapid decline of dB with distance from the center and had the lowest dB value at more than 4.5 mm from the center. The plot denoted "beam" is the simulated transducer beam pattern, created by convolution of the ultrasound field with the AE signal obtained by the Onda hydrophone.

Therefore, the shape of the hydrophone is an important determinant of the current distribution and ultimately the selectivity and sensitivity of the AE hydrophone for mapping an ultrasonic beam pattern, as depicted in FIG. 20(b). The x-y cross-section at the focus of the bowtie hydrophone was elliptical, but circular for the circular dumbbell and rectangular dumbbell hydrophones. Three-dimensional images of the cross-sectional 40-dB envelope of the simulations are shown in FIGS. 21(a)-21(c), showing comparisons between the beam pattern (FIG. 21(a)), rectangular dumbbell at Rel=1 (FIG. 21(b)), bowtie at Rel=1 (FIG. 21(c)), and rectangular dumbbell at Rel=50 (FIG. 21(d)).

With respect to the effect of relative resistivity ("Rel") of materials, FIG. 21(a) shows the ideal beam pattern of the 3-D cross-sectional image of the 40-dB envelope. At the focus center, in the x-z cross-section, the center two holes establish the first side-lobe position. For a bowtie hydrophone, if Rel=1 (FIG. 21(c)), the center two holes are separated into four holes, and the x-y cross-section is elliptical. If Rel=50 (FIG. 21(d)), the x-y cross-section is spherical and close to the ideal shape shown in FIG. 21(a). The bowtie hydrophone (Rel=50) hydrophone shows almost the same performance as the rectangular dumbbell (Rel=1) hydrophone (FIG. 21(b)).

FIG. 22(a) shows that hydrophone sensitivity increases with thickness, up to more than half the wavelength of the transducer, beyond which sensitivity is substantially constant. The linear range of sensitivity versus thickness is from 0 to half-wavelength. Thickness has an important effect on the spectrum of the AE signal. Whenever thickness increases from 0, the magnitude of the $1^{st}$ harmonic decreases and reaches a minimum at thickness $\lambda/2$. If thickness is greater than $\lambda/2$, the $1^{st}$ harmonic exhibits an increase. If thickness is greater than $\lambda$, the harmonic components move leftward and reduce the center frequency of the main lobe. In the time domain, the two top peaks begin to move in opposite directions, without changing the maximum. Hence, the source of spectrum distortion is mainly thickness.

FIGS. 22(a)-22(d) are plots of simulation results. The thickness analysis for the AE hydrophone was made by ranging thickness from 0.025 mm to 0.775 mm FIG. 22(a) is a sensitivity plot, FIG. 22(b) shows the simulated AE A-lines at the center of the cross-section, FIG. 22(c) is the spectrum of the simulated AE A-lines for thickness at about half wavelength, and FIG. 22(d) is a spectrum of the simulated AE A-lines for thickness greater than half wavelength. The center frequency of the transducer was 2.25 MHz, and its wavelength was about 657 μm.

Turning to the effect of lateral width, since the x-z cross-section of the sensitivity zone is uniform, $V_i^{AE}$ can be simulated along the cross-section. Both width and thickness of the sensitivity zone are important for the detected AE voltage. Based on Equation (10), $V_i^{AE}$ can be obtained by applying the inverse Fourier transform of the product between the current distribution and ultrasonic field in the frequency domain.

In FIGS. 22(a)-22(d), the width of the transducer was varied from 0.025 mm to 7.025 mm. In the time domain, the peak positions of $V_i^{AE}$ are maintained constant. Sensitivity reached maximal value when lateral width was larger than the beam size. The side-lobe position decreased and converged to a constant value. For the frequency spectrum of the AE signal, the magnitude of the higher harmonic components decreased and converged to a substantially constant value.

FIGS. 23(a)-23(b) and 24(a)-24(d) present results of analyses of experimental data obtained with a dumbbell (Rel=1) hydrophone. SNR (signal-to-noise) analysis set forth in FIGS. 23(a)-23(b) shows the effect of injected current and transducer pressure. The sensitivity zone in the center of the rectangular dumbbell (Rel=1) is 75 μm×75 μm. The center frequency of the transducer was 2.25 MHz. FIGS. 24(a)-24(b) are plots of sensitivity data, and FIGS. 24(c)-24(d) are plots of normalized sensitivity obtained with a dumbbell (Rel=1) hydrophone, showing the effects of injected current and transducer pressure. In FIGS. 24(a)-24(d), if sensitivity is in units of nV/Pa, then sensitivity increases with applied current, reaching about 0.4 nV/Pa for a 20-V signal. Since it is difficult to discern the effect of current in sensitivity, the unit is further divided by the current, nV/Pa/V, which is referred to as "normalized sensitivity," or sensitivity corrected by bias voltage. In FIG. 24(c), the normalized sensitivity is constant whenever the injected current is greater than 4 V. In FIG. 24(d), if current is greater than 4V, then normalized sensitivity is independent of transducer pressure. Hence, sensitivity is linearly related to injected current. As $\vec{j}_i^L$ is in the same direction as $J^J$ in the sensitivity zone, $w_i(x,y)=K_i(x,y)\rho_0(x,y)(\vec{j}_i^L \cdot J^J)=K_i(x,y)\rho_0(x,y)[J_L]$. The sensitivity can be controlled by the injected current, hydrophone width, and hydrophone thickness.

The SNR (signal-to-noise ratio) is defined as the ratio of the measured peak-to-peak value of filtered data between the signal and the noise (signal source is 0 volt). The data at 1 V current was assumed to be a noise signal. SNR increased linearly with increased injected current (FIG. 23(a)) and transducer pressure (FIG. 24(b)). Hence, SNR can be improved by increasing the bias injected current.

In the subject hydrophones, ITO ($5\times10^{-4}\sim5\times10^{-5}$ Ω·cm) fills the sensitivity zone, and gold (Au; $2.4\times10^{-6}$ Ω·cm) covers the remaining area of the hydrophone. The ratio of the resistivity of ITO to Au was in the range of 20 to 100. The relative resistivity of ITO/Au can be calibrated using the simulated and experimental data obtained with the bowtie hydrophone. Relative resistivity does not affect the center profile or the beam width along the y-direction (FIG. 25(b)), so only the profile along the x-direction was used to approximate the relative resistivity of ITO/Au. In FIG. 25(a), when Rel is increased from 1 to 50, the side-lobe decreased and converged to an ideal beam profile. At 21 dB (FIG. 25(c)), if the relative resistivity of ITO/Au is higher than 18, the beam width became equivalent to the experimental result (3.3 mm) This is consistent with the ratio of resistivity of ITO/Au being over 20. Therefore, the accuracy and sensitivity of the AE hydrophone is a function of shape and resistivity of the device.

FIGS. 25(a)-25(d) depict the effect of the relative resistivity of ITO/gold (Au) over the AE bowtie hydrophone beam pattern. "Experimental" denotes a bowtie hydrophone with ITO in the sensitivity zone (200 μm×200 μm) center and gold in the remaining areas of the hydrophone. "Beam" denotes the transducer beam pattern on a focus simulated by FIELD II. "Simu. Rel" denotes simulated AE signals on the focus with different respective relative resistivities of ITO/Au. FIG. 25(a) is an exemplary profile in the center, along the x-direction, where "experimental" had a −30-dB side-lobe caused by reflected noise, "Rel=1" had the highest side-lobe and largest FWHM; but, when Rel was further increased, the AE profile converged to the transducer "beam" pattern. In FIG. 25(b), each profile of simulated AE signals with different respective Rel values had almost the same shape as the transducer "beam" pattern along the y-direction. The data within [−3, 3] mm was close to the transducer "beam" pattern, but the noise was high out of that range. FIG. 25(c) shows a determination of the lowest relative resistivity of ITO/Au that can produce an ideal or experimental result. "x(y)-R" is the beam width at 21 dB along the x(y) direction for simulated hydrophones with different relative resistivities. "x(y)-experiment" is the beam width at 21 dB along the x(y) direction for an actual ITO/Au hydrophone. "x(y)-beam" is the beam width at 21 dB along the x(y) direction for a simulated transducer beam pattern, created by the convolution of the ultrasound field with AE signals obtained by the reference hydrophone. At 21 dB, if the relative resistivity of ITO/Au is higher than 18, the beam width (3.3 mm, "x-R") becomes equivalent to the experimental result (3.3 mm, "x-experiment"). The relative resistivity of ITO/Au does not affect the center profile or beam width along the y-direction.

Based on the above, the dumbbell AE hydrophone produced the best beam pattern of a 2.25-MHz ultrasonic transducer. Specifically, the lateral and axial resolutions of this hydrophone were consistent with images produced by the reference hydrophone. A bowtie-shape hydrophone having high relative resistivity also exhibited high mapping performance. Since it is easier to fabricate a bowtie configuration than a rectangular dumbbell (requiring a long and uniformly thin gap between the electrodes, especially a gap of, for example, several μm), any performance trade-off associated with selecting a bowtie hydrophone rather than a rectangular dumbbell hydrophone may not be significant, especially for a high-frequency transducer. The higher the relative resistivity, the stronger the AE signal that can be detected, and the better the performance of the hydrophone.

Fifth Representative Embodiment

This embodiment is directed to exemplary arrays of ultrasonic detectors, particularly of detectors based on the acousto-electric (AE) principle, discussed in the fourth representative embodiment. As discussed, AE detectors exploit the acousto-electric effect, which is an interaction between ultrasound and electrical conductivity for detecting and imaging an incoming acoustic beam. As discussed above, AE detectors can be made of substantially any electrically conductive material and can be arranged in any of various arrays, including one-dimensional (linear), two-dimensional (planar), and three-dimensional.

For example, a planar (2-D) array can be made using multiple individual AE detectors. FIG. 32(a) shows a 4×4 array of sixteen detectors. The detectors are all connected in a single channel. In this figure, the incident US waves are perpendicular to the page. The detectors are formed on a two-layer substrate, wherein the upper layer is the visible layer (in the figure) and the center pin of each detector is connected to the underlying lower layer. The detectors are separated from one another by λ/2. Electrical connections for each detector are shown in FIG. 32(b), in which each detector is provided with a respective current bandpass filter. Each detector is encoded by controlling the frequency of current injection. This can be achieved by, for example, using periodic current chirps, wherein the frequency of each detector is controlled by the respective bandpass filter. Each detector captures both current-induced and ultrasound-induced voltage modulations. (Current-induced modulations are in MHz or Ghz, and ultrasound-induced modulations are in MHz.) The resulting ultrasound image is constructed from a known spatial current map for the array, as facilitated for example using a FFT algorithm.

Figure 3:
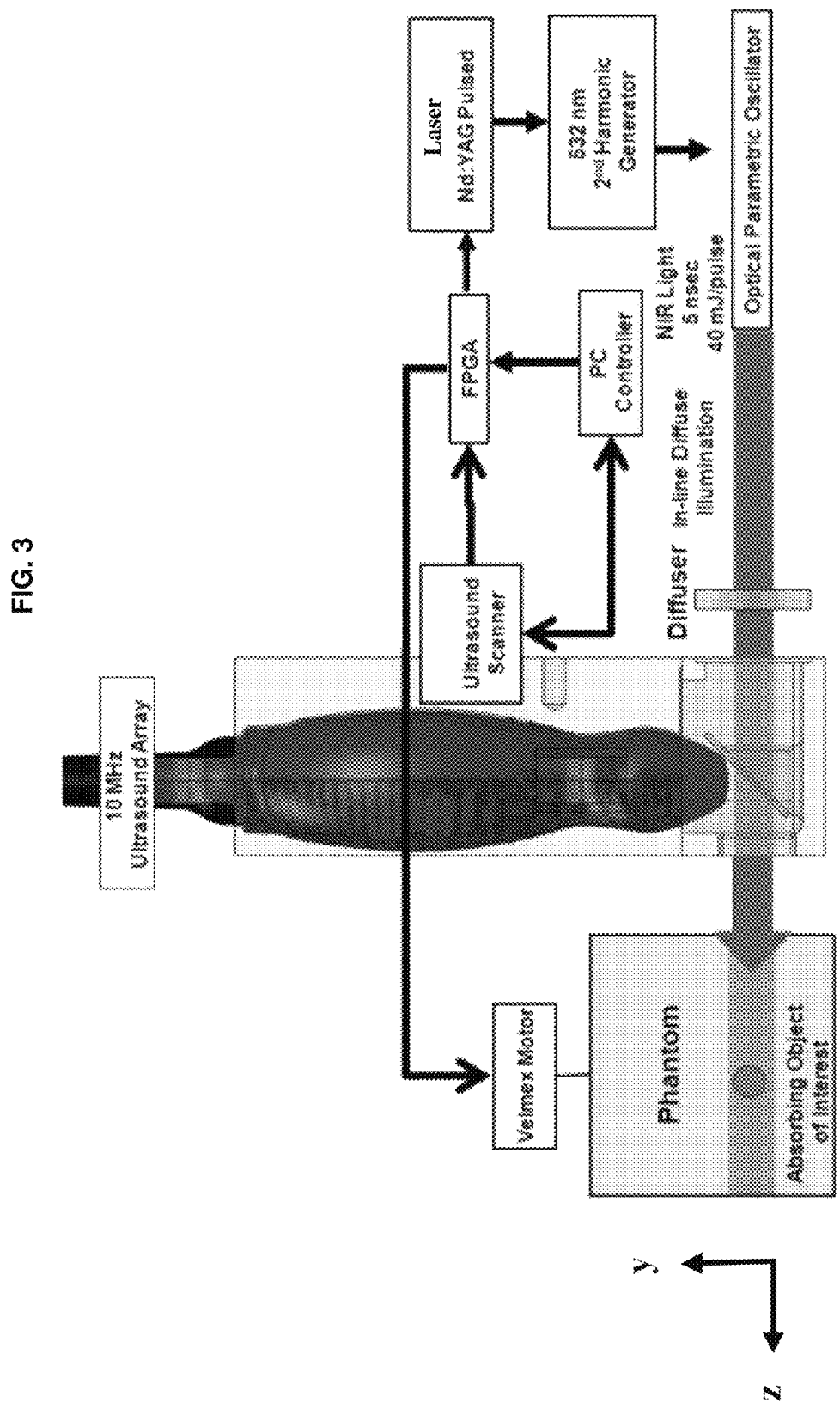
FIG. 3 is a schematic diagram of the experimental setup discussed in Example 1.

Turning now to FIGS. 33(a) and 33(b), 3-D arrays are shown, each configured as a layered array. Each layer is thin compared to the acoustic wavelength (<50 μm) and separated from neighboring layers by respective insulating layers (e.g., polyimide). The layers are acoustically transparent. The detectors in each array are energized by chirp encoding. Depth in the array is encoded by controlling the frequency of injected current (or phase) according to each particular layer. Both current-induced and ultrasound-induced voltage modulations are captured from each detector in the array. An extended time signal is used to reconstruct an incident acoustic-pressure wave. In FIG. 33(a) current frequency is encoded according to layer, and in FIG. 33(b) current phase is encoded according to layer.

Example 1

This example is directed to demonstrating operation of the first representative embodiment. The light source was a frequency-doubled Q-switched Nd:YAG laser (Continuum Surelite™ 1-20) pumping an optical parametric oscillator (Continuum Surelite™ OPO PLUS) to provide light pulses at selectable wavelengths between 680 nm and 2000 nm. Experiments on phantoms were conducted with the laser output set to 700 nm. Light pulses (at 5-ns intervals) were synchronized with a reference clinical ultrasound scanning probe (Zonare Medical Systems) using a field-programmable gate array (FPGA). The particular reference probe was a linear array transducer (7 MHz center frequency) containing 128 detector elements from which 64 channels could be collected simultaneously. Light pulses (5 ns, approximately 40 mJ/pulse) were directed toward a sample of interest suspended in a "phantom" (substitute for an actual clinical sample). The pulses passed through a diffuser a few centimeters before arriving at the object of interest. Measured fluences were 7 to 15 mJ/cm$^2$, within the energy density standards set by ANSI17. Matlab™ was used to control all instruments, manage the data collection and process the images obtained. FIG. 3 is a schematic diagram of the setup and control flow.

A linear motor (Velmex) was employed to move the phantom linearly to collect three-dimensional (3D) data sets. The phantom was scanned at a rate of 1 mm/s, acquiring 20 fps for an inter-frame distance of 50 μm. The rate at which PA data could be obtained was limited by the pulse-repetition rate of the laser set to 20 Hz.

Various simple phantoms were scanned and imaged to confirm the imaging properties of the system. Example simple phantoms included crossed strings, a graphite rod, a taught thread, and a rat's tail. One objective of the experiments was to compare the results obtained using the PED of the first representative embodiment with results obtained using a conventional US pulse-echo probe (no PA imaging).

Using the PED embodiment, PA and pulse echo (PE) data were obtained simultaneously from a stationary wire target and from a transparency bearing a printed image. The PA images and PE images were formed with delay and sum beam-forming, based on one-way and two-way propagation, respectively. A thin wire (d=127 μm) allowed calibration of laser firing with respect to the initial excitation of an acoustic plane wave. Whenever the beam-forming timing was sufficiently close, the PE and PA images of the wire cross-section overlapped.

Images of a rod phantom obtained using the 25-mm right angle prism as the US reflector showed minimal image degradation. The size of the rod was 0.40 mm (lateral)×0.50 mm (axial) [FWHM].

Images obtained of the tail of a rat cadaver (FIGS. 4(a)-4(b)) exemplified use of this device for imaging a situs in an animal. To obtain the images, bonded parallel prisms were used as the US reflector 12. The PE image revealed the surface boundaries of the tail and accurately showed the 5-mm diameter of the tail in the region being imaged. In the PA image obtained with laser light of λ=700 nm, it was observed that most of the light was absorbed in the first 2 mm of depth in the tail, which may have been from clotted blood. In any event, the results demonstrated use of this embodiment for imaging biological tissue.

Using a microscope slide as the US reflector 12, images of a cross-section of a 127-μm thick Teflon blue wire were obtained. See FIGS. 36(*a*)-36(*b*). Both figures show close co-registration of the PE data with the PA data. The figures were plotted on exactly the same scales. In both instances the wire was found at the same imaging depth, about 25 mm from the surface of the device. The images on the left show features down to −35 dB, at which beam-forming artifacts can be seen. Noise can also be seen in the PA image down to −35 dB. The images on the right are plotted so that signals about the FWHM are shown. The symmetrical characteristic of these images illustrates the accurate imaging capability of this embodiment. The resolution in the axial dimension between the PA and PE images are different due to the one-way versus two-way wave propagation of the PE versus PA devices.

Example 2

This example is similar to Example 1, except that the phantom used was a transparency phantom, as shown in FIG. 5(*a*). The transparency phantom was imaged twice, once using conventional trans-illumination, and a second time by PAI using the first representative embodiment. Since the transparency phantom was thin and not rigorously aligned, the entire plane of the transparency did not appear at a single imaging depth. Under such a condition, to compare the respective images obtained, the maximum amplitude projection (MAT) of each 3-D data set was calculated. Results are shown in FIGS. 5(*b*)-5(*c*), showing maximum projection along the axial directions (z-directions) of the scanned phantom. The image in FIG. 5(*b*) was produced using US data acquired by conventional trans-illumination, and the image in FIG. 5(*c*) was obtained from data acquired using the PED of the first representative embodiment. Both images were plotted on a hot scale (−15 dB from maximum) with similar dimensions. In both techniques, the light had a wavelength of 700 nm and a fluence of approximately 12 mJ/cm$^2$. To illustrate the 3-D aspect of the phantom, a 3-D rendering of the data obtained using the PED is shown in FIGS. 6(*a*) and 6(*b*), in which FIG. 6(*a*) is a 3-D rendering of the PE image, and FIG. 6(*b*) is a 3-D rendering of the PA data of the same transparency at the same angle as in FIG. 6(*a*).

The MAP images confirmed that the PED of the first representative embodiment did not introduce any significant distortions to the image, and that the image obtained using the PED was comparable to the image obtained conventionally by transillumination. The PED also allowed on-axis illumination, independently of wavelength. Any differences between the two images (FIGS. 5(*b*) and 5(*c*)) of "EUNIL" can be attributed largely to differences in illumination.

Example 3

In this example, the device embodiment shown in FIG. 2(*c*) was used to image, in vivo, a subcutaneous tumor in a mouse. The device was also used to image a mouse pancreas imbedded in a gel.

The light source was an optical parametric oscillator pumped by a frequency doubled pulsed Nd:YAG laser, which produced 5-ns light pulses (λ=700-960 nm) through the device and onto the sample. The optical chamber was 2.5 inches long and 1 inch diameter. The optical chamber contained the optics that provided line illumination 1 cm deep (from the surface of the second window). The optics comprised a fiber coupler, an achromatic collimator, and a cylindrical lens to focus the light in the elevational direction similar to the acoustic focus. Matlab™ (Mathworks) was used to control communication with the laser, motors (Velmex), ultrasound scanner (Zonare Medical Systems type zOneUltra), timing generator (Quantum Composer type 9520), fast data-acquisition board (Signatec type PDA12), and to capture the photodiode signal. All software for controlling the instruments during scanning and during later processing of raw data into images was controlled in Matlab™ with custom software. A fast photodiode (ThorLabs type Det10A) recorded the pulse-to-pulse variation, which was used to normalize the energy for different wavelengths and pulses.

A mouse pancreas was extracted and suspended in an agarose GPG/LE™ gel to create a stationary rugged sample. The pancreas was illuminated with 13 mJ/cm$^2$ light from the laser and imaged using the device of FIG. 2(*c*). During imaging the device was hand-held and coupled to the sample using conventional ultrasound gel. During data acquisition at 20 Hz, the probe was moved by hand to various locations on the gel. The sample and PED were also held in stationary positions, using a table top as support, while obtaining a hyper-spectral data set comprising 10 frames per wavelength in the range of 700 nm to 950 nm at 10-nm increments. A similar data set was also acquired in another position on the pancreas.

For in vivo imaging of the pancreatic tumor, the imaging device was positioned, with use of an ultrasound coupling gel, to acquire cross-sectional images of the tumor region. Four-dimensional data (3-D space+optical wavelength) was acquired by scanning the mouse ten mm in the elevational direction at wavelengths 700-950 nm in 50-nm steps using 18 mJ/cm$^2$ of light energy on the surface. A hyper-spectral 2-D image was also recorded at the peak of the tumor protrusion by using 10-nm steps in the wavelength range of 700-960 nm Pulse-echo images acquired using the ultrasonic probe were complemented with high-resolution pulse-echo images using a Visual Sonics Vevo 2100 probe and MS550D (55 MHz maximum) probe. These devices allowed obtaining a high-resolution image of the tumor area and confirming vascular flow by pulse Doppler, prior to imaging the tissue with the PED.

The PE image of the excised mouse pancreas, displayed with a dynamic range of −40 dB from peak intensity, is shown in FIG. 7(*a*). The PA image using 800-nm light and a dynamic range from peak to −15 dB is shown in FIG. 7(*b*). The strong PA signal in the lower right quadrant of the pancreas suggests blood in that region.

A sagittal view of an in vivo pancreatic tumor in a mouse is shown in FIG. H. The PA data was acquired simultaneously with the PE data for an automatic co-registration of the two images. The PE data is displayed on a 35-dB scale, and the PA data is displayed on a 15-dB scale. The presence of a large vasculature was confirmed with a color Doppler transverse image acquired using the Vevo 2100.

Example 4

This example is directed to functional tests of several hydrophones configured as discussed in the third representative embodiment. In each hydrophone, two leads were connected to each electrode, yielding four leads per hydrophone.

Hydrophones were tested using the testing apparatus shown in FIG. 11. Voltage from a signal generator (Agilent 33220A, Agilent Technologies, Santa Clara Calif.) was applied across two of the four hydrophone leads in the form of a 200-Hz square wave at voltage levels ranging from 1 V to 20 V peak-to-peak. Induced current was a function of the devices' electrical resistance, which ranged from 160Ω to 220Ω in the case of the hydrophones with gold electrodes and from 1.8 kΩ to 90 kΩ for hydrophones in which the electrodes were uncoated ITO. Current was monitored by measuring the voltage across a 1Ω resistor inserted into the circuit.

The hydrophones were raster-scanned at the focal plane of a 2.25 MHz transducer (Panametrics NDT V395, focal depth F=68.6 mm, and element diameter D=38.1 mm) Transducer voltage was normally set to 400 V, corresponding to a pressure output of 500 kPa, but readings were also taken at 100 V, 200 V, and 300 V for sensitivity testing.

Ultrasound pulses were triggered in synchrony with the injected 200 Hz square wave at 90° and 270° (phase during cycle). Since the phase of the AE signal also depended on the phase injected current, subtracting the negative phase from the positive phase effectively reduced common-mode noise, such as the US vibration potential, while doubling the AE signal amplitude.

The induced voltage across the hydrophones was passed through the second pair of leads into a series of differential amplifiers (LeCroy/Preamble DA 1855A) for a total gain of, typically, 60 dB, and on to a waveform digitizer (Signatec PDA12A) and oscilloscope. An Onda HGL-0200 capsule hydrophone was used as a standard against which to compare the subject hydrophones.

Four hydrophones were made, each on a glass substrate, both with and without gold electrodes, in two configurations, as shown in Table 1, in which sensitivity was measured at 10 mA induced current.

TABLE 1

| Config. | Gold Electrode? | Sensitivity Zone | Init DC Resistance | Sensitivity (nV/Pa) |
|---|---|---|---|---|
| Bowtie | Yes | 1.0 mm | 220 Ω | 2.00 |
| Dumbbell | Yes | 200 μm | 163 Ω | 0.22 |
| Bowtie | No | 200 μm | 90 kΩ | 0.98 |
| Dumbbell | No | 75 μm | 11.8 kΩ | 1.20 |

An acousto-electric signal from the 2.25 MHz transducer was obtained for all of the hydrophones. Pulse-echo and acousto-electric responses of the first hydrophone listed in Table 1 are plotted in FIGS. 12(a)-12(b). FIG. 12(a) shows the A-line pulse/echo response for an ITO dumbbell hydrophone having a 75-μm sensitivity zone from the 2.25 MHz transducer. FIG. 12(b) shows the acousto-electric response of the same hydrophone at 500 kPa and 10 V applied voltage. Depth (in mm) is based on the measured response time multiplied by the speed of sound in water: 46.3 μs×1.48 mm/μs=68.6 mm (=focal length). The subject hydrophone had a signal strength of 1 mV at 500 kPa using a 2.25 MHz transducer and a bias current of 10 mA. It had a signal-to-noise ratio (SNR) of 38 after averaging 100 samples at each point, with NEP=65.2 kPa.

Given the above parameters, sensitivity was calculated at S=2 nV/Pa. Gold-on-ITO hydrophones with smaller sensitivity zones exhibited better spatial resolution but with less sensitivity. The dumbbell hydrophone with the 200-μm sensitivity zone had an output of 0.11 mV and sensitivity of 0.22 nV/Pa for 12 mA of induced current. The resolution improved by a factor of 25 over the hydrophone having a 1-mm square sensitivity zone, which brings it to the same order of magnitude as the transducer's lateral spot size of D=1.21 mm.

Results for the hydrophones having no gold on the electrodes were similar but noisier. The bowtie hydrophone with a 200-μm sensitivity zone exhibited a sensitivity of S=0.98 nV/P. The dumbbell hydrophone with a 75-μm sensitivity zone exhibited a sensitivity of S=1.2 nV/Pa.

These results underestimated the sensitivity, however, since the sensitivity zones were much smaller than the US beam spot; even the $(1\ mm)^2$ gold bowtie had only 68% of the area of the transducer's spot size. Increasing the area of the hydrophone would improve apparent sensitivity at the expense of spatial resolution.

Basic pulse/echo (P/E) and AE response signals for the 75-μm ITO dumbbell hydrophone are shown in FIGS. 12(a) and 12(b). Sensitivity data for the same hydrophone are plotted at four levels of transducer pressure in FIG. 13. Specifically, FIG. 13 shows sensitivity versus applied voltage for a 100% ITO (no gold) dumbbell hydrophone with a sensitivity zone of 75 μm, at transducer pressure levels of 125 kPa, 250 kPa, 375 kPa, and 500 kPa. The fitted lines indicate a good linear response for all transducer pressures: correlation coefficient R>0.95 at all pressures except 125 kPa, for which R>0.90. Even at the lowest transducer level of 125 kPa, a least-squares regression of the data shows a strong linear relationship between the sensitivity and the applied voltage, up to 20 V (the limit of the function generator).

The relatively low SNR of the 100% ITO hydrophones can be seen in the resolution profiles of FIG. 14, in which two of these hydrophones are compared to the Onda HGL-0200 (conventional hydrophone) and a bowtie in ITO with gold electrodes. The profiles show the AE signal strength across the center of the raster-scan, in both the x- and y-directions. FWHM (−6 dB) spot images are shown at the top of the figure. The 200-μm bowtie and the 75-μm dumbbell are 100% ITO; the 1-mm bowtie has gold electrodes, except at the sensitivity zone.

The side-lobes of the gold-on-ITO bowtie are clearly visible at −40 dB, while the two all-ITO devices lose definition much earlier. This is likely due to the small sensitivity zones of the ITO hydrophones, compared to the US beam size. Side-lobes are not visible on the Onda hydrophone due to its narrow shape.

Initial estimates of the bandwidth limits, according to simulation models (see below) indicate the presence of 2nd and 3rd harmonics up to 8 MHz or higher. Given that the theoretical upper bound for the bandwidth attributable to the extremely thin structure of the ITO hydrophones is over 10 GHz, these harmonics are simply those of the transducer. This wide bandwidth is far beyond what is commonly seen in Piezo devices, and could be used to shrink spatial resolution by allowing the use of transducers with higher frequencies. However, thinness also reduces sensitivity. This trade-off is similar to trade-offs encountered with conventional piezoelectric and optical detectors of ultrasound, such as etalon hydrophones, which often refer to a Q-factor (higher Q=lower bandwidth, but better sensitivity).

FIGS. 15(a)-15(b) are plots of bandwidth for a 100% ITO (no gold) dumbbell hydrophone having a 75-μm sensitivity zone. FIG. 15(a) is an AE signal time trace, and FIG. 15(b) is a corresponding fast Fourier transform showing $2^{nd}$ and $3^{rd}$ harmonics of the response to the 2.25-MHz transducer.

Example 5

This example is directed to a specific configuration of the optical chamber as well as a specific configuration of the optical system inside the optical chamber.

In this example, the light source was optically connected to the optical chamber by a multi-mode optical fiber. In such a configuration, the optical system collimated light entering the optical chamber from the optical fiber and focused that light at the desired situs in or on the sample. The optical system was situated inside the optical chamber and, in this example, comprised lenses each being approximately 1 inch (2.54 cm) in diameter. More specifically, as shown in FIG. 28, the optical system comprised a positive biconvex lens 72 and a negative biconcave lens 74 situated on the optical axis. The biconvex lens 72 was placed at a fixed axial distance from the proximal terminus of the optical fiber 30 (e.g., 2 inches) such that light exiting the optical fiber nearly saturated the lens (approximately 90% light coverage across the lens surface) to minimize third-order aberrations. Factors governing the selection of lens material included transmissivity in the spectral range of the light and resistance to damage by the light. The biconcave lens 74 was axially movable relative to the biconvex lens 72 in the manner of a zoom lens. One or both lenses 72, 74 in this optical system can be achromats.

In this example, a shutter was placed between the optical fiber 30 and the biconcave lens 74. The shutter provided a way to block the light light in a way other than turning the light source off.

In this embodiment, to make the biconcave lens 74 axially movable relative to the biconvex lens 72, the biconcave lens was mounted to a lens ring 78 comprising multiple, radially extending pins 80 (desirably three). (See FIG. 29.) The lens ring 78 was configured for movement forwardly and rearwardly along the optical axis. The range of movement was 30 mm. For stability of the lens ring 78 during this motion, the pins 80 engaged corresponding slit channels 82 in the walls of the optical chamber 36 that extended parallel to the optical axis. Meanwhile, the outer surface of the lens ring 78 included male helical threads 84 that engaged corresponding female threads 86 on the inside surface of a focusing "barrel" (88). Hence, rotating the barrel 88 around the optical axis caused corresponding motion of the lens ring 78 along the optical axis relative to the optical chamber 36 and relative to the focusing barrel 88. A diagram of this optical chamber is shown in FIG. 29, including the optical chamber 36, lens ring 78 holding the biconcave lens 74, the biconvex lens 72 mounted in a stationary manner in the optical chamber, at least one pin 80, and the male helical threads 84 that engage corresponding female helical threads 86 on the interior surface of the chamber 36.

If desired, the diameter of the optical chamber 36 downstream of the biconvex lens 72 can progressively narrow 92 with increased axial distance from the biconvex lens, in view of the convergence imparted by the biconvex lens on light passing through it. The distal end 90 of the optical chamber connects to a chamber (not shown) 90 containing the light-transmitter/sound reflector and the detector mount.

Example 6

This example is directed to several exemplary arrangements of individual detectors in detector arrays. FIG. 30 depicts a linear (1-D) array. FIG. 31(a)-31(d) depict respective 2-D arrays. For use with a linear array, the optical system in the optical chamber 36 can comprise one or more cylindrical lenses.

Whereas the invention has been described in connection with multiple representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. A device for imaging a situs in a sample, comprising:
an ultrasonic-detector portion comprising at least one ultrasonic transmitter and at least one ultrasonic receiver;
a photoacoustic portion comprising a detector mount, an acoustic-reflection element, and an illumination portion; wherein
the ultrasonic-detector portion is coupled to the detector mount such that the at least one ultrasonic transmitter and at least one ultrasonic receiver are oriented to receive and send ultrasonic beams propagating on a first axis,
the illumination portion is coupled to the detector mount such that the illumination portion directs a pulsatile light beam along a second axis that is different from and intersects the first axis,
the acoustic-reflection element is configured to transmit the light beam from the illumination portion and simultaneously to reflect the ultrasonic beam sent from the ultrasonic transmitter,
the acoustic-reflection element is coupled to the detector mount to receive and transmit the light beam along the second axis, to receive the ultrasonic beam along the first axis, and to reflect the ultrasonic beam to co-propagate with the transmitted light beam along the second axis to the situs to induce the situs simultaneously to produce pulse echoes and photoacoustic pulses that propagate from the situs along the second axis to the acoustic-reflection element, and
the acoustic-reflection element reflecting the pulse echoes and photoacoustic pulses along the first axis to the at least one ultrasonic receiver.

2. A method for producing data concerning a situs in or on a sample, comprising:
combining a pulsed or modulated light beam and an acoustic-pulse beam to form an energy beam in which the acoustic-pulse beam is in-line with the light beam and the energy beam includes both light pulses and acoustic pulses;
impinging the energy beam at a situs on or in the sample to cause the situs to produce acoustic echoes in response to the acoustic pulses incident at the situs and photoacoustic pulses in response to the light pulses incident at the situs; and
detecting the acoustic echoes and photoacoustic pulses to produce data concerning the situs.

3. The method of claim 2, wherein the light beam and the train of acoustic pulses are coaxial with and co-propagate with each other.

4. The method of claim 2, wherein:
the light beam in the energy beam comprises a train of light pulses;
the acoustic-pulse beam in the energy beam comprises a train of acoustic pulses; and
the light pulses and acoustic pulses in the energy beam are synchronous with each other.

5. The method of claim 2, wherein producing the energy beam comprises:
producing the light beam propagating along a first axis extending to the situs;
producing the acoustic-pulse beam propagating along a second axis different from the first axis;

combining the light beam and the acoustic-pulse beam so that the resulting energy beam propagates along the first axis to the situs.

6. The method of claim 5, wherein the second axis is perpendicular to the first axis.

7. The method of claim 5, further comprising:
co-propagating the acoustic echoes and the photoacoustic pulses as a returning acoustic-wave beam back along the first axis; and
splitting the returning acoustic-wave beam from the first axis to an acoustic-detector device.

8. The method of claim 7, wherein the returning acoustic-wave beam is split from the first axis to the second axis, along which the returning acoustic-wave beam propagates to the acoustic-detector device.

9. The method of claim 7, wherein detecting the acoustic echoes and photoacoustic pulses in the returning acoustic-wave beam is performed using an acoustic-detector device comprising an array of multiple acoustic detectors that produce respective data from respective acoustic waves detected by the acoustic detectors.

10. The method of claim 9, further comprising processing the data to produce an image of the situs.

11. The method of claim 9, wherein at least one acoustic detector is an acousto-electric hydrophone configured to produce respective data by respective received acoustic waves in the returning acoustic-wave beam being acousto-electrically converted by the detector to the respective data.

12. The method of claim 2, wherein detecting the acoustic echoes and photoacoustic pulses is performed using an array of multiple individual acoustic detectors that produce respective data from respective received acoustic echoes and photoacoustic pulses.

13. The method of claim 12, further comprising processing the data to produce an image of the situs.

14. The method of claim 12, wherein at least one acoustic detector is an acousto-electric hydrophone configured to produce respective data by respective received acoustic echoes and photoacoustic pulses being acousto-electrically converted by the detector to the respective data.

15. The method of claim 2, wherein combining the light beam and the acoustic-pulse beam comprises interacting these beams with an optical element that transmits incident light and reflects incident acoustic waves, such that the light beams passes through the optical element and the acoustic-pulse beam is reflected by the optical element to form the energy beam.

16. The method of claim 2, further comprising passing the energy beam through an index-matching liquid before the energy beam reaches the sample.

17. The method of claim 2, further comprising shaping the light beam before combining this beam with the acoustic-pulse beam.

18. The method of claim 17, wherein shaping the light beam comprises forming the light beam to converge at the situs.

19. The method of claim 18, further comprising shaping the acoustic-wave beam to converge with the light beam at the situs.

* * * * *